US008729010B2

(12) United States Patent
Rothbard et al.

(10) Patent No.: US 8,729,010 B2
(45) Date of Patent: *May 20, 2014

(54) COMPOSITIONS AND METHODS FOR ENHANCING DRUG DELIVERY ACROSS AND INTO OCULAR TISSUES

(75) Inventors: Jonathan B. Rothbard, Cupertino, CA (US); Paul A. Wender, Menlo Park, CA (US); Leo P. McGrane, Mountain View, CA (US); Lalitha V. S. Sista, Sunnyvale, CA (US); Thorsten A. Kirschberg, Mountain View, CA (US)

(73) Assignee: KAI Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/608,975

(22) Filed: Sep. 10, 2012

(65) Prior Publication Data
US 2013/0096069 A1 Apr. 18, 2013

Related U.S. Application Data

(63) Continuation of application No. 11/800,358, filed on May 4, 2007, now Pat. No. 8,278,264, which is a continuation of application No. 10/083,960, filed on Feb. 25, 2002, now Pat. No. 7,229,961, which is a continuation-in-part of application No. 09/792,480, filed on Feb. 23, 2001, now Pat. No. 6,669,951, which is a continuation-in-part of application No. 09/648,400, filed on Aug. 24, 2000, now Pat. No. 6,593,292.

(60) Provisional application No. 60/150,510, filed on Aug. 24, 1999.

(51) Int. Cl.
*A61K 38/03* (2006.01)
*A61K 38/16* (2006.01)

(52) U.S. Cl.
USPC .......................................... 514/1.2; 514/20.8

(58) Field of Classification Search
None
See application file for complete search history.

(56) References Cited

U.S. PATENT DOCUMENTS 4,046,722 A 9/1977 Rowland
4,532,207 A 7/1985 Brewer et al.
(Continued)

FOREIGN PATENT DOCUMENTS

CA 2094658 A1 10/1993
CA 2291074 A1 11/1998
(Continued)

OTHER PUBLICATIONS

Fabre et al., "Polyglutamylation, an important element in methotrexate cytotoxicity and selectivity in tumor versus murine granulocytic progenitor cells in vitro", Cancer Research, vol. 44, No. 8, pp. 3190-3195 (1984).

(Continued)

*Primary Examiner* — Jeffrey E Russel
(74) *Attorney, Agent, or Firm* — McDermott Will & Emery LLP

(57) ABSTRACT

This invention provides compositions and methods for enhancing delivery of drugs and other agents across epithelial tissues, including into and across ocular tissues and the like. The compositions and methods are also useful for delivery across endothelial tissues, including the blood brain barrier. The compositions and methods employ a delivery enhancing transporter that has sufficient guanidino or amidino sidechain moieties to enhance delivery of a compound conjugated to the reagent across one or more layers of the tissue, compared to the non-conjugated compound. The delivery-enhancing polymers include, for example, poly-arginine molecules that are preferably between about 6 and 25 residues in length.

20 Claims, 30 Drawing Sheets

(56) References Cited

U.S. PATENT DOCUMENTS

| | | | |
|---|---|---|---|
| 4,631,190 A | 12/1986 | Shen et al. | |
| 4,701,521 A | 10/1987 | Ryser et al. | |
| 4,847,240 A | 7/1989 | Ryser et al. | |
| 4,880,911 A | 11/1989 | Brewer et al. | |
| 5,028,707 A | 7/1991 | Nichols et al. | |
| 5,162,505 A | 11/1992 | Dean et al. | |
| 5,268,164 A | 12/1993 | Kozarich et al. | |
| 5,354,844 A | 10/1994 | Beug et al. | |
| 5,362,831 A | 11/1994 | Mongelli et al. | |
| 5,620,013 A | 4/1997 | Bretton | |
| 5,633,230 A | 5/1997 | Twist et al. | |
| 5,646,120 A | 7/1997 | Sumner-Smith et al. | |
| 5,674,849 A | 10/1997 | Twist et al. | |
| 5,716,614 A | 2/1998 | Katz et al. | |
| 5,783,178 A | 7/1998 | Kabanov et al. | |
| 5,789,531 A | 8/1998 | Sumner-Smith et al. | |
| 5,795,909 A | 8/1998 | Shashoua et al. | |
| 5,804,604 A | 9/1998 | Frankel et al. | |
| 5,831,001 A | 11/1998 | Twist et al. | |
| 5,977,163 A | 11/1999 | Li et al. | |
| 6,013,628 A | 1/2000 | Skubitz et al. | |
| 6,077,835 A | 6/2000 | Hanson et al. | |
| 6,089,234 A | 7/2000 | Bretton | |
| 6,306,993 B1 | 10/2001 | Rothbard et al. | |
| 6,495,663 B1 | 12/2002 | Rothbard et al. | |
| 6,593,292 B1 * | 7/2003 | Rothbard et al. | 514/1.2 |
| 6,669,951 B2 * | 12/2003 | Rothbard et al. | 424/436 |
| 6,730,293 B1 | 5/2004 | Rothbard et al. | |
| 6,759,387 B2 | 7/2004 | Rothbard et al. | |
| 7,229,961 B2 * | 6/2007 | Rothbard et al. | 514/1.2 |
| 8,278,264 B2 * | 10/2012 | Rothbard et al. | 514/1.2 |
| 2002/0009491 A1 | 1/2002 | Rothbard et al. | |
| 2003/0022831 A1 | 1/2003 | Rothbard et al. | |
| 2004/0186045 A1 | 9/2004 | Rothbard et al. | |
| 2007/0173436 A1 | 7/2007 | Rothbard et al. | |
| 2011/0206610 A1 | 8/2011 | Rothbard et al. | |

FOREIGN PATENT DOCUMENTS

| | | |
|---|---|---|
| CA | 2400099 A1 | 8/2001 |
| CA | 2438326 A1 | 9/2002 |
| CA | 2438784 A1 | 9/2002 |
| EP | 0009498 A1 | 4/1980 |
| EP | 0599303 A2 | 6/1994 |
| GB | 744988 A | 2/1956 |
| JP | 61-275216 A | 12/1986 |
| JP | 06-506942 A | 8/1994 |
| JP | 10-095738 A | 4/1998 |
| JP | 10-204000 A | 8/1998 |
| WO | WO 79/00515 A1 | 8/1979 |
| WO | WO 91/09958 A2 | 7/1991 |
| WO | WO 92/07871 A1 | 5/1992 |
| WO | WO 93/04701 A1 | 3/1993 |
| WO | WO 93/21941 A1 | 11/1993 |
| WO | WO 94/04686 A1 | 3/1994 |
| WO | WO 94/14464 A1 | 7/1994 |
| WO | WO 95/11038 A1 | 4/1995 |
| WO | WO 96/21036 A2 | 7/1996 |
| WO | WO 97/33552 A1 | 9/1997 |
| WO | WO 97/40854 A2 | 11/1997 |
| WO | WO 98/52614 A2 | 11/1998 |
| WO | WO 00/50093 A1 | 8/2000 |
| WO | WO 01/13957 A2 | 3/2001 |
| WO | WO 01/62297 A1 | 8/2001 |
| WO | WO 02/07773 A2 | 1/2002 |
| WO | WO 02/065986 A2 | 8/2002 |
| WO | WO 02/067917 A1 | 9/2002 |

OTHER PUBLICATIONS

International Search Report mailed Apr. 26, 2001 for PCT Application No. PCT/US00/23440, filed Aug. 24, 2000, 11 pages, application now published as International Publication Number WO 01/013957 on Mar. 1, 2001.

International Search Report mailed May 29, 2002 for PCT Application No. PCT/US02/05804, filed Feb. 25, 2002, 3 pages, application now published as International Publication Number WO 02/067917 on Sep. 6, 2002.

International Search Report mailed Jul. 3, 2002 for PCT Application No. PCT/US02/05829, filed Feb. 25, 2002, 3 pages, application now published as International Publication Number WO 02/069930 on Sep. 12, 2002.

Kato et al., "Antiumor activity of U-β-D-arabinofuranosylcytosine conjugated with polyglutamic acid and its derivative", Cancer Research, vol. 44, No. 1, pp. 25-30 (1984).

Li et al., "Development of a highly efficacious water-soluable polymer-taxol coonjugate", Proceedings of the 88th Annual Meeting of the American Association for Cancer Research, San Diego, CA Apr. 12-19, 1997, vol. 38, pp. 258, Abstract #1731 (1997).

Lin et al., "Addition of a polyarginine linker to cyclosporine A facilitates transcutaneous delivery and topical inhibition of cutaneous inflammation", J Inv. Derm., vol. 114, No. 4, pp. 777, Abstract: #155 (2000).

Morimoto et al., "Anitumor agent poly (amino acid) conjugates as a drug carrier in cancer chemotherapy", Journal of Pharmacobio-Dynamics, vol. 7, No. 9, pp. 688-698 (1984).

Rothbard et al., "Conjugation of arginine oligomers to cyclosporin a facilitates topical delivery and inhibition of inflammation", Nature Medicine, vol. 6, No. 11, pp. 1253-1257 (2000).

Wender et al., "The design, synthesis and evaluation of molecules that enable or enhance cellular uptake: Peptoid moleculer transporters", PNAS USA, vol. 97, No. 24, pp. 13003-13008 (2000).

Willner et al., "(6-Maleimidocaproyl) Hydrazone of Doxorubicin-A new Derivative for the Preparation of Immunoconjugates of Doxorubicin", Bioconjugate Chemistry, vol. 4, pp. 521-527 (1993).

Zhang et al., "Growth factors secreted by bronchial epithelial cells control myofibroblast proliferation: an in vitro co-culture model of airway remodeling in asthma", Laboratory Investigation, vol. 79, No. 4, pp. 395-405 (1999).

Aoyagi et al., "Polymerization of benzalkonium chloride-type monomer and application to percutaneous drug absorption enhancer", Journal of Controlled Release, vol. 13, No. 1, pp. 63-71 (1990).

Arbuck et al., "Taxol: Clinical Results and Current Issues in Development,"Chapter 14 in *TAXOL©: Science and Applications*, M. Suffness ed., CRC Press: New York, pp. 379-415 (1995).

Babiuk et al., "Cutaneous vaccination: the skin as an immunologically active tissue and the challenge of antigen delivery," Journal of Controlled Release, vol. 66, pp. 199-214 (2000).

Balicki et al., "Histone H2A Significantly Enhances In Vitro DNA Transfection," Molecular Medicine, vol. 3, No. 11, pp. 782-787 (1997).

Boussif et al., "A versatile vector for gene and oligonucleotide transfer into cells in culture and in vivo: polyethylenimine", Proc. Natl. Acad Sci. USA, vol. 92, pp. 7297-7301 (1995).

Brugidou et al., "The retro-inverso form of a homeobox-derived short peptide is rapidly internalised by cultured neurones: a new basis for an efficient intracellular delivery system", Biochemical and Biophysical Research Communications, vol. 214, No. 2, pp. 685-693 (1995).

Burton et al., "Basic polyelectrolytes and protein transport across the new-born pig intestine", Physiological Society, vol. 211, No. 2, 27P-28P (1970).

Buschle et al., "Transloading of tumor antigen-derived peptides into antigen-presenting cells", PNAS, vol. 94, pp. 3256-3261 (1997).

Chen et al., "Galactosylated histone-mediated gene transfer and expression", Human Gene Therapy, vol. 5, pp. 429-435.

Colin et al., "Liposomes enhance delivery and expression of an rgd-oligolysine gene transfer vector in human tracheal cells", Gene Therapy, vol. 5, pp. 1488-1498 (1998).

Cooke et al., "Nitric oxide synthase: role in the genesis of vascular disease", Annu. Rev. Med., vol. 48, pp. 489-509 (1997).

Coyle et al., "Role of cationic proteins in the airway hyperresponsiveness due to airway inflammation", Am. Respir. Crit. Care Med., vol. 150, pp. 263-571 (1994).

Dattilo et al., "Inducible nitric oxide synthase expression in human vein grafts", Am. J Surg., vol. 174, pp. 177-180 (1997).

(56) References Cited

OTHER PUBLICATIONS

De Bont et al., "Synthesis and biological activity of .beta.glucuronyl carbamate-based pro drugs of paclitaxel as potential canidates for ADEPT", Bioorganic & Medicinal Chemistry, vol. 5, No. 2, pp. 405-414 (1997).
Derossi et al., "The third helix of the antennapedia homeodomain translocates through biological membranes", The Journal of Biological Chemistry, vol. 269, No. 14, pp. 10444-10450 (1994).
Elferink, "Changes of plasma membrane permeability in neutrophils treated with polycations", Inflammation, vol. 15, No. 2, pp. 103-115. (1991).
Emi et al., "Gene transfer mediated by polyarginine requires a formation of big carrier-complex of dna aggregate", Biochemical and Biophysical Research Communications, vol. 231, pp. 421-424 (1997).
Fawell et al., "Tat-mediated delivery of heterologous proteins into cells", Proc. Natl. Acad. Sci. USA, vol. 91, pp. 664-668 (1994).
Fletcher et al., "Partially modified retro-inverso peptides: development, synthesis, and conformational behavior", Chem. Rev., vol. 96, pp. 763-795 (1998).
Gama et al., "CA2+-sensing receptors in intestinal epithelium", American Journal of Physiology, vol. 273, No. 4, Part 1, pp. C1168-C1175 (1997).
Garg et al., "Nitric oxide-generating vasodilators and 8-bromo-cyclic guanosine monophosphate inhibit mitogenesis and proliferation of cultured rat vascular smooth muscle cells," J Clin. Invest., vol. 83, pp. 1774-1777 (1989).
George et al., "The medicinal chemistry of taxol", Chapter 13 in TAXOL©: Science and Applications, M. Suffness ed., CRC Press: New York, pp. 317-375 (1995).
Golik et al., "Synthesis and antitumor evaluation of paclitaxel phosphonooxymethyl ethers: a novel class of water soluble paclitaaxel pro-drugs", Bioorganic & Medicinal Chemistry Letters, vol. 6, No. 15, 1837-1842 (1996).
Greenwald et al., "Drug delivery systems: water soluble taxol 2'-poly(ethylene glycol) ester prodrugs-design and in vivo effectiveness", J Med. Chem, vol. 39, No. 2, pp. 424-431 (1996).
Hosoya et al., "Effect of several hydrophilic polymers on the permeation of morphine and salicylic acid through excised hairless rat skin", Chem. Pharm. Bull. vol. 46, No. 5, pp. 882-885 (1998).
Hulsmann et al., "Permeability of human isolated airways increases after hydrogen peroxide and poly-L-arginine", Am. J Respir. Crit. Care Med., vol. 153, No. 2, pp. 841-846 (1996).
Kessler, "Peptoids—a new approach to the development of pharmaceuticals", Angew Chem. Int. Ed. Engl. vol. 32, No. 4, pp. 543-544 (1993).
Kingston, "Natural toxoids: structure and chemistry", Chapter 12 in TAXOL©: Science & Applications, M. Suffness, ed., CRC Press: New York, pp. 287-315 (1995).
Kobayashi,. "Composition for transmucosally absorbable preparation", Patent Abstracts of Japan, Publication No. 10095738, Publication Date Apr. 4, 1998.
Lam et al., "The one-bead-one-compound combinatorial library method", Chem. Rev., vol. 97, pp. 411-448 (1997).
Lloyd-Jones et al., "The vascular biology of nitric oxide and its role in atherogenesis", Annu. Rev. Med., vol. 47, pp. 365-375 (1996).
Mauersberger et al., "Untersuchungen zur zytotoxizitat von poly-L-arginin, poly-L-lysin and deae-dextran bei L-zellen und mauseembryofibroblasten", Exp. Path., vol. 18, pp. 268-274 (1977).
Murphy et al., "A combinatorial approach to the discovery of efficient cationic peptoid reagents for gene delivery", Proc. Natl. Acad. Sci. USA, vol. 95, pp. 1517-1522 (1998).
Natsume et al., "Screening of absorption enhancers for nasal peptide and protein delivery", Proceed. Intern. Symp. Control. Rel. Bioact. Mater, vol. 23, pp. 481-482 (1996).
Nicolaou et al., "Design, synthesis and biological activity of protaxols", Nature, vol. 364, pp. 464-466 (1993).
Perr et al., "Protamine selectively inhibits collagen synthesis by human intestinal smooth muscle cells and other mesenchymal cells", Journal of Cellular Physiology, vol. 140, No. 3, pp. 463-470 (1989).
Peterson et al., "Polyamino acid enhancement of bacterial phagocytosis by human polymorphonuclear leukocytes and peritoneal macrophages", Infection and Immunity, vol. 43, No. 2, pp. 561-566 (1984).
Rodrigues et al., "Synthesis and β-lactamase-mediated activation of a cephalosporin-taxol prodrug", Chemistry and Biology, vol. 2, pp. 223-227 (1995).
Rose, "Preclinical antitumor activity of taxanes", Chapter in TAXOL©: Science & Applications, M. Suffness, ed., CRC Press: New York, pp. 209-235 (1995).
Santana et al., "Inrflammatory responses induced by poly-L-arginine in rat lungs in vivo", Agents Actions, vol. 39, No. 3-4, pp. 104-110 (1993).
Simon et al., "Peptoids: a modular approach to drug discovery", Proc. Natl. Acad. Sci. USA, vol. 89, pp. 9367-9371 (1992).
Straubinger, "Biopharmaceutics of paclitaxei (Taxol): formulation, activity, and pharmacokinetics", Chapter 9 in TAXOL©: Science & Applications, M. Suffness, ed., CRC Press: New York, pp. 237-258 (1995).
Sumner-Smith et al., "123: 79357m Antiherpetic activities of N-α-acetyl-nona-D-=arginine amide acetate", Chemical Abstracts, vol. 123, No. 7, pp. 606 (1995).
Sumner-Smith et al., "Antiherpetic activities of N-α- acetyl-nona-D-arginine amide acetate", Drugs Exptl. Clin. Res., vol. XXI, No. 1, pp. 1-6 (1995).
Thompson et al., "Synthesis and applications of small molecule libraries", Chem. Rev., vol. 96, pp. 555-600 (1996).
Tsao et al., "Nitric oxide regulates monocyte chemotactic protein-I", Circulation, vol. 96, pp. 934-940 (1997).
Tzan et al., "Mammalian urinary bladder permeability is altered by cationic proteins modulation by divalent cations", American Journal of Physiology, vol. 267, No. 4, Part 1, pp. C1013-C1026 (1994).
Tzan et al., "Modification of epithelial permeability by cationic polypeptides", American Journal of Physiology, vol. 265, No. 6, Part 1, pp. C1637-C1647 (1993).
Uchida et al., "Polycations Decrease the Transepithelial Resistance of Cultured Tracheal Epithelial Cells", Chest, vol. 101, No. 3, pp. 33S (1992).
Uchida et al., "Cationic proteins increase the permeability of cultured rabbit tracheal epthihelial cells: modification by heparin and extracellular calcium", Experimental Lung Research, vol. 22, No. 1, pp. 85-99 (1996).
Ueda et al., "Novel water soluble phosphate prodrugs of Taxol© possessing in vivo antitumor activity", Bioorganic and Medicinal Chemistry Letters, vol. 3, No. 8, pp. 1761-1766 (1993).
Ueda et al., "Synthesis and antitumor evaluation of 2'-oxycarbonylpaclitaxels (Paclitaxel-2'-Carbonates)", Bioorganic & Medicinal Chemistry Letters, vol. 4, No. 15, pp. 1861-1864 (1994).
Vyas et al., "Synthesis and antitumor evaluation of water soluble taxol phosphates", Bioorganic & Medicinal Chemistry Letters, vol. 3, No. 6, pp. 1357-1360 (1993).
Vyas et al., "Phosphatase-activated prodrugs of paclitaxel", Chapter 9 in Taxane Anticancer Agents, American Chemical Society, pp. 124 (1995).
Wei et al., "Synthesis of oligoarginineoligonucleotide conjugates and oligoarginine-bridge oligonucleotide pairs", Bioconjugate Chem., vol. 5, pp. 468-474 (1994).
Wolf et al., "Dietary L-arginine supplementation normalizes platelet aggregation in hypercholesterolemic humans", JACC, vol. 29, No. 3, pp. 479-485 (1997).
Zuckermann et al., "Efficient Method for the Preparation of Peptoids [Oligo(N-substituted glycines)] by Submonomer Solid Phase Synthesis", Chemtracts-Macromolecular Chemistry, vol. 4, pp. 80-83 (1993).

\* cited by examiner n = 5, 7, 9, 0 (control)

I

II

III

IV

A.

B.

n = 5 and 7

Synthetic Schemes for FK 506 Conjugates

Synthetic Schemes for FK 506 Conjugates (contd.)

SEQUENCE LISTING

```
<160> NUMBER OF SEQ ID NOS: 86

<210> SEQ ID NO 1
<211> LENGTH: 5
<212> TYPE: PRT
<213> ORGANISM: Artificial Sequence
<220> FEATURE:
<223> OTHER INFORMATION: R5 Arg homopolymer

<400> SEQUENCE: 1

Arg Arg Arg Arg Arg
1               5

<210> SEQ ID NO 2
<211> LENGTH: 6
```

```
<212> TYPE: PRT
<213> ORGANISM: Artificial Sequence
<220> FEATURE:
<223> OTHER INFORMATION: R6 Arg homopolymer

<400> SEQUENCE: 2

Arg Arg Arg Arg Arg Arg
 1               5

<210> SEQ ID NO 3
<211> LENGTH: 7
<212> TYPE: PRT
<213> ORGANISM: Artificial Sequence
<220> FEATURE:
<223> OTHER INFORMATION: R7 Arg homopolymer, L-Arg heptamer

<400> SEQUENCE: 3

Arg Arg Arg Arg Arg Arg Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: R8 Arg homopolymer

<400> SEQUENCE: 4

Arg Arg Arg Arg Arg Arg Arg Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: R9 Arg homopolymer

<400> SEQUENCE: 5

Arg Arg Arg Arg Arg Arg Arg Arg Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: L-Arg heptamer after release of cyclosporine by
      cleavage of the pH sensitive linker group
<220> FEATURE:
<221> NAME/KEY: MOD_RES
<222> LOCATION: (1)...(1)
<223> OTHER INFORMATION: Xaa =
      2-[4-benzyl-2,5-diketopiperazinyl]-acetyl-arginine

<400> SEQUENCE: 6

Xaa Arg Arg Arg Arg Arg Arg
 1               5

<210> SEQ ID NO 7
<211> LENGTH: 10
<212> TYPE: PRT
<213> ORGANISM: Artificial Sequence
<220> FEATURE:
<223> OTHER INFORMATION: unlabeled peptide
<220> FEATURE:
<221> NAME/KEY: MOD_RES
<222> LOCATION: (10)...(10)
<223> OTHER INFORMATION: Xaa = cysteinamide
```

-continued

```
<400> SEQUENCE: 7

Arg Arg Arg Arg Arg Arg Gly Gly Xaa
 1               5                    10

<210> SEQ ID NO 8
<211> LENGTH: 10
<212> TYPE: PRT
<213> ORGANISM: Artificial Sequence
<220> FEATURE:
<223> OTHER INFORMATION: analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 8

Xaa Arg Lys Lys Arg Arg Gln Arg Arg Arg
 1               5                    10

<210> SEQ ID NO 9
<211> LENGTH: 9
<212> TYPE: PRT
<213> ORGANISM: Artificial Sequence
<220> FEATURE:
<223> OTHER INFORMATION: Tat-49-56 truncated analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 9

Xaa Arg Lys Lys Arg Arg Gln Arg Arg
 1               5

<210> SEQ ID NO 10
<211> LENGTH: 8
<212> TYPE: PRT
<213> ORGANISM: Artificial Sequence
<220> FEATURE:
<223> OTHER INFORMATION: Tat-49-55 truncated analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 10

Xaa Arg Lys Lys Arg Arg Gln Arg
 1               5

<210> SEQ ID NO 11
<211> LENGTH: 9
<212> TYPE: PRT
<213> ORGANISM: Artificial Sequence
<220> FEATURE:
<223> OTHER INFORMATION: Tat-50-57 truncated analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 11

Xaa Lys Lys Arg Arg Gln Arg Arg Arg
 1               5

<210> SEQ ID NO 12
<211> LENGTH: 8
```

```
<212> TYPE: PRT
<213> ORGANISM: Artificial Sequence
<220> FEATURE:
<223> OTHER INFORMATION: Tat-51-57 truncated analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 12

Xaa Lys Arg Arg Gln Arg Arg Arg
 1               5

<210> SEQ ID NO 13
<211> LENGTH: 10
<212> TYPE: PRT
<213> ORGANISM: Artificial Sequence
<220> FEATURE:
<223> OTHER INFORMATION: A-49 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 13

Xaa Ala Lys Lys Arg Arg Gln Arg Arg Arg
 1               5                   10

<210> SEQ ID NO 14
<211> LENGTH: 10
<212> TYPE: PRT
<213> ORGANISM: Artificial Sequence
<220> FEATURE:
<223> OTHER INFORMATION: A-50 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 14

Xaa Arg Ala Lys Arg Arg Gln Arg Arg Arg
 1               5                   10

<210> SEQ ID NO 15
<211> LENGTH: 10
<212> TYPE: PRT
<213> ORGANISM: Artificial Sequence
<220> FEATURE:
<223> OTHER INFORMATION: A-51 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 15

Xaa Arg Lys Ala Arg Arg Gln Arg Arg Arg
 1               5                   10

<210> SEQ ID NO 16
<211> LENGTH: 10
<212> TYPE: PRT
<213> ORGANISM: Artificial Sequence
<220> FEATURE:
<223> OTHER INFORMATION: A-52 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
```

```
                            (Fl-ahx)

<400> SEQUENCE: 16

Xaa Arg Lys Lys Ala Arg Gln Arg Arg Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: A-53 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 17

Xaa Arg Lys Lys Arg Ala Gln Arg Arg Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: A-54 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 18

Xaa Arg Lys Lys Arg Arg Ala Arg Arg Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: A-55 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 19

Xaa Arg Lys Lys Arg Arg Gln Ala Arg Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: A-56 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 20

Xaa Arg Lys Lys Arg Arg Gln Arg Ala Arg
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: A-57 alanine-substituted analog of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 21

Xaa Arg Lys Lys Arg Arg Gln Arg Arg Ala
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Tat-57-49 retro-isomer of Tat-49-57
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 22

Xaa Arg Arg Arg Gln Arg Arg Lys Lys Arg
1               5                   10

<210> SEQ ID NO 23
<211> LENGTH: 6
<212> TYPE: PRT
<213> ORGANISM: Artificial Sequence
<220> FEATURE:
<223> OTHER INFORMATION: R5 Arg oligomer
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 23

Xaa Arg Arg Arg Arg Arg
1               5

<210> SEQ ID NO 24
<211> LENGTH: 7
<212> TYPE: PRT
<213> ORGANISM: Artificial Sequence
<220> FEATURE:
<223> OTHER INFORMATION: R6 Arg oligomer
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 24

Xaa Arg Arg Arg Arg Arg Arg
1               5

<210> SEQ ID NO 25
<211> LENGTH: 8
<212> TYPE: PRT
<213> ORGANISM: Artificial Sequence
<220> FEATURE:
<223> OTHER INFORMATION: R7 Arg oligomer
<220> FEATURE:
<221> NAME/KEY: MOD_RES
```

```
<222> LOCATION: (1)...(1)
<223> OTHER INFORMATION: Xaa = fluorescein conjugated aminohexanoic acid
      (Fl-ahx)

<400> SEQUENCE: 25

Xaa Arg Arg Arg Arg Arg Arg
1               5

<210> SEQ ID NO 26
<211> LENGTH: 9
<212> TYPE: PRT
<213> ORGANISM: Artificial Sequence
<220> FEATURE:
<223> OTHER INFORMATION: R8 Arg oligomer
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 26

Xaa Arg Arg Arg Arg Arg Arg Arg Arg
1               5

<210> SEQ ID NO 27
<211> LENGTH: 10
<212> TYPE: PRT
<213> ORGANISM: Artificial Sequence
<220> FEATURE:
<223> OTHER INFORMATION: R9 Arg oligomer
<220> FEATURE:
<221> NAME/KEY: MOD_RES
<222> LOCATION: (1)...(1)
<223> OTHER INFORMATION: Xaa = fluorescein conjugated aminohexanoic acid
      (Fl-ahx)

<400> SEQUENCE: 27

Xaa Arg Arg Arg Arg Arg Arg Arg Arg Arg
1               5                   10

<210> SEQ ID NO 28
<211> LENGTH: 9
<212> TYPE: PRT
<213> ORGANISM: Artificial Sequence
<220> FEATURE:
<223> OTHER INFORMATION: HIV-1 Tat protein basic region

<400> SEQUENCE: 28

Arg Lys Lys Arg Arg Gln Arg Arg Arg
1               5

<210> SEQ ID NO 29
<211> LENGTH: 16
<212> TYPE: PRT
<213> ORGANISM: Artificial Sequence
<220> FEATURE:
<223> OTHER INFORMATION: Antennapedia homeodomain region residues 43-58

<400> SEQUENCE: 29

Arg Gln Ile Lys Ile Trp Phe Gln Asn Arg Arg Met Lys Trp Lys Lys
1               5                   10                  15

<210> SEQ ID NO 30
<211> LENGTH: 17
<212> TYPE: PRT
<213> ORGANISM: Artificial Sequence
<220> FEATURE:
<223> OTHER INFORMATION: Antennapedia homeodomain region residues 43-58
<220> FEATURE:
<221> NAME/KEY: MOD_RES
```

```
<222> LOCATION: (1)...(1)
<223> OTHER INFORMATION: Xaa = fluorescein conjugated aminohexanoic acid
      (Fl-ahx)

<400> SEQUENCE: 30

Xaa Arg Gln Ile Lys Ile Trp Phe Gln Asn Arg Arg Met Lys Trp Lys
 1               5                  10                  15

Lys

<210> SEQ ID NO 31
<211> LENGTH: 8
<212> TYPE: PRT
<213> ORGANISM: Artificial Sequence
<220> FEATURE:
<223> OTHER INFORMATION: delivery enhancing transporter moiety
      DTPA-aca-R7-CO2H
<220> FEATURE:
<221> NAME/KEY: MOD_RES
<222> LOCATION: (1)...(1)
<223> OTHER INFORMATION: amino acaproic acid (aca) linked to
      diethylenetriaminepentaacetic acid (DTPA)

<400> SEQUENCE: 31

Xaa Arg Arg Arg Arg Arg Arg Arg
 1               5

<210> SEQ ID NO 32
<211> LENGTH: 8
<212> TYPE: PRT
<213> ORGANISM: Artificial Sequence
<220> FEATURE:
<223> OTHER INFORMATION: delivery enhancing transporter moiety
      NH-2-R-7CCONH-2.8TFA
<220> FEATURE:
<221> NAME/KEY: MOD_RES
<222> LOCATION: (8)...(8)
<223> OTHER INFORMATION: Xaa = cysteinaminde

<400> SEQUENCE: 32

Arg Arg Arg Arg Arg Arg Arg Xaa
 1               5

<210> SEQ ID NO 33
<211> LENGTH: 7
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(5)
<223> OTHER INFORMATION: Xaa = Gly, beta-alanine, gamma-amino butyric
      acid or epsilon-amino caproic acid

<400> SEQUENCE: 33

Arg Xaa Arg Arg Xaa Arg Arg
 1               5

<210> SEQ ID NO 34
<211> LENGTH: 10
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
```

```
<222> LOCATION: (2)..(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)..(5)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)..(8)
<223> OTHER INFORMATION: Xaa = Gly, beta-alanine, gamma-amino butyric
      acid or epsilon-amino caproic acid

<400> SEQUENCE: 34

Arg Xaa Arg Arg Xaa Arg Arg Xaa Arg Arg
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)..(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)..(5)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)..(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)..(11)
<223> OTHER INFORMATION: Xaa = Gly, beta-alanine, gamma-amino butyric
      acid or epsilon-amino caproic acid

<400> SEQUENCE: 35

Arg Xaa Arg Arg Xaa Arg Arg Xaa Arg Arg Xaa Arg Arg
 1               5                  10

<210> SEQ ID NO 36
<211> LENGTH: 16
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)..(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)..(5)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)..(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)..(11)
<223> OTHER INFORMATION: Xaa = Gly, beta-alanine, gamma-amino butyric
      acid or epsilon-amino caproic acid
<220> FEATURE:
```

-continued

```
<221> NAME/KEY: MOD_RES
<222> LOCATION: (14)...(14)
<223> OTHER INFORMATION: Xaa = Gly, beta-alanine, gamma-amino butyric
      acid or epsilon-amino caproic acid

<400> SEQUENCE: 36

Arg Xaa Arg Arg Xaa Arg Arg Xaa Arg Arg Xaa Arg Arg Xaa Arg Arg
1               5                   10                  15

<210> SEQ ID NO 37
<211> LENGTH: 10
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly or epsilon-amino caproic acid
<220> FEATURE:
<221> NAME/KEY: MOD_RES
<222> LOCATION: (5)...(5)
<223> OTHER INFORMATION: Xaa = Gly or epsilon-amino caproic acid
<220> FEATURE:
<221> NAME/KEY: MOD_RES
<222> LOCATION: (8)...(8)
<223> OTHER INFORMATION: Xaa = Gly or epsilon-amino caproic acid

<400> SEQUENCE: 37

Arg Xaa Arg Arg Xaa Arg Arg Xaa Arg Arg
1               5                   10

<210> SEQ ID NO 38
<211> LENGTH: 9
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid

<400> SEQUENCE: 38

Arg Xaa Arg Xaa Arg Xaa Arg Xaa Arg
1               5

<210> SEQ ID NO 39
<211> LENGTH: 11
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
```

-continued

```
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid

<400> SEQUENCE: 39

Arg Xaa Arg Xaa Arg Xaa Arg Xaa Arg Xaa Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (12)...(12)
<223> OTHER INFORMATION: Xaa = Gly, beta-alanine, gamma-amino butyric
      acid or epsilon-amino caproic acid

<400> SEQUENCE: 40

Arg Xaa Arg Xaa Arg Xaa Arg Xaa Arg Xaa Arg Xaa Arg
1               5                   10

<210> SEQ ID NO 41
<211> LENGTH: 15
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
```

```
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (12)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(14)
<223> OTHER INFORMATION: Xaa = Gly, beta-alanine, gamma-amino butyric
      acid or epsilon-amino caproic acid

<400> SEQUENCE: 41

Arg Xaa Arg Xaa Arg Xaa Arg Xaa Arg Xaa Arg Xaa Arg Xaa Arg
 1               5                  10                  15

<210> SEQ ID NO 42
<211> LENGTH: 17
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (12)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(14)
<223> OTHER INFORMATION: Xaa = Gly, beta-alanine, gamma-amino butyric
      acid or epsilon-amino caproic acid
<220> FEATURE:
```

```
<221> NAME/KEY: MOD_RES
<222> LOCATION: (16)...(16)
<223> OTHER INFORMATION: Xaa = Gly, beta-alanine, gamma-amino butyric
      acid or epsilon-amino caproic acid

<400> SEQUENCE: 42

Arg Xaa Arg Xaa Arg Xaa Arg Xaa Arg Xaa Arg Xaa Arg Xaa Arg Xaa
 1               5                  10                  15

Arg

<210> SEQ ID NO 43
<211> LENGTH: 19
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (12)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(14)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (16)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(18)
<223> OTHER INFORMATION: Xaa = Gly, beta-alanine, gamma-amino butyric
      acid or epsilon-amino caproic acid

<400> SEQUENCE: 43

Arg Xaa Arg Xaa Arg Xaa Arg Xaa Arg Xaa Arg Xaa Arg Xaa Arg Xaa
 1               5                  10                  15

Arg Xaa Arg

<210> SEQ ID NO 44
<211> LENGTH: 21
<212> TYPE: PRT
<213> ORGANISM: Artificial Sequence
<220> FEATURE:
<223> OTHER INFORMATION: delivery enhancing transporter moiety
<220> FEATURE:
```

```
<221> NAME/KEY: MOD_RES
<222> LOCATION: (2)...(2)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (4)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(10)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (12)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(14)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (16)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(18)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (20)...(20)
<223> OTHER INFORMATION: Xaa = Gly, beta-alanine, gamma-amino butyric
      acid or epsilon-amino caproic acid

<400> SEQUENCE: 44

Arg Xaa Arg Xaa Arg Xaa Arg Xaa Arg Xaa Arg Xaa Arg Xaa Arg Xaa
 1               5                   10                  15

Arg Xaa Arg Xaa Arg
            20

<210> SEQ ID NO 45
<211> LENGTH: 13
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(2)
<223> OTHER INFORMATION: Xaa = Gly or epsilon-amino caproic acid
<220> FEATURE:
<221> NAME/KEY: MOD_RES
<222> LOCATION: (4)...(4)
<223> OTHER INFORMATION: Xaa = Gly or epsilon-amino caproic acid
<220> FEATURE:
<221> NAME/KEY: MOD_RES
<222> LOCATION: (6)...(6)
<223> OTHER INFORMATION: Xaa = Gly or epsilon-amino caproic acid
<220> FEATURE:
<221> NAME/KEY: MOD_RES
<222> LOCATION: (8)...(8)
```

-continued

```
<223> OTHER INFORMATION: Xaa = Gly or epsilon-amino caproic acid
<220> FEATURE:
<221> NAME/KEY: MOD_RES
<222> LOCATION: (10)...(10)
<223> OTHER INFORMATION: Xaa = Gly or epsilon-amino caproic acid
<220> FEATURE:
<221> NAME/KEY: MOD_RES
<222> LOCATION: (12)...(12)
<223> OTHER INFORMATION: Xaa = Gly or epsilon-amino caproic acid

<400> SEQUENCE: 45

Arg Xaa Arg Xaa Arg Xaa Arg Xaa Arg Xaa Arg Xaa Arg
 1               5                  10

<210> SEQ ID NO 46
<211> LENGTH: 13
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid

<400> SEQUENCE: 46

Arg Xaa Xaa Arg Xaa Xaa Arg Xaa Xaa Arg Xaa Xaa Arg
 1               5                  10

<210> SEQ ID NO 47
<211> LENGTH: 16
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(15)
<223> OTHER INFORMATION: Xaa = Gly, beta-alanine, gamma-amino butyric
      acid or epsilon-amino caproic acid
```

-continued

```
<400> SEQUENCE: 47

Arg Xaa Xaa Arg Xaa Xaa Arg Xaa Xaa Arg Xaa Xaa Arg Xaa Xaa Arg
1               5                   10                  15

<210> SEQ ID NO 48
<211> LENGTH: 19
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(15)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (17)...(18)
<223> OTHER INFORMATION: Xaa = Gly, beta-alanine, gamma-amino butyric
      acid or epsilon-amino caproic acid

<400> SEQUENCE: 48

Arg Xaa Xaa Arg Xaa Xaa Arg Xaa Xaa Arg Xaa Xaa Arg Xaa Xaa Arg
1               5                   10                  15

Xaa Xaa Arg

<210> SEQ ID NO 49
<211> LENGTH: 22
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
```

```
<222> LOCATION: (14)...(15)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (17)...(18)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (20)...(21)
<223> OTHER INFORMATION: Xaa = Gly, beta-alanine, gamma-amino butyric
      acid or epsilon-amino caproic acid

<400> SEQUENCE: 49

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg
            20

<210> SEQ ID NO 50
<211> LENGTH: 25
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(15)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (17)...(18)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (20)...(21)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (23)...(24)
<223> OTHER INFORMATION: Xaa = Gly, beta-alanine, gamma-amino butyric
      acid or epsilon-amino caproic acid

<400> SEQUENCE: 50

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg
            20                  25

<210> SEQ ID NO 51
```

```
<211> LENGTH: 28
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(15)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (17)...(18)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (20)...(21)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (23)...(24)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (26)...(27)
<223> OTHER INFORMATION: Xaa = Gly, beta-alanine, gamma-amino butyric
      acid or epsilon-amino caproic acid

<400> SEQUENCE: 51

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg Xaa Xaa Arg
            20                  25

<210> SEQ ID NO 52
<211> LENGTH: 31
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (5)...(6)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (8)...(9)
<223> OTHER INFORMATION: Xaa = Gly, beta-alanine, gamma-amino butyric
```

-continued

```
       acid or epsilon-amino caproic acid
<220> FEATURE:
<221> NAME/KEY: MOD_RES
<222> LOCATION: (11)...(12)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (14)...(15)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (17)...(18)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (20)...(21)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (23)...(24)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (26)...(27)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (29)...(30)
<223> OTHER INFORMATION: Xaa = Gly, beta-alanine, gamma-amino butyric
       acid or epsilon-amino caproic acid

<400> SEQUENCE: 52

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg Xaa Xaa Arg Xaa Xaa Arg
             20                  25                  30

<210> SEQ ID NO 53
<211> LENGTH: 19
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(3)
<223> OTHER INFORMATION: Xaa = Gly or epsilon-amino caproic acid
<220> FEATURE:
<221> NAME/KEY: MOD_RES
<222> LOCATION: (5)...(6)
<223> OTHER INFORMATION: Xaa = Gly or epsilon-amino caproic acid
<220> FEATURE:
<221> NAME/KEY: MOD_RES
<222> LOCATION: (8)...(9)
<223> OTHER INFORMATION: Xaa = Gly or epsilon-amino caproic acid
<220> FEATURE:
<221> NAME/KEY: MOD_RES
<222> LOCATION: (11)...(12)
<223> OTHER INFORMATION: Xaa = Gly or epsilon-amino caproic acid
<220> FEATURE:
<221> NAME/KEY: MOD_RES
<222> LOCATION: (14)...(15)
<223> OTHER INFORMATION: Xaa = Gly or epsilon-amino caproic acid
<220> FEATURE:
<221> NAME/KEY: MOD_RES
<222> LOCATION: (17)...(18)
<223> OTHER INFORMATION: Xaa = Gly or epsilon-amino caproic acid

<400> SEQUENCE: 53

Arg Xaa Xaa Arg Xaa Xaa Arg Xaa Xaa Arg Xaa Xaa Arg Xaa Xaa Arg
```

```
                 1               5                  10                  15

Xaa Xaa Arg

<210> SEQ ID NO 54
<211> LENGTH: 17
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid

<400> SEQUENCE: 54

Arg Xaa Xaa Xaa Arg Xaa Xaa Xaa Arg Xaa Xaa Xaa Arg Xaa Xaa Xaa
 1               5                  10                  15

Arg

<210> SEQ ID NO 55
<211> LENGTH: 21
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid

<400> SEQUENCE: 55

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg
            20
```

```
<210> SEQ ID NO 56
<211> LENGTH: 25
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (22)...(24)
<223> OTHER INFORMATION: Xaa = Gly, beta-alanine, gamma-amino butyric
      acid or epsilon-amino caproic acid

<400> SEQUENCE: 56

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg
                20                  25

<210> SEQ ID NO 57
<211> LENGTH: 29
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid
<220> FEATURE:
<221> NAME/KEY: MOD_RES
```

```
<222> LOCATION: (22)...(24)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (26)...(28)
<223> OTHER INFORMATION: Xaa = Gly, beta-alanine, gamma-amino butyric
      acid or epsilon-amino caproic acid

<400> SEQUENCE: 57

Arg Xaa Xaa Xaa Arg Xaa Xaa Xaa Arg Xaa Xaa Xaa Arg Xaa Xaa Xaa
 1               5                   10                  15

Arg Xaa Xaa Xaa Arg Xaa Xaa Xaa Arg Xaa Xaa Xaa Arg
            20                  25

<210> SEQ ID NO 58
<211> LENGTH: 33
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (22)...(24)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (26)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(32)
<223> OTHER INFORMATION: Xaa = Gly, beta-alanine, gamma-amino butyric
      acid or epsilon-amino caproic acid

<400> SEQUENCE: 58

Arg Xaa Xaa Xaa Arg Xaa Xaa Xaa Arg Xaa Xaa Xaa Arg Xaa Xaa Xaa
 1               5                   10                  15

Arg Xaa Xaa Xaa Arg Xaa Xaa Xaa Arg Xaa Xaa Xaa Arg Xaa Xaa Xaa
            20                  25                  30

Arg

<210> SEQ ID NO 59
<211> LENGTH: 37
<212> TYPE: PRT
<213> ORGANISM: Artificial Sequence
```

```
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (22)...(24)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (26)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(32)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (34)...(36)
<223> OTHER INFORMATION: Xaa = Gly, beta-alanine, gamma-amino butyric
      acid or epsilon-amino caproic acid

<400> SEQUENCE: 59

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg Xaa Xaa Xaa Arg Xaa Xaa Xaa
            20                  25                  30

Arg Xaa Xaa Xaa Arg
        35

<210> SEQ ID NO 60
<211> LENGTH: 41
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (2)...(4)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (6)...(8)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (10)...(12)
<223> OTHER INFORMATION: Xaa = Gly, beta-alanine, gamma-amino butyric
```

-continued

```
      acid or epsilon-amino caproic acid
<220> FEATURE:
<221> NAME/KEY: MOD_RES
<222> LOCATION: (14)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(20)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (22)...(24)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (26)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(32)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (34)...(36)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (38)...(40)
<223> OTHER INFORMATION: Xaa = Gly, beta-alanine, gamma-amino butyric
      acid or epsilon-amino caproic acid

<400> SEQUENCE: 60

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg Xaa Xaa Xaa Arg Xaa Xaa Xaa
                20                  25                  30

Arg Xaa Xaa Xaa Arg Xaa Xaa Xaa Arg
                35                  40

<210> SEQ ID NO 61
<211> LENGTH: 25
<212> TYPE: PRT
<213> ORGANISM: Artificial Sequence
<220> FEATURE:
<223> OTHER INFORMATION: delivery enhancing transporter moiety

<400> SEQUENCE: 61

Arg Gly Gly Gly Arg Gly Gly Gly Arg Gly Gly Gly Arg Gly Gly Gly
 1               5                  10                  15

Arg Gly Gly Gly Arg Gly Gly Gly Arg
                20                  25

<210> SEQ ID NO 62
<211> LENGTH: 33
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
```

```
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (24)...(33)
<223> OTHER INFORMATION: Xaa = any natural or non-natural amino acid,
      Xaa at positions 24-33 may be present or absent

<400> SEQUENCE: 62

Xaa Xaa Xaa Xaa Xaa Xaa Xaa Xaa Xaa Xaa Arg Xaa Xaa Arg Xaa Xaa
  1               5                  10                  15

Arg Xaa Xaa Arg Xaa Xaa Arg Xaa Xaa Xaa Xaa Xaa Xaa Xaa Xaa Xaa
             20                  25                  30

Xaa

<210> SEQ ID NO 63
<211> LENGTH: 36
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (27)...(36)
<223> OTHER INFORMATION: Xaa = any natural or non-natural amino acid,
      Xaa at positions 27-36 may be present or absent

<400> SEQUENCE: 63

Xaa Xaa Xaa Xaa Xaa Xaa Xaa Xaa Xaa Xaa Arg Xaa Xaa Arg Xaa Xaa
  1               5                  10                  15
```

```
Arg Xaa Xaa Arg Xaa Xaa Arg Xaa Xaa Arg Xaa Xaa Xaa Xaa Xaa
        20                  25                  30

Xaa Xaa Xaa Xaa
        35

<210> SEQ ID NO 64
<211> LENGTH: 39
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (27)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(39)
<223> OTHER INFORMATION: Xaa = any natural or non-natural amino acid,
      Xaa at positions 30-39 may be present or absent

<400> SEQUENCE: 64

Xaa Xaa Xaa Xaa Xaa Xaa Xaa Xaa Xaa Xaa Arg Xaa Xaa Arg Xaa Xaa
 1               5                  10                  15

Arg Xaa Xaa Arg Xaa Xaa Arg Xaa Xaa Arg Xaa Xaa Arg Xaa Xaa Xaa
        20                  25                  30

Xaa Xaa Xaa Xaa Xaa Xaa Xaa
        35

<210> SEQ ID NO 65
<211> LENGTH: 42
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
```

```
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (27)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(31)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (33)...(42)
<223> OTHER INFORMATION: Xaa = any natural or non-natural amino acid,
      Xaa at positions 33-42 may be present or absent

<400> SEQUENCE: 65

Xaa Xaa Xaa Xaa Xaa Xaa Xaa Xaa Xaa Xaa Arg Xaa Xaa Arg Xaa Xaa
 1               5                  10                  15

Arg Xaa Xaa Arg Xaa Xaa Arg Xaa Xaa Arg Xaa Xaa Arg Xaa Xaa Arg
            20                  25                  30

Xaa Xaa Xaa Xaa Xaa Xaa Xaa Xaa Xaa Xaa
        35                  40

<210> SEQ ID NO 66
<211> LENGTH: 45
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
```

```
       acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (27)...(28)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (30)...(31)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (33)...(34)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (36)...(45)
<223> OTHER INFORMATION: Xaa = any natural or non-natural amino acid,
       Xaa at positions 36-45 may be present or absent

<400> SEQUENCE: 66

Xaa Xaa Xaa Xaa Xaa Xaa Xaa Xaa Xaa Xaa Arg Xaa Xaa Arg Xaa Xaa
 1               5                  10                  15

Arg Xaa Xaa Arg Xaa Xaa Arg Xaa Xaa Arg Xaa Xaa Arg Xaa Xaa Arg
            20                  25                  30

Xaa Xaa Arg Xaa Xaa Xaa Xaa Xaa Xaa Xaa Xaa Xaa Xaa
        35                  40                  45

<210> SEQ ID NO 67
<211> LENGTH: 48
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
       Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
       acid or epsilon-amino caproic acid
<220> FEATURE:
<221> NAME/KEY: MOD_RES
<222> LOCATION: (27)...(28)
<223> OTHER INFORMATION: Xaa = Gly, beta-alanine, gamma-amino butyric
       acid or epsilon-amino caproic acid
```

```
<220> FEATURE:
<221> NAME/KEY: MOD_RES
<222> LOCATION: (30)...(31)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (33)...(34)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (36)...(37)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (39)...(48)
<223> OTHER INFORMATION: Xaa = any natural or non-natural amino acid,
      Xaa at positions 39-48 may be present or absent

<400> SEQUENCE: 67

Xaa Xaa Xaa Xaa Xaa Xaa Xaa Xaa Xaa Xaa Arg Xaa Xaa Arg Xaa Xaa
 1               5                  10                  15

Arg Xaa Xaa Arg Xaa Xaa Arg Xaa Xaa Arg Xaa Xaa Arg Xaa Xaa Arg
            20                  25                  30

Xaa Xaa Arg Xaa Xaa Arg Xaa Xaa Xaa Xaa Xaa Xaa Xaa Xaa Xaa
        35                  40                  45

<210> SEQ ID NO 68
<211> LENGTH: 51
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(10)
<223> OTHER INFORMATION: Xaa = any natural or non-natural amino acid,
      Xaa at positions 1-10 may be present or absent
<220> FEATURE:
<221> NAME/KEY: MOD_RES
<222> LOCATION: (12)...(13)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (15)...(16)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (18)...(19)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (21)...(22)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (24)...(25)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (27)...(28)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (30)...(31)
<223> OTHER INFORMATION: Xaa = Gly, beta-alanine, gamma-amino butyric
      acid or epsilon-amino caproic acid
<220> FEATURE:
```

```
<221> NAME/KEY: MOD_RES
<222> LOCATION: (33)...(34)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (36)...(37)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (39)...(40)
<223> OTHER INFORMATION: Xaa = Gly, beta-alanine, gamma-amino butyric
      acid or epsilon-amino caproic acid
<220> FEATURE:
<221> NAME/KEY: MOD_RES
<222> LOCATION: (42)...(51)
<223> OTHER INFORMATION: Xaa = any natural or non-natural amino acid,
      Xaa at positions 42-51 may be present or absent

<400> SEQUENCE: 68

Xaa Xaa Xaa Xaa Xaa Xaa Xaa Xaa Xaa Xaa Arg Xaa Xaa Arg Xaa Xaa
 1               5                   10                  15

Arg Xaa Xaa Arg Xaa Xaa Arg Xaa Xaa Arg Xaa Xaa Arg Xaa Xaa Arg
             20                  25                  30

Xaa Xaa Arg Xaa Xaa Arg Xaa Xaa Arg Xaa Xaa Xaa Xaa Xaa Xaa Xaa
         35                  40                  45

Xaa Xaa Xaa
    50

<210> SEQ ID NO 69
<211> LENGTH: 10
<212> TYPE: PRT
<213> ORGANISM: Artificial Sequence
<220> FEATURE:
<223> OTHER INFORMATION: delivery enhancing transporter moiety
<220> FEATURE:
<221> NAME/KEY: MOD_RES
<222> LOCATION: (1)...(1)
<223> OTHER INFORMATION: Xaa = N-acetyl cysteine
<220> FEATURE:
<221> NAME/KEY: MOD_RES
<222> LOCATION: (2)...(2)
<223> OTHER INFORMATION: Xaa = aminocaproic acid
<220> FEATURE:
<221> NAME/KEY: MOD_RES
<222> LOCATION: (10)...(10)
<223> OTHER INFORMATION: Xaa = argininamide

<400> SEQUENCE: 69

Xaa Xaa Arg Arg Arg Arg Arg Arg Arg Xaa
 1               5                   10

<210> SEQ ID NO 70
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = copper-diethylenetriaminepentaacetic acid
      complex (Cu-DTPA) linked to aminocaproic acid
      (aca)
<220> FEATURE:
<221> NAME/KEY: MOD_RES
<222> LOCATION: (8)...(8)
<223> OTHER INFORMATION: Xaa = Arg bound to peptide synthesizer solid-
      phase resin

<400> SEQUENCE: 70
```

```
Xaa Arg Arg Arg Arg Arg Arg Xaa
 1               5

<210> SEQ ID NO 71
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = diethylenetriaminepentaacetic acid (DTPA)
      linked to aminocaproic acid (aca)

<400> SEQUENCE: 71

Xaa Arg Arg Arg Arg Arg Arg Arg
 1               5

<210> SEQ ID NO 72
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = copper-diethylenetriaminepentaacetic acid
      complex (Cu-DTPA) linked to aminocaproic acid
      (aca)

<400> SEQUENCE: 72

Xaa Arg Arg Arg Arg Arg Arg Arg
 1               5

<210> SEQ ID NO 73
<211> LENGTH: 11
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = biotinylated aminocaproic acid (aca)
<220> FEATURE:
<221> NAME/KEY: MOD_RES
<222> LOCATION: (11)...(11)
<223> OTHER INFORMATION: Xaa = cysteinamide conjugated to hydrocortisone

<400> SEQUENCE: 73

Xaa Arg Arg Arg Arg Arg Arg Arg Ala Ala Xaa
 1               5                  10

<210> SEQ ID NO 74
<211> LENGTH: 7
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = Arg conjugated to benzyl (Bz) and acetyl
      (Ac) protected C-2' derivative of taxol through
      benzyl-(para-hydroxy benzoate) carbonate

<400> SEQUENCE: 74

Xaa Arg Arg Arg Arg Arg Arg
 1               5
```

-continued

```
<210> SEQ ID NO 75
<211> LENGTH: 7
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = Arg conjugated to benzyl (Bz) and acetyl
      (Ac) protected C-2' derivative of taxol through
      benzyl-(para-hydroxy benzoate) carbamate

<400> SEQUENCE: 75

Xaa Arg Arg Arg Arg Arg Arg
 1               5

<210> SEQ ID NO 76
<211> LENGTH: 6
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (6)...(6)
<223> OTHER INFORMATION: Xaa = argininamide

<400> SEQUENCE: 76

Xaa Arg Arg Arg Arg Xaa
 1               5

<210> SEQ ID NO 77
<211> LENGTH: 7
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (7)...(7)
<223> OTHER INFORMATION: Xaa = argininamide

<400> SEQUENCE: 77

Xaa Arg Arg Arg Arg Arg Xaa
 1               5

<210> SEQ ID NO 78
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (8)...(8)
<223> OTHER INFORMATION: Xaa = argininamide
```

-continued

```
<400> SEQUENCE: 78

Xaa Arg Arg Arg Arg Arg Xaa
 1               5

<210> SEQ ID NO 79
<211> LENGTH: 9
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (9)...(9)
<223> OTHER INFORMATION: Xaa = argininamide

<400> SEQUENCE: 79

Xaa Arg Arg Arg Arg Arg Arg Arg Xaa
 1               5

<210> SEQ ID NO 80
<211> LENGTH: 10
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (10)...(10)
<223> OTHER INFORMATION: Xaa = argininamide

<400> SEQUENCE: 80

Xaa Arg Arg Arg Arg Arg Arg Arg Arg Xaa
 1               5                  10

<210> SEQ ID NO 81
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (8)...(8)
<223> OTHER INFORMATION: Xaa = 6-maleimidocaproic hydrazone derivative of
      FK506 conjugated to Cys

<400> SEQUENCE: 81

Arg Arg Arg Arg Arg Arg Arg Xaa
 1               5

<210> SEQ ID NO 82
<211> LENGTH: 8
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (8)...(8)
<223> OTHER INFORMATION: Xaa = dithioethyl hydrazone derivative of FK506
      conjugated to Cys
```

```
<400> SEQUENCE: 82

Arg Arg Arg Arg Arg Arg Arg Xaa
1               5

<210> SEQ ID NO 83
<211> LENGTH: 7
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = biotinylated aminocaproic acid (aca)
<220> FEATURE:
<221> NAME/KEY: MOD_RES
<222> LOCATION: (7)...(7)
<223> OTHER INFORMATION: Xaa = cysteinamide

<400> SEQUENCE: 83

Xaa Arg Arg Arg Arg Arg Xaa
1               5

<210> SEQ ID NO 84
<211> LENGTH: 9
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = biotinylated aminocaproic acid (aca)
<220> FEATURE:
<221> NAME/KEY: MOD_RES
<222> LOCATION: (9)...(9)
<223> OTHER INFORMATION: Xaa = cysteinamide

<400> SEQUENCE: 84

Xaa Arg Arg Arg Arg Arg Arg Arg Xaa
1               5

<210> SEQ ID NO 85
<211> LENGTH: 11
<212> TYPE: PRT
<213> ORGANISM: Artificial Sequence
<220> FEATURE:
<223> OTHER INFORMATION: delivery enhancing transporter moiety conjugate
<220> FEATURE:
<221> NAME/KEY: MOD_RES
<222> LOCATION: (1)...(1)
<223> OTHER INFORMATION: Xaa = biotinylated aminocaproic acid (aca)
<220> FEATURE:
<221> NAME/KEY: MOD_RES
<222> LOCATION: (11)...(11)
<223> OTHER INFORMATION: Xaa = cysteinamide

<400> SEQUENCE: 85

Xaa Arg Arg Arg Arg Arg Arg Arg Arg Arg Xaa
1               5                   10

<210> SEQ ID NO 86
<211> LENGTH: 25
<212> TYPE: PRT
<213> ORGANISM: Artificial Sequence
<220> FEATURE:
<223> OTHER INFORMATION: Description of Artificial
      Sequence:delivery-enhancing transporter polymer of
      poly-arginine molecules between 6 and 25 residues
      in length
<220> FEATURE:
<221> NAME/KEY: MOD_RES
```

```
<222> LOCATION: (7)..(25)
<223> OTHER INFORMATION: Arg at positions 7-25 may be present or absent

<400> SEQUENCE: 86

Arg Arg Arg Arg Arg Arg Arg Arg Arg Arg Arg Arg Arg Arg Arg
 1               5                  10                  15

Arg Arg Arg Arg Arg Arg Arg Arg Arg
            20                  25
```

COMPOSITIONS AND METHODS FOR ENHANCING DRUG DELIVERY ACROSS AND INTO OCULAR TISSUES

CROSS-REFERENCE TO RELATED APPLICATIONS

This application is a continuation of U.S. patent application Ser. No. 11/800,358, filed May 4, 2007, now U.S. Pat. No. 8,278,264, which is a continuation of U.S. patent application Ser. No. 10/083,960, filed Feb. 25, 2002, now U.S. Pat. No. 7,229,961, which is a continuation-in-part application of U.S. patent application Ser. No. 09/792,480, filed on Feb. 23, 2001, now U.S. Pat. No. 6,669,951, which is a continuation-in-part application of U.S. patent application Ser. No. 09/648,400, filed on Aug. 24, 2000, now U.S. Pat. No. 6,593,292, which claims priority to U.S. Provisional Patent Application No. 60/150,510, filed Aug. 24, 1999, now abandoned. All of these applications are incorporated herein by reference for all purposes in their entireties.

BACKGROUND OF THE INVENTION

1. Field of the Invention

This invention pertains to the field of compositions and methods that enhance the delivery of drugs and other compounds across ocular epithelial and endothelial tissues as well as other tissues in the eye and eye lid.

2. Background

Administration of drugs for treatment of the eye fall into at least three categories: topical administration, injection and systemic administration.

Eye drops and ointments have been used over many years to treat a vast number of ocular disorders and diseases. However, topical administration is not always effective because of the eye's natural protective surface. In many circumstances, less than one percent or less of the active agent is delivered to the target site.

Ocular injection can be effective to deliver a higher concentration of the active agent to the target. Sometimes it can be difficult to accurately inject a drug to the correct site in the eye.

Systemic administration may be used to deliver agents to the eye, but requires high doses because so little of the administrated compound actually enters the eye.

The present invention addresses these and other problems.

SUMMARY OF THE INVENTION

The delivery-enhancing transporters and methods of the invention are useful for delivering drugs, diagnostic agents, and other compounds of interest to the eye and other ocular tissues. In some embodiments, the methods involve administering to an ocular tissue a conjugate that comprises the compound and a delivery-enhancing transporter. The delivery-enhancing transporters, which are also provided by the invention, have sufficient guanidino or amidino moieties to increase delivery of the conjugate into the ocular tissue compared to delivery of the compound in the absence of the delivery-enhancing transporter. In some embodiments, delivery of the conjugate into the ocular tissue is increased at least two-fold compared to delivery of the compound in the absence of the delivery-enhancing transporter. In some embodiments, delivery of the conjugate into the ocular tissue is increased at least ten-fold compared to delivery of the compound in the absence of the delivery-enhancing transporter. In some embodiments, the ocular tissue is an ocular epithelial or endothelial tissue. In some embodiments, the ocular tissue is the retina or the optic nerve.

The delivery-enhancing transporter and the compound are typically attached through a linker. In addition, the conjugate can comprise two or more delivery-enhancing transporters linked to the compound.

Typically, the delivery-enhancing transporters comprise fewer than 50 subunits and comprise at least 6 guanidino or amidino moieties. In some embodiments, the subunits are amino acids. In some embodiments, the delivery-enhancing transporters have from 6 to 25 guanidino or amidino moieties, and more preferably between 7 and 15 guanidino moieties and still more preferably, at least six contiguous guanidino and/or amidino moieties. In some embodiments, the delivery-enhancing transporters consist essentially of 5 to 50 subunits, at least 50 of which comprise guanidino or amidino residues. In some of these embodiments, the subunits are natural or non-natural amino acids. For example, in some embodiments, the delivery-enhancing transporter comprises 5 to 25 arginine residues or analogs thereof. For example, the transporter can comprise seven contiguous D-arginines.

In some embodiments, the delivery-enhancing transporter comprises 7-15 arginine residues or analogs of arginine. The delivery-enhancing transporter can have at least one arginine that is a D-arginine and in some embodiments, all arginines are D-arginine. In some embodiments, at least 70% of the amino acids are arginines or arginine analogs. In some embodiments, the delivery-enhancing transporter comprises at least 5 contiguous arginines or arginine analogs. The delivery-enhancing transporters can comprise non-peptide backbones. In addition, in some aspects, the transporter is not attached to an amino acid sequence to which the delivery-enhancing molecule is attached in a naturally occurring protein.

In some embodiments, the conjugate is administered as eye drops or as an injection. The compounds of the conjugate include therapeutics for a disease selected from the group consisting of bacterial infections, viral infections, fungal infections, glaucoma, anterior, intermediate, and posterior uveitis, optic neuritis, Leber's neuroretinitis, retinitis, psudotumor/myositis, orbital myositis, hemangioma/lymphangioma, toxocariasis, Behcet's panuveitis, inflammatory chorisretinopathies, vasculitis, dry eye syndrome (Sjogren's syndrome), corneal edema, accommodative esotropia, cycloplegia, mydriasis, reverse mydriasis, and macular degeneracy. In some embodiments, the compound is selected from the group consisting of anti-bacterial compounds, antiviral compounds, anti-fungal compounds, anti-protozoan compounds, anti-histamines, compounds that dialate the pupil, anethstetic compounds, steroidal antiinflammatory agents, antiinflammatory analgesics, chemotherapeutic agents, hormones, anticataract agents, neovascularization inhibitors, immunosuppressants, protease inhibitors, aldose reductase inhibitors, corticoid steroids, immunosuppressives, cholinergic agents, anticholinesterase agents, muscaric antagonists, sympathomimetic agents, α and β adrenergic antagonists, and anti-angiogenic factors. Thus, the compounds can include antibacterial compounds, antiviral compounds, cyclosporin, ascomycins and corticosteroids. In some embodiments, the compound is selected from the group consisting of acyclovir and cyclosporins.

As discussed above, the compound to be delivered can be connected to the delivery-enhancing transporter by a linker. In some embodiments, the linker is a releasable linker which releases the compound, in biologically active form, from the delivery-enhancing transporter after the compound has passed into and/or through one or more layers of the epithelial and/or endothelial tissue. In some embodiments, the compound is released from the linker by solvent-mediated cleavage. The conjugate is, in some embodiments, substantially stable at acidic pH but the compound is substantially released from the delivery-enhancing transporter at physiological pH. In some embodiments, the half-life of the conjugate is between 5 minutes and 24 hours upon contact with the skin or other epithelial or endothelial tissue. For example, the half-life can be between 30 minutes and 2 hours upon contact with the skin or other epithelial or endothelial tissue. In some embodiments, the linker is stable in a saline solution a pH 7 but is cleaved when transported into a cell.

Examples of conjugate structures of the invention include those having structures such as 3, 4, or 5, as follows:

3

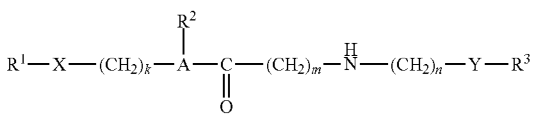

4

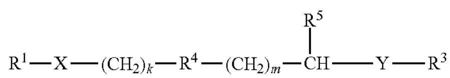

5

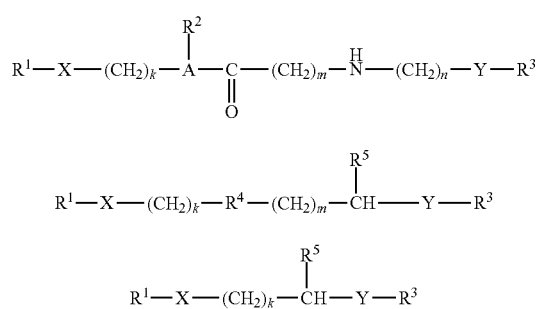

wherein $R^1$ comprises the compound; X is a linkage formed between a functional group on the biologically active compound and a terminal functional group on the linking moiety; Y is a linkage formed from a functional group on the transport moiety and a functional group on the linking moiety; A is N or CH; $R^2$ is hydrogen, alkyl, aryl, acyl, or allyl; $R^3$ comprises the delivery-enhancing transporter; $R^4$ is S, O, $NR^6$ or $CR^7R^8$; $R^5$ is H, OH, SH or $NHR^6$; $R^6$ is hydrogen, alkyl, aryl, acyl or allyl; k and m are each independently selected from 1 and 2; and n is 1 to 10.

Preferably, X is selected from the group consisting of —C(O)O—, —C(O)NH—, —OC(O)NH—, —S—S—, —C(S)O—, —C(S)NH—, —NHC(O)NH—, —$SO_2$NH—, —SONH—, phosphate, phosphonate phosphinate, and $CR^7R^8$, wherein $R^7$ and $R^8$ are each independently selected from the group consisting of H and alkyl. In some embodiments, $R_4$ is S; $R_5$ is $NHR_6$; and $R_6$ is hydrogen, methyl, allyl, butyl or phenyl. In some embodiments, $R_2$ is benzyl; k, m, and n are each 1, and X is O. In some embodiments, the conjugate comprises structure 3, Y is N, and $R^2$ is methyl, ethyl, propyl, butyl, allyl, benzyl or phenyl. In some embodiments, $R^2$ is benzyl; k, m, and n are each 1, and X is —OC(O)—. In some embodiments, the conjugate comprises structure 4; $R^4$ is S; $R^5$ is $NHR^6$; and $R^6$ is hydrogen, methyl, allyl, butyl or phenyl. In some embodiments, the conjugate comprises structure 4; $R^5$ is $NHR^6$; $R^6$ is hydrogen, methyl, allyl, butyl or phenyl; and k and m are each 1.

The invention also provides conjugates in which the release of the linker from the biological agent involves a first, rate-limiting intramolecular reaction, followed by a faster intramolecular reaction that results in release of the linker. The rate-limiting reaction can, by appropriate choice of substituents of the linker, be made to be stable at a pH that is higher or lower than physiological pH. However, once the conjugate has passed into and across one or more layers of an epithelial or endothelial tissue, the linker will be cleaved from the agent. An example of a compound that has this type of linker is structure 6, as follows:

6 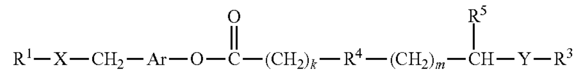 wherein $R^1$ comprises the compound; X is a linkage formed between a functional group on the biologically active compound and a terminal functional group on the linking moiety; Y is a linkage formed from a functional group on the transport moiety and a functional group on the linking moiety; Ar is an aryl group having the attached radicals arranged in an ortho or para configuration, which aryl group can be substituted or unsubstituted; $R^3$ comprises the delivery-enhancing transporter; $R^4$ is S, O, $NR^6$ or $CR^7R^8$; $R^5$ is H, OH, SH or $NHR_6$; $R^6$ is hydrogen, alkyl, aryl, arylalkyl, acyl or allyl; $R^7$ and $R^8$ are independently selected from hydrogen or alkyl; and k and m are each independently selected from 1 and 2.

In some embodiments, X is selected from the group consisting of —C(O)O—, —C(O)NH—, —OC(O)NH—, —S—S—, —C(S)O—, —C(S)NH—, —NHC(O)NH—, —$SO_2$NH—, —SONH—, phosphate, phosphonate phosphinate, and $CR^7R^8$, wherein $R^7$ and $R^8$ are each independently selected from the group consisting of H and alkyl. In some embodiments, $R^4$ is S; $R^5$ is $NHR^6$; and $R^6$ is hydrogen, methyl, allyl, butyl or phenyl.

In preferred embodiments, the compositions of the invention comprise a linker susceptible to solvent-mediated cleavage. For example, a preferred linker is substantially stable at acidic pH but is substantially cleaved at physiological pH. In some embodiments, the linker is stable in a saline solution such as PBS. In some embodiments, the linker is stable in a saline solution but is cleaved when transported into a cell.

BRIEF DESCRIPTION OF THE FIGURES

FIG. 1 shows a reaction scheme for the preparation of an α-chloroacetyl cyclosporin A derivative.

FIG. 2 shows a general procedure for the coupling of cysteine-containing peptides to the α-chloro acetyl cyclosporin A derivative.

FIG. 3 shows a reaction scheme for the coupling of the cyclosporin A derivative to a biotin-labeled peptide (SEQ ID NOS:83-85).

FIG. 4 shows a reaction scheme for coupling of a cyclosporin A derivative to an unlabeled peptide (SEQ ID NO:7).

FIG. 5A-H show various types of cleavable linkers that can be used to link a delivery-enhancing transporter to a biologically active agent or other molecule of interest. FIG. 5A shows an example of a disulfide linkage. FIG. 5B shows a photocleavable linker which is cleaved upon exposure to electromagnetic radiation. FIG. 5C shows a modified lysyl residue used as a cleavable linker. FIG. 5D shows a conjugate in which the delivery-enhancing transporter T is linked to the 2'-oxygen of the anticancer agent, paclitaxel. The linking moiety includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. FIG. 5E a linkage of a delivery-enhancing transporter to a biologically active agent, e.g., paclitaxel, by an aminoalkyl carboxylic acid; a linker amino group is joined to a delivery-enhancing transporter by an amide linkage and to a paclitaxel moiety by an ester linkage. FIGS. 5F and G show chemical structures and conventional numbering of constituent backbone atoms for paclitaxel and "TAXOTERE™" (R'=H, R"=BOC). FIG. 5H shows the general chemical structure and ring atom numbering for taxoid compounds.

FIG. 6 displays a synthetic scheme for a chemical conjugate between a heptamer of L-arginine (SEQ ID NO:3) and cyclosporin A (panel A) and its pH dependent chemical release (SEQ ID NO:6) (panel B). The α-chloro ester (6i) was treated with benzylamine in the presence of sodium iodide to effect substitution, giving the secondary amine (6ii). Amine (6ii) was treated with anhydride (6) and the resultant crude acid (6iii) was converted to its corresponding NHS ester (6iv). Ester (6iv) was then coupled with the amino terminus of hepta-L-arginine (SEQ ID NO:3), giving the N-Boc protected CsA conjugate (6v). Finally, removal of the Boc protecting group with formic acid afforded the conjugate (6vi) as its octatrifluoroacetate salt after HPLC purification.

FIG. 7 displays inhibition of inflammation in murine contact dermatitis by releasable R7 CsA. Balb/c (6-7 weeks) mice were painted on the abdomen with 100 μl of 0.7% DNFB in acetone olive oil (95:5). Three days later both ears of the animals were restimulated with 0.5% DNFB in acetone. Mice were treated one, five, and twenty hours after restimulation with either vehicle alone, 1% R7 (SEQ ID NO:3) peptide alone, 1% CsA, 1% nonreleasable R7 CsA, 0.01%/0.1%/1.0% releasable R7 CsA, and the fluorinated steroid positive control 0.1% triamcinolone acetonide. Ear inflammation was measured 24 hours after restimulation using a spring loaded caliper. The percent reduction of inflammation was calculated using the following formula (t−n)/(u−n), where t=thickness of the treated ear, n=the thickness of a normal untreated ear, and u=thickness of an inflamed ear without any treatment. N=20 animals in each group.

Figure 15A:
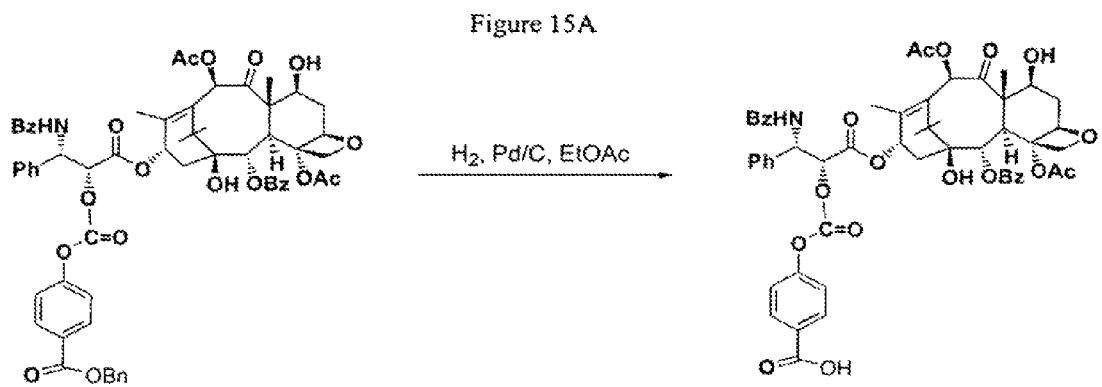
Figure 15B:
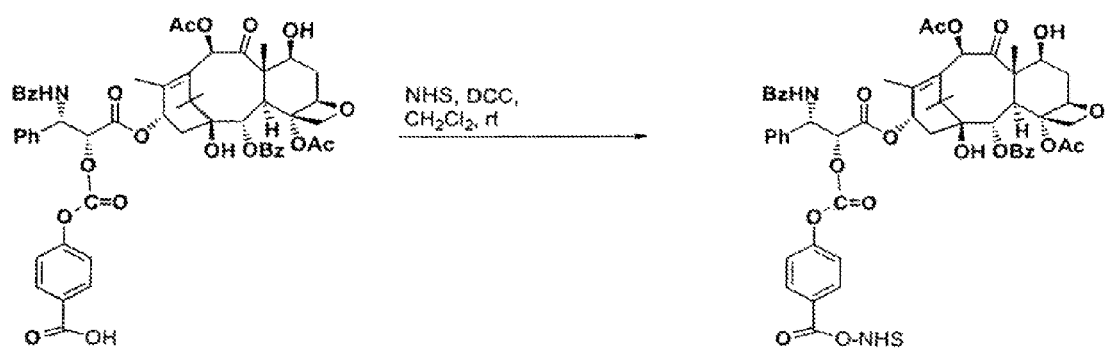
Figure 15C:
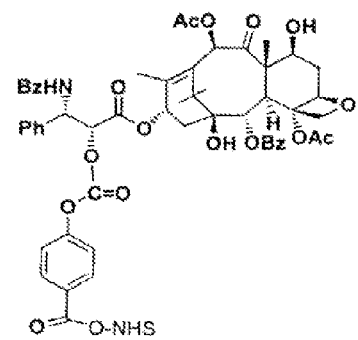
Figure 15C:
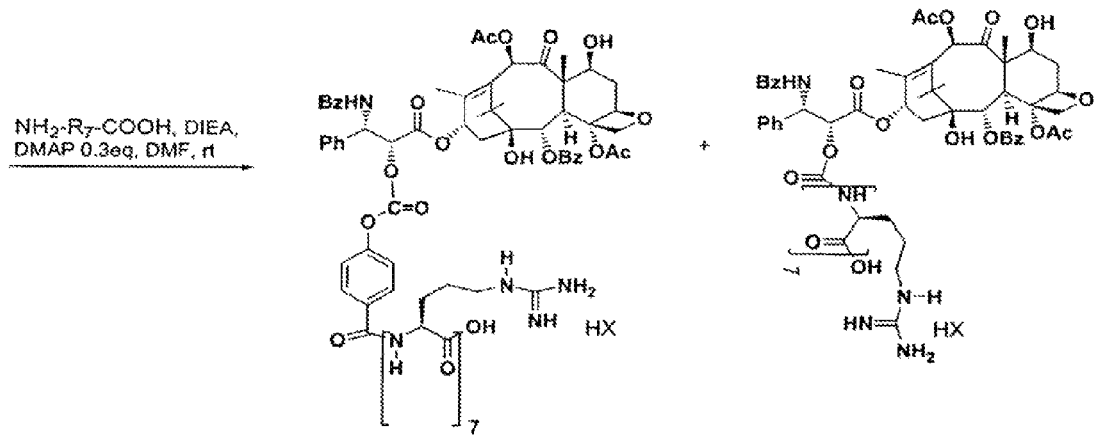

FIG. 15A-C shows a reaction scheme for the formation of other C-2' taxol-peptide conjugates (SEQ ID NOS:3, 74 and 75).

Figure 16:
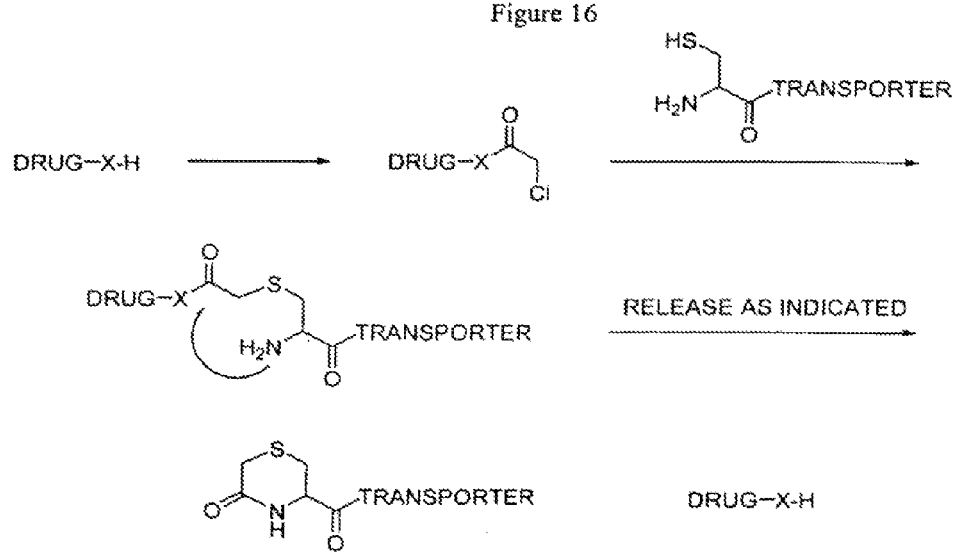

FIG. 16 shows a general strategy for synthesis of a conjugate in which a drug or other biological agent is linked to a delivery-enhancing transporter by a pH-releasable linker.

Figure 17:
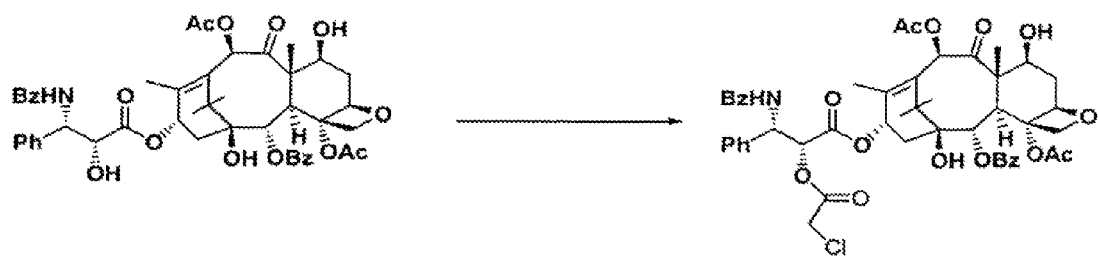

FIG. 17 shows a schematic diagram of a protocol for synthesizing a taxol 2'-chloroacetyl derivative.

Figure 18:
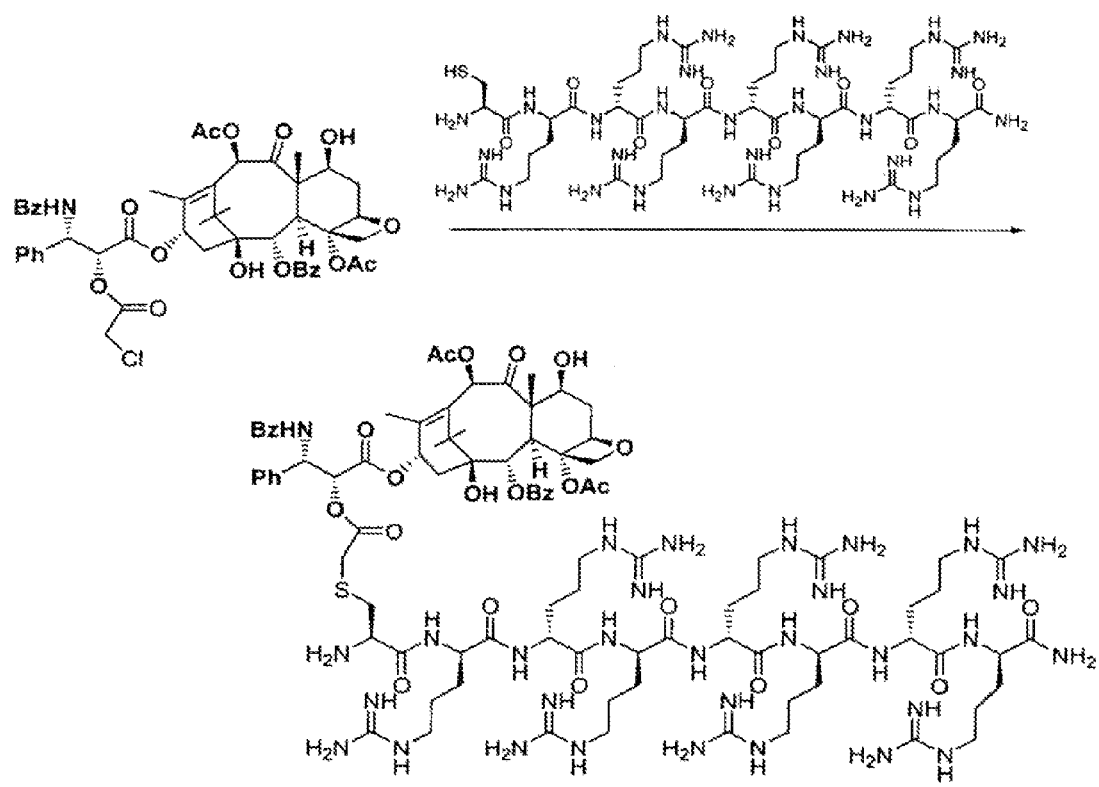

FIG. 18 shows a strategy by which a taxol 2'-chloroacetyl derivative is linked to an arginine heptamer delivery-enhancing transporter.

Figure 19:
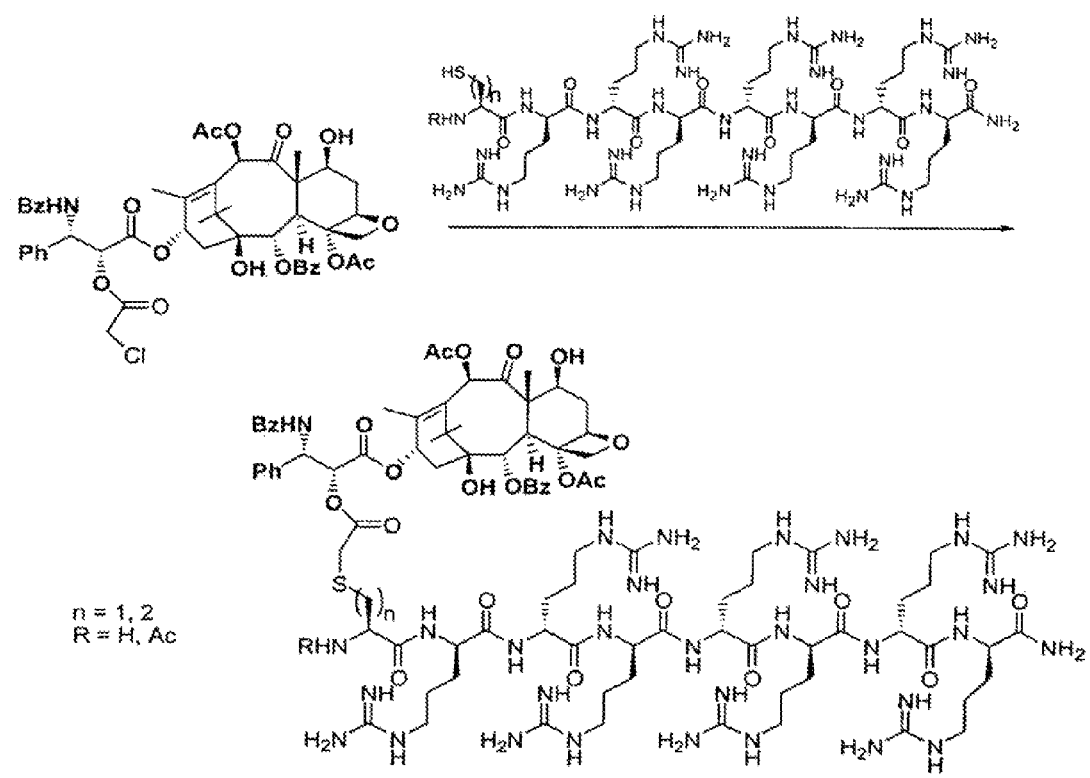

FIG. 19 shows three additional taxol-r7 conjugates that can be made using the reaction conditions illustrated in FIG. 18.

Figure 20:
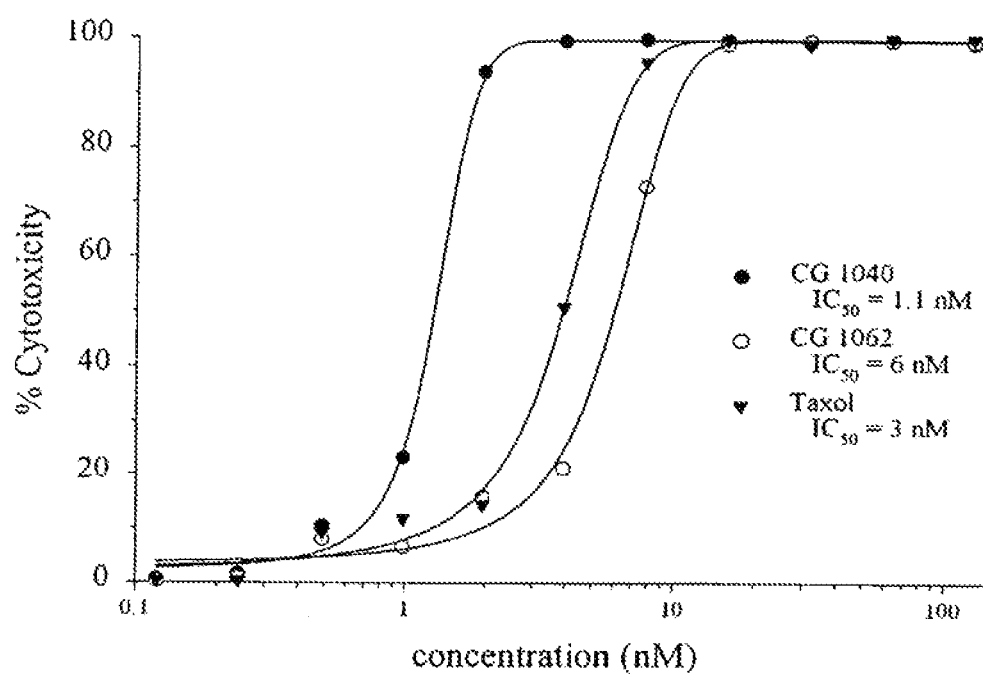

FIG. 20 shows the results of a 3 day MTT cytotoxicity assay using taxol and two different linkers.

Figure 21:
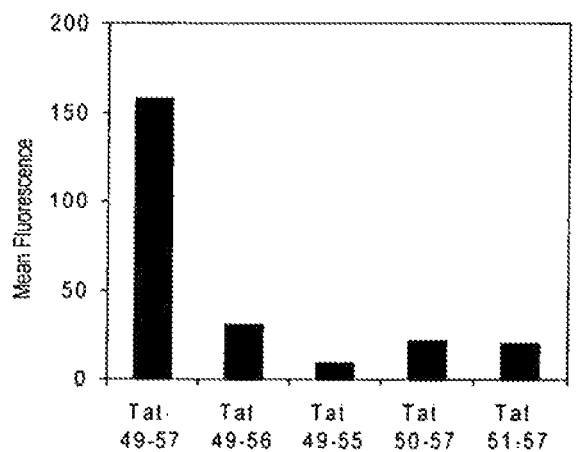

FIG. 21 shows the FACS cellular uptake assay of truncated analogs of Tat$_{49-75}$ (Fl-ahx-RKKRRQRRR; SEQ ID NO:8): Tat$_{49-56}$ (Fl-ahx-RKKRRQRR; SEQ ID NO:9), Tat$_{49-55}$ (Fl-ahx-RKKRRQR; SEQ ID NO:10), Tat$_{50-57}$ (Fl-ahx-KKRRQRRR; SEQ ID NO:11), and Tat$_{51-57}$ (Fl-ahx-KRRQRRR; SEQ ID NO:12). Jurkat cells were incubated with varying concentrations (12.5 μM shown) of peptides for 15 min at 23° C.

Figure 22:
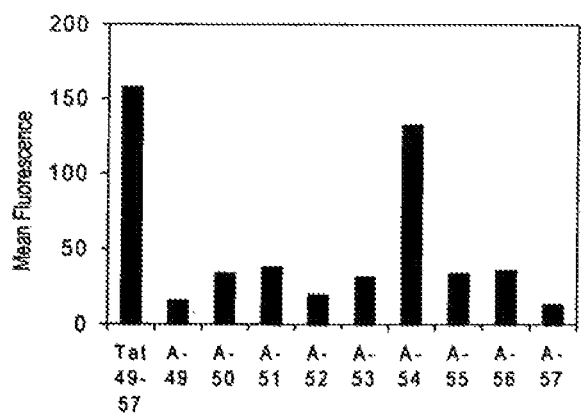

FIG. 22 shows FACS cellular uptake assay of alanine-substituted analogs of Tat$_{49-57}$: A-49 (Fl-ahx-AKKRRQRRR; SEQ ID NO:13), A-50 (Fl-ahx-RAKRRQRRR; SEQ ID NO:14), A-51 (Fl-ahx-RKARRQRRR; SEQ ID NO:15), A-52 (Fl-ahx-RKKARQRRR; SEQ ID NO:16), A-53 (Fl-ahx-RKKRAQRRR; SEQ ID NO:17), A-54 (Fl-ahx-RKKRRARRR; SEQ ID NO:18), A-55 (Fl-ahx-RKKRRQARR; SEQ ID NO:19), A-56 (Fl-ahx-RKKRRQRRR; SEQ ID NO:20), and A-57 (Fl-ahx-RKKRRQRRA; SEQ ID NO:21). Jurkat cells were incubated with varying concentrations (12.5 μM shown) of peptides for 12 min at 23° C.

Figure 23:
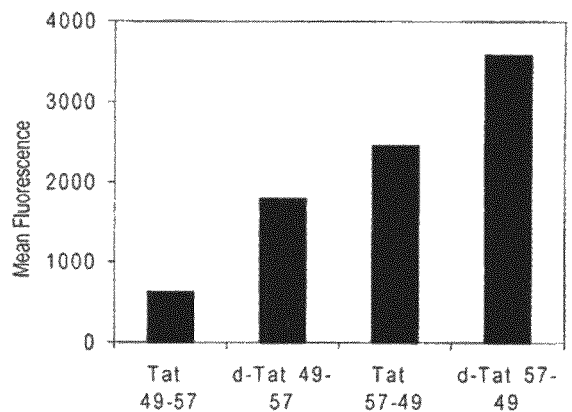

FIG. 23 shows the FACS cellular uptake assay of d- and retro-isomers of Tat$_{49-57}$: d-Tat49-57 (Fl-ahx-rkkrrqrrr), Tat57-49 (Fl-ahx-RRRQRRKKR; SEQ ID NO:22), and d-Tat57-49 (Fl-ahx-rrrqrrkkr). Jurkat cells were incubated with varying concentrations (12.5 μM shown) of peptides for 15 min at 23° C.

Figure 24:
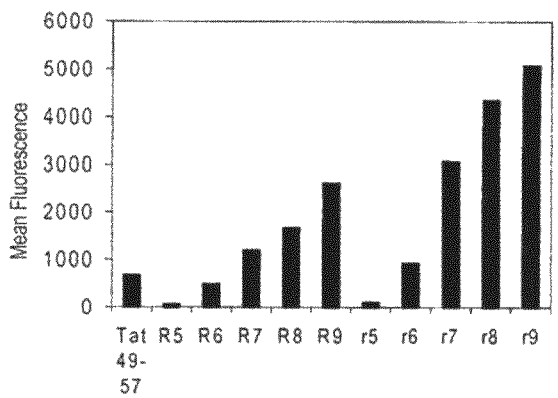

FIG. 24 shows the FACS cellular uptake of a series of arginine oligomers and Tat$_{49-57}$: R5 (Fl-ahx-RRRRR; SEQ ID NO:23), R6 (Fl-ahx-RRRRRR; SEQ ID NO:24), R7 (Fl-ahx-RRRRRRR; SEQ ID NO:25), R8 (Fl-ahx-RRRRRRRR; SEQ ID NO:26), R9 (Fl-ahx-RRRRRRRRR; SEQ ID NO:27), r5 (Fl-ahx-rrrrr), r6 (Fl-ahx-rrrrrr), r7 (Fl-ahx-rrrrrrr), r8 (Fl-ahx-rrrrrrrr), r9 (Fl-ahx-rrrrrrrrr). Jurkat cells were incubated with varying concentrations (12.5 μM shown) of peptides for 4 min at 23° C.

Figure 25:
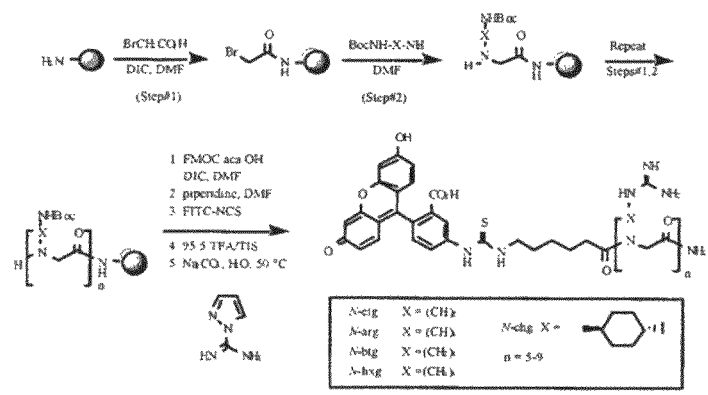

FIG. 25 displays the preparation of guanidine-substituted peptoids (SEQ ID NOS:76-89).

Figure 26:
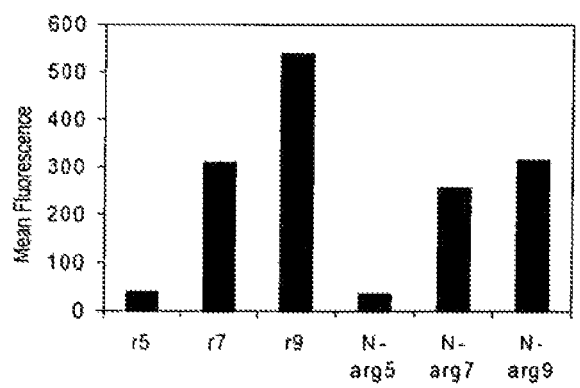

FIG. 26 displays the FACS cellular uptake of polyguanidine peptoids (SEQ ID NOS:76, 78 and 80) and d-arginine oligomers. Jurkat cells were incubated with varying concentrations (12.5 μM shown) of peptoids and peptides for 4 min at 23° C.

Figure 27:
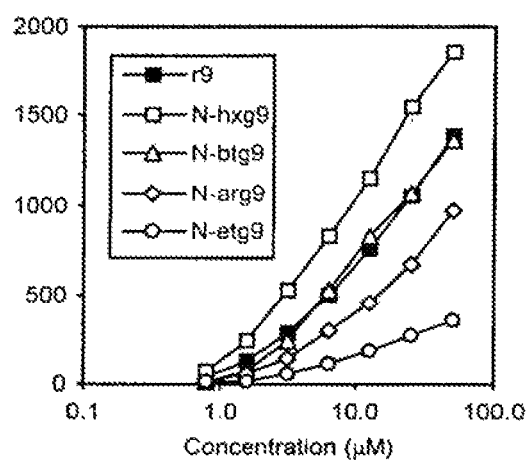

FIG. 27 displays the FACS cellular uptake of d-arginine oligomers and polyguanidine peptoids. Jurkat cells were incubated with varying concentrations (12.5 μM shown) of fluorescently labeled peptoids and peptides for 4 min at 23° C.

Figure 28:
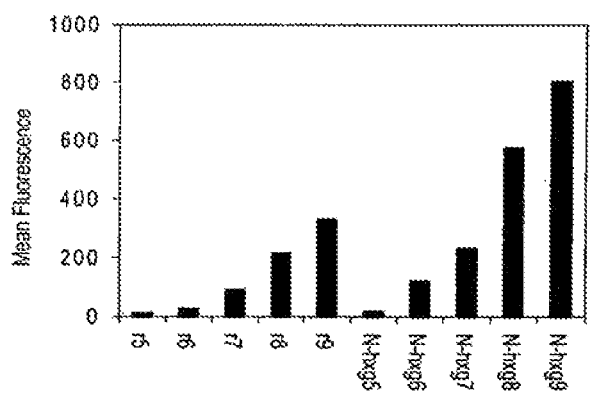

FIG. 28 displays the FACS cellular uptake of and d-arginine oligomers and N-hxg peptoids. Jurkat cells were incubated with varying concentrations (6.3 μM shown) of fluorescently labeled peptoids and peptides for 4 min at 23° C.

Figure 29:
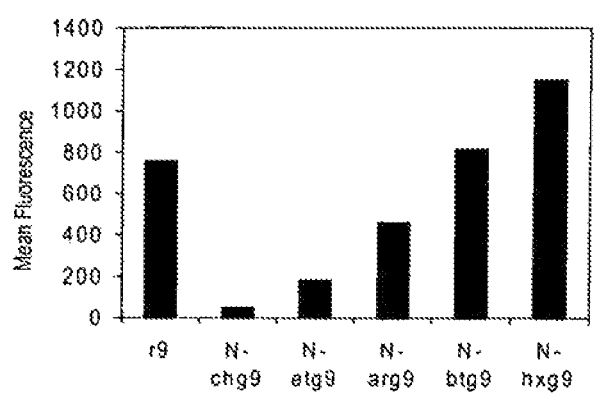

FIG. 29 shows the FACS cellular uptake of d-arginine oligomers and N-chg peptoids. Jurkat cells were incubated with varying concentrations (12.5 μM shown) of fluorescently labeled peptoids and peptides for 4 min at 23° C.

Figure 30:
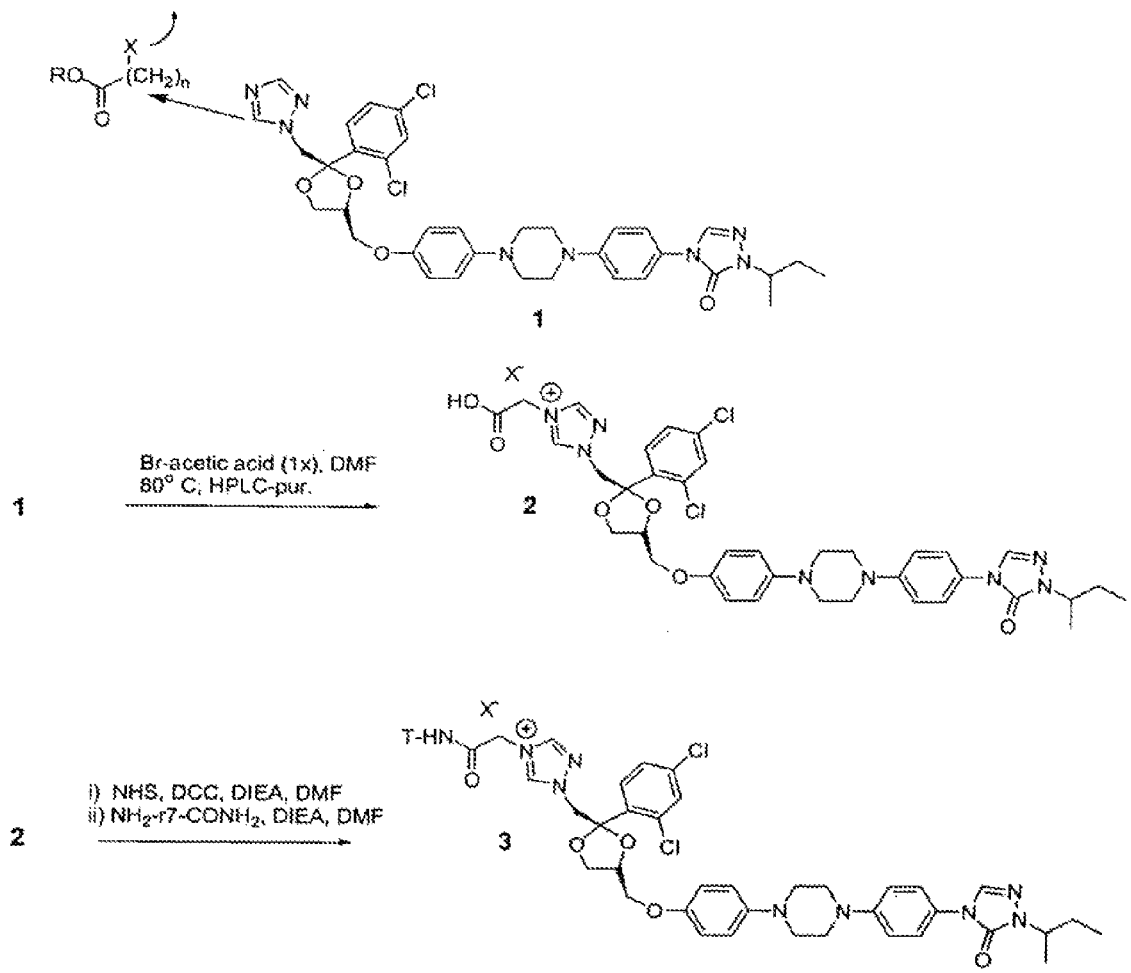

FIG. 30 shows a general strategy for attaching a delivery-enhancing transporter to a drug that includes a triazole ring structure.

Figure 31A:
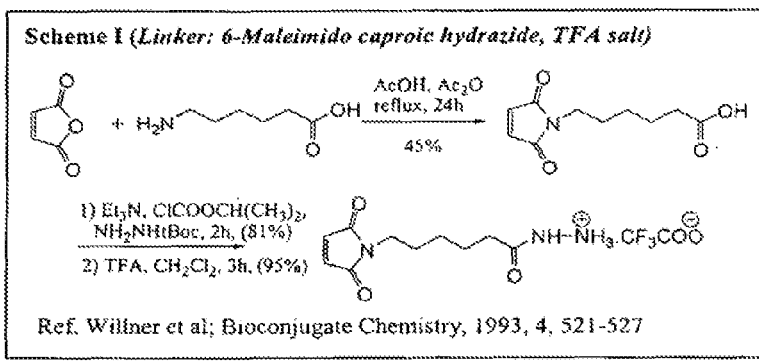
Figure 31A:
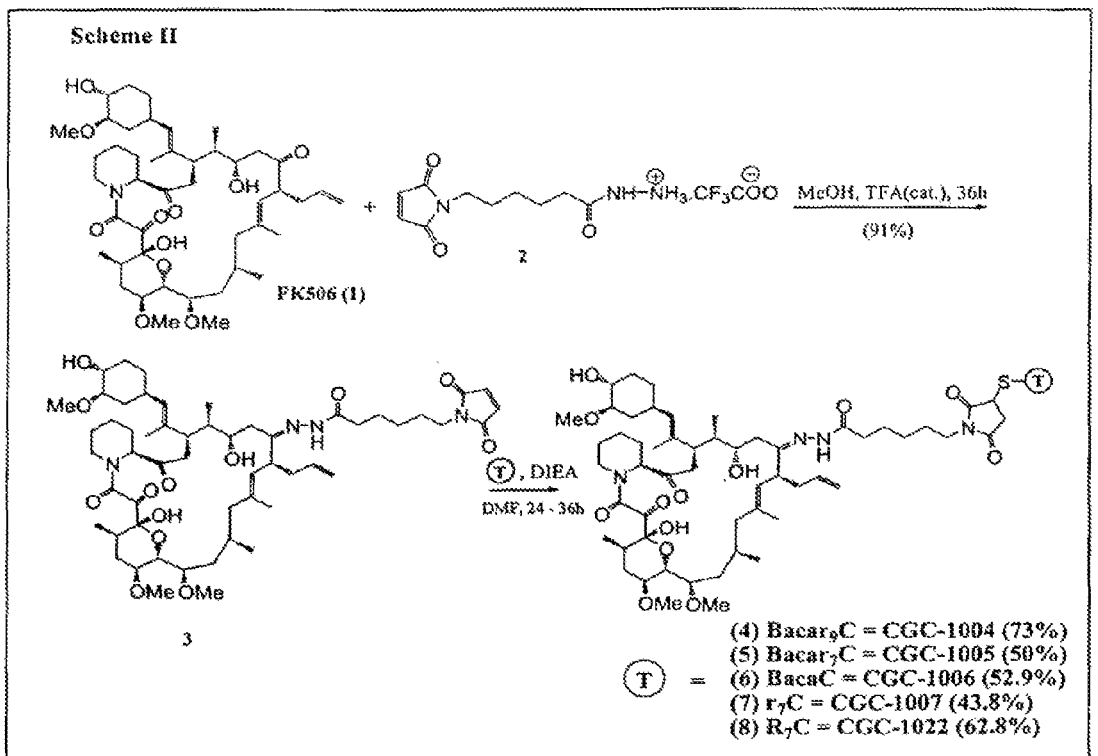
Figure 31B:
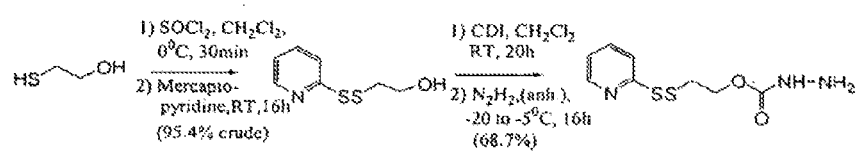
Figure 31B:
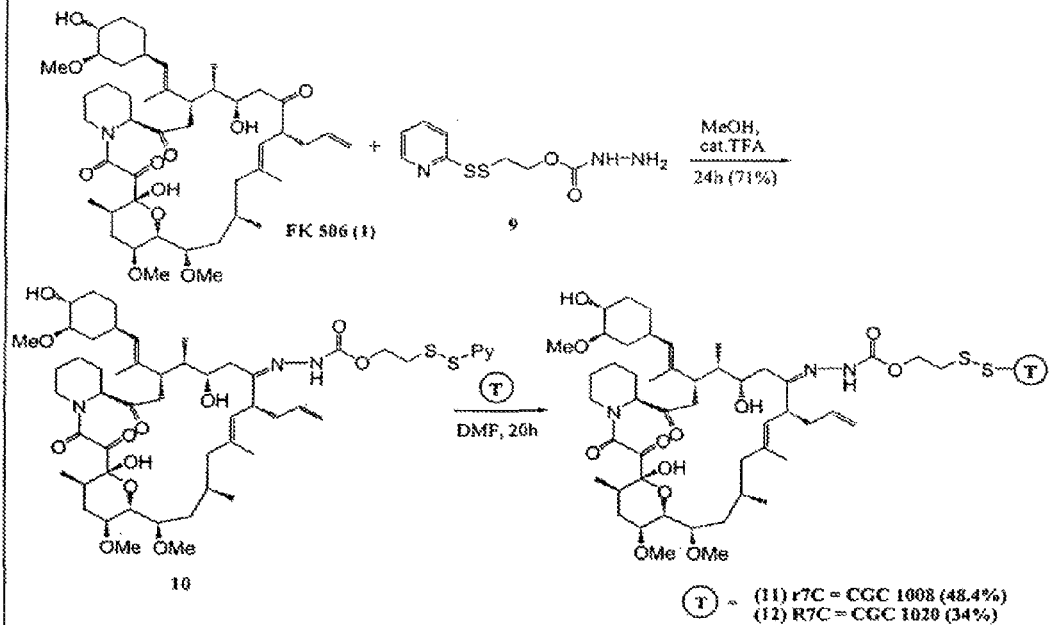

FIG. 31A and FIG. 31B show synthetic schemes for making conjugates in which FK506 is attached to a delivery-enhancing transporter (SEQ ID NOS:81 and 82).

Figure 32:
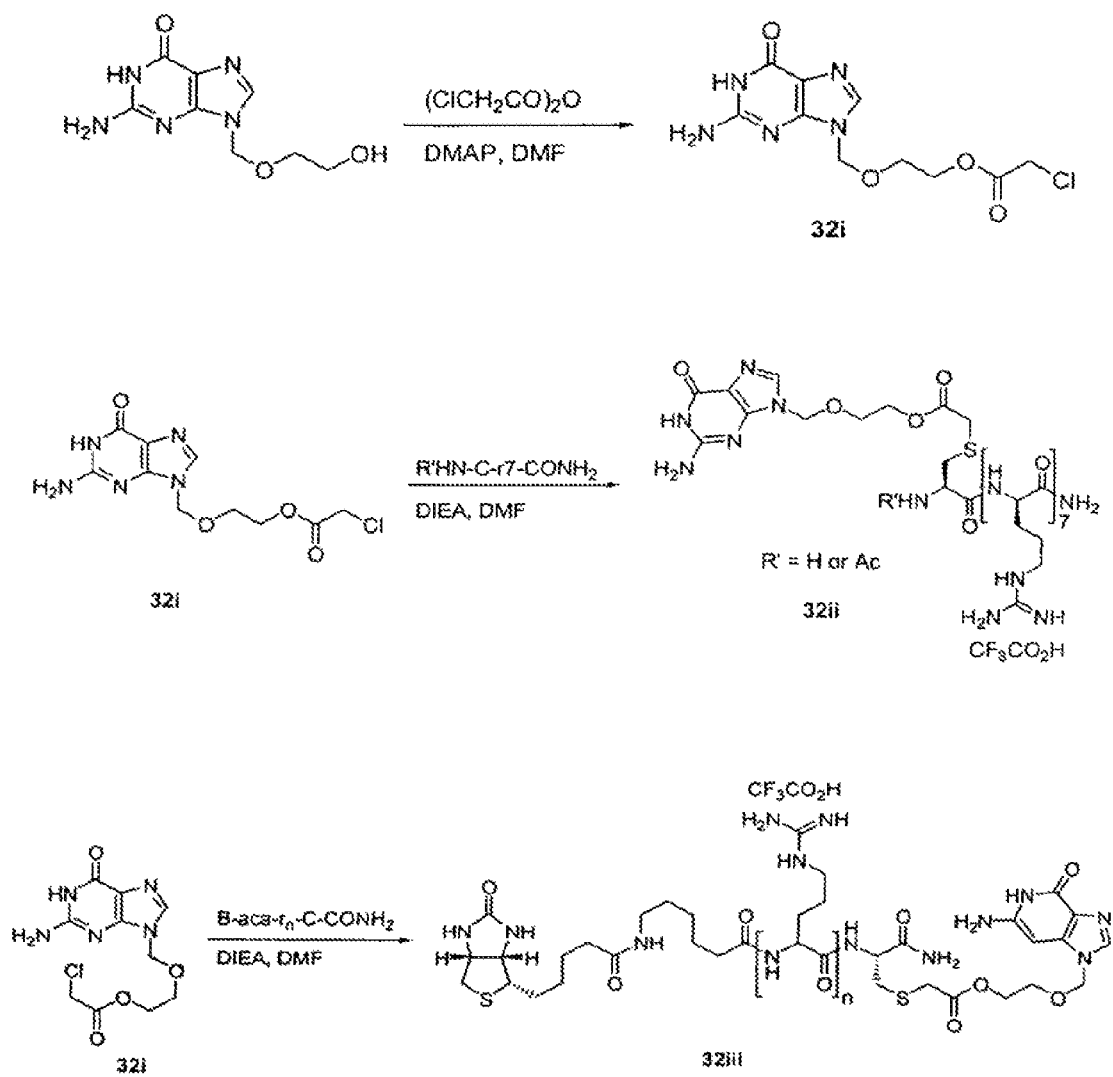

FIG. 32 illustrates the conjugation of acyclovir to r7-amide via an N-terminal cysteine group. Conjugation with a biotin-containing transporter is also shown.

Figure 33:
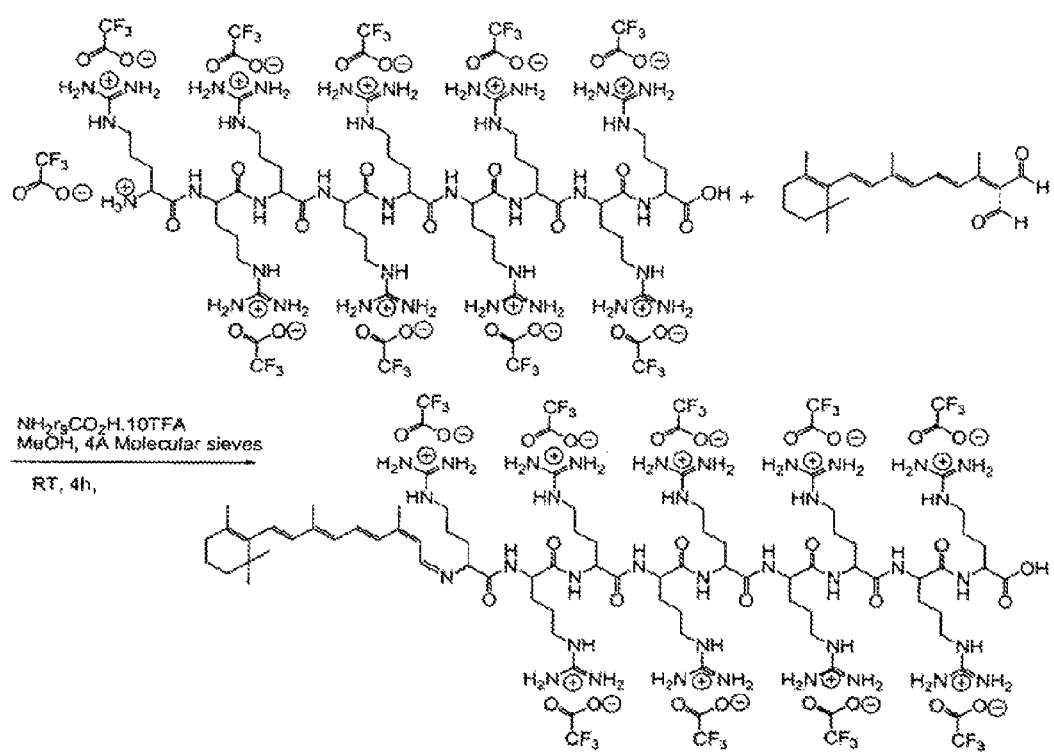

FIG. 33 illustrates the conjugate formed between a retinal and a r9 (shown without spacing amino acids).

Figure 34:
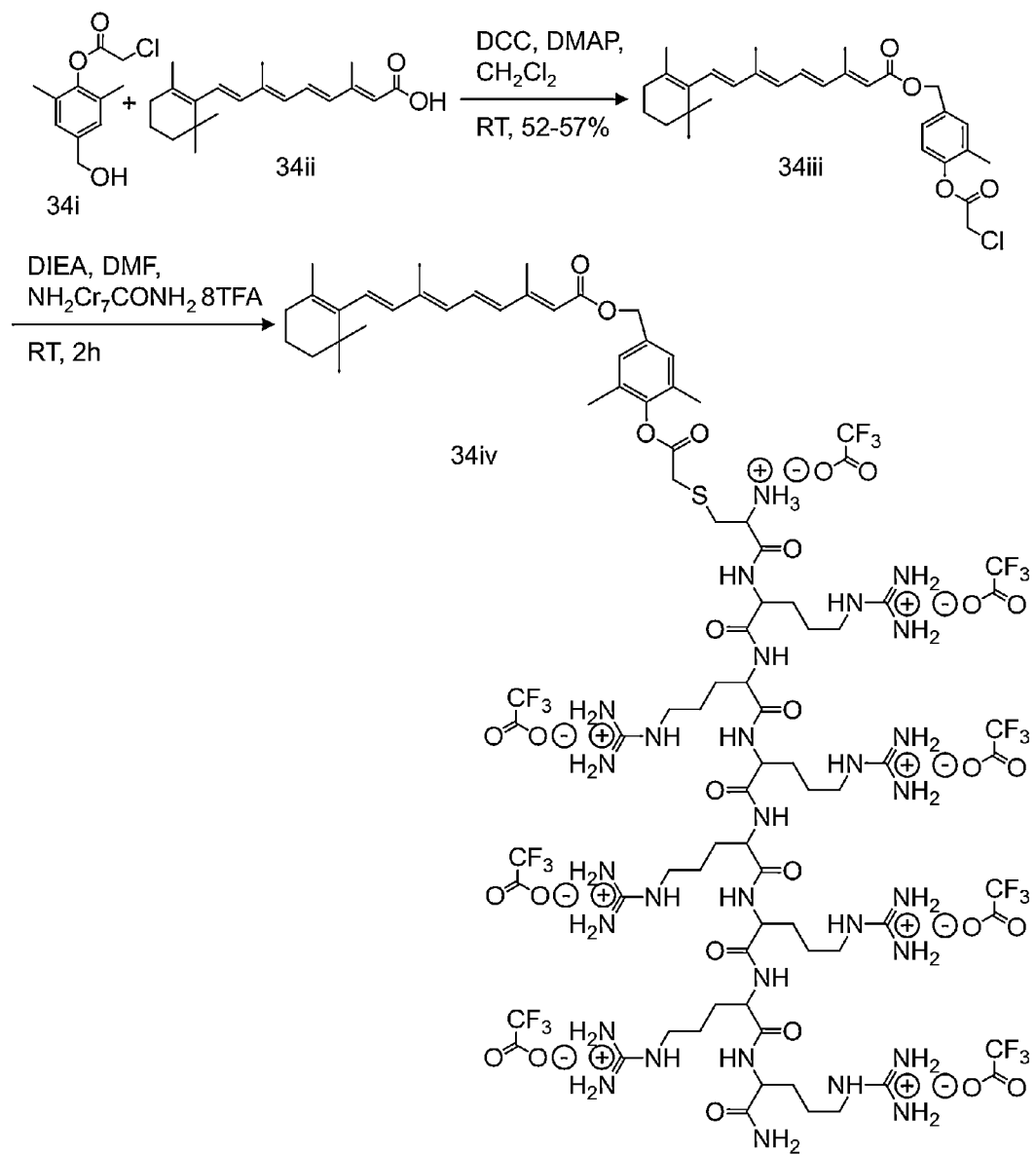

FIG. 34 illustrates the use of a cleavable linker in preparing a retinoic acid-r9 conjugate.

Figure 35:
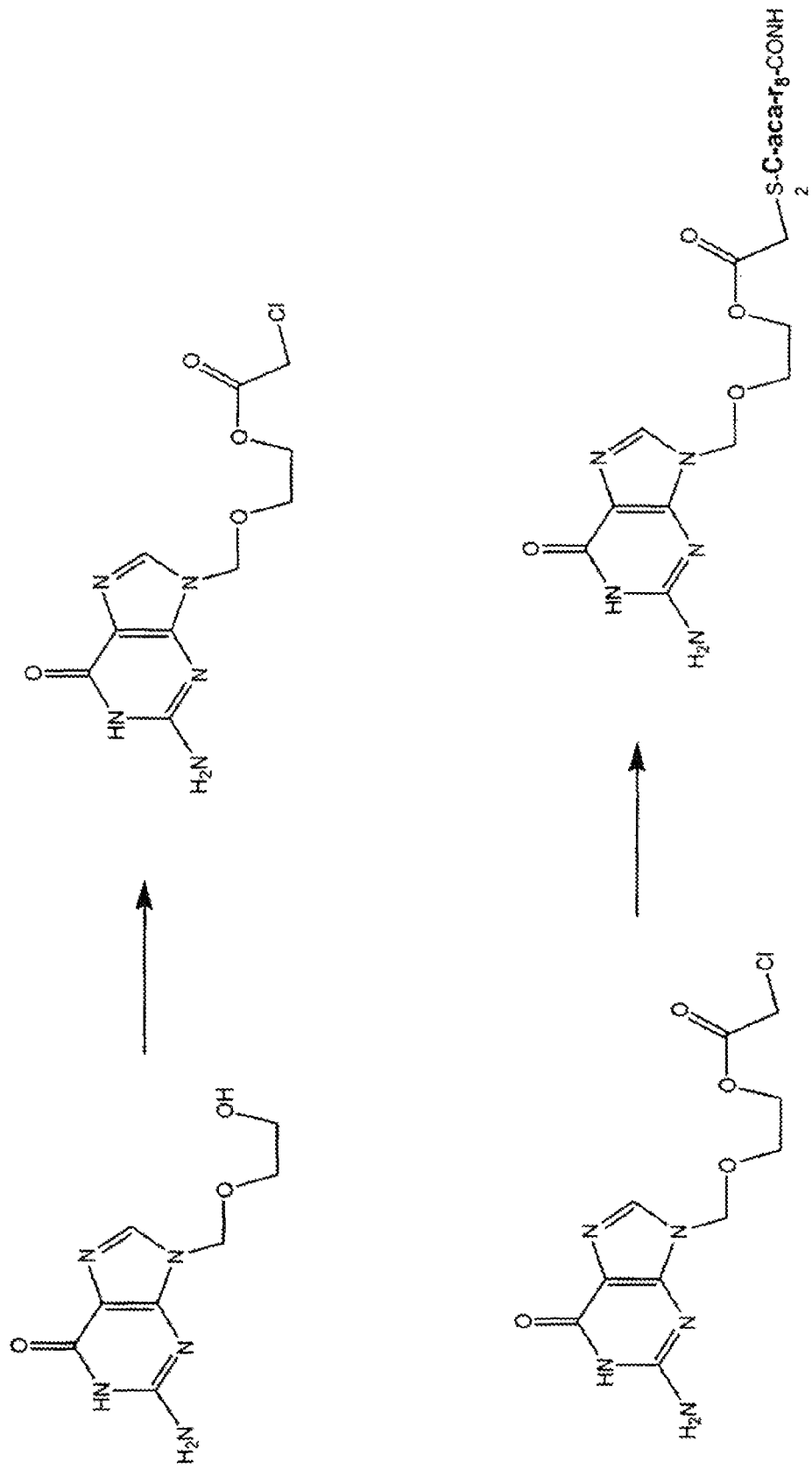

FIG. 35 illustrates a method of linking active agents such as acyclovir to transport moieties.

Figure 36:
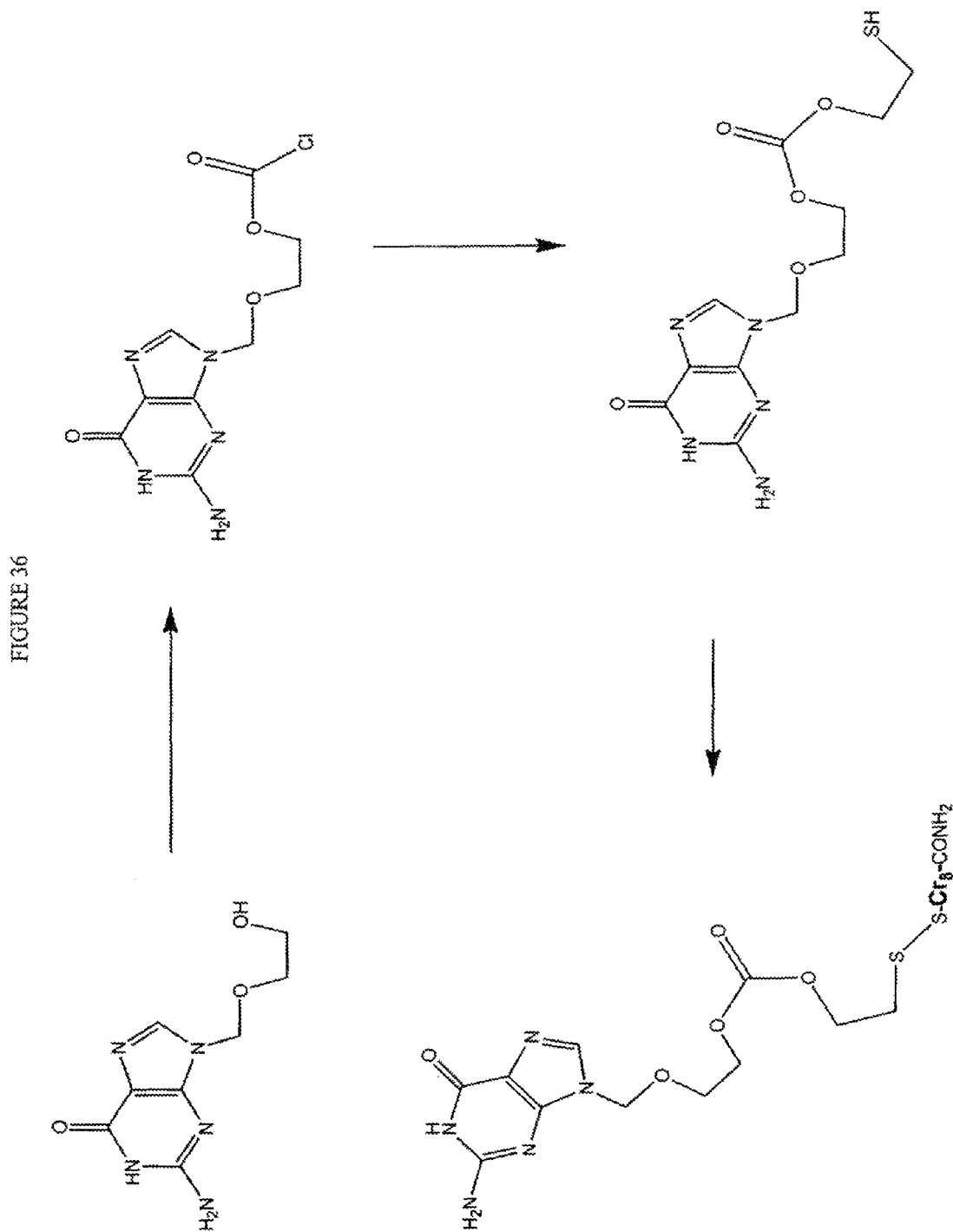

FIG. 36 illustrates a method of linking active agents such as acyclovir to transport moieties.

Figure 37:
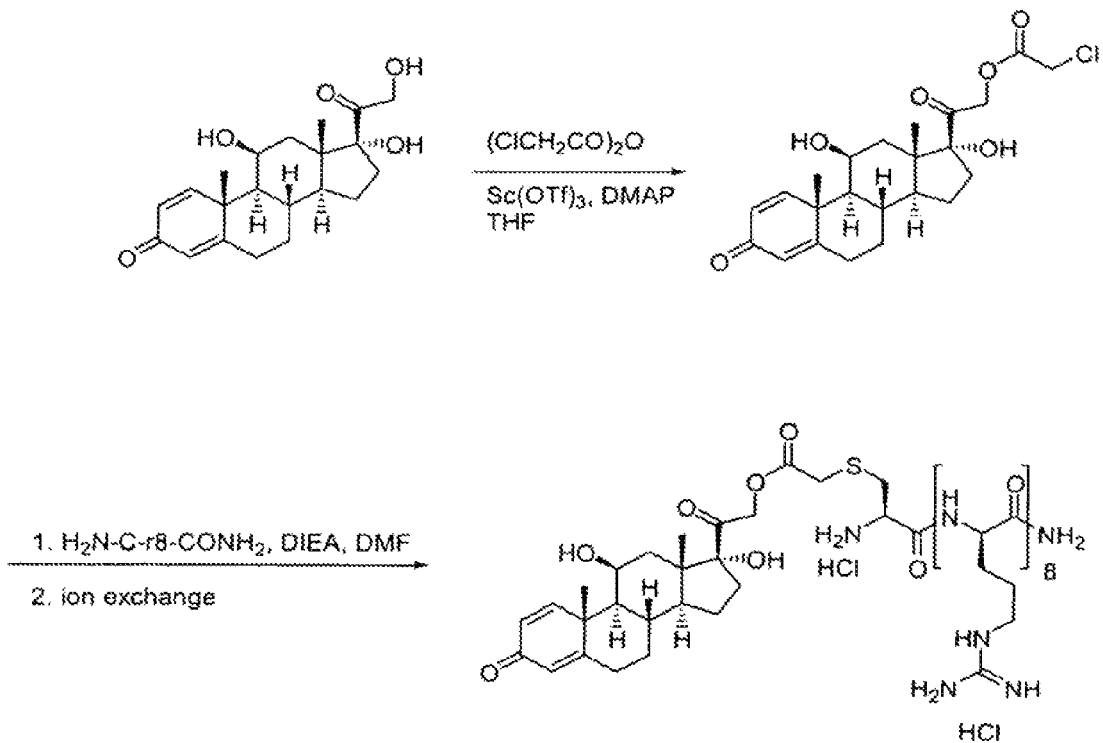

FIG. 37 illustrates a method of linking active agents such as a corticoid steroid to transport moieties.

DETAILED DESCRIPTION

Definitions

"Ocular tissue" refers to tissue of the eye and eyelid. Tissues or layers of the eye include, e.g., the sclera, the cornea, which comprises a layer of nonkaratenized squamous epithelia, the corneal stroma, endothelium, including a cell layer lying on the thick basement membrane (Descement's membrane). Additional ocular layers include, e.g., The zona occludens, the aqueous humor, the iris, the vitreous humor/vitreous body, the choroid, the ciliary body including the ciliary epithelium, the retina, including the rod and cone cells, the lens and the optic nerve. See. e.g., GRAY'S ANATOMY (Williams et al., eds., 1995).

An "epithelial tissue" is the basic tissue that covers surface areas of the surface, spaces, and cavities of the body. Epithelial tissues are composed primarily of epithelial cells that are attached to one another and rest on an extracellular matrix (basement membrane) that is typically produced by the cells. Epithelial tissues include three general types based on cell shape: squamous, cuboidal, and columnar epithelium. Squamous epithelium, which lines lungs and blood vessels, as well as the cornea, is made up of flat cells. Cuboidal epithelium lines kidney tubules and is composed of cube shaped cells, while columnar epithelium cells line the digestive tract and have a columnar appearance. Epithelial tissues can also be classified based on the number of cell layers in the tissue. For example, a simple epithelial tissue is composed of a single layer of cells, each of which sits on the basement membrane. A "stratified" epithelial tissue is composed of several cells stacked upon one another; not all cells contact the basement membrane. A "pseudostratified" epithelial tissue has cells that, although all contact the basement membrane, appear to be stratified because the nuclei are at various levels.

The term "trans-epithelial" delivery or administration refers to the delivery or administration of agents by permeation through one or more layers of a body surface or tissue, such as cornea, zona occludens, lens and the like, by topical administration. Delivery can be to a deeper layer of the tissue, for example, and/or delivery to or from the bloodstream.

"Delivery enhancement," "penetration enhancement" or "permeation enhancement" as used herein relates to an increase in amount and/or rate of delivery of a compound that is delivered into and across one or more layers of an epithelial or endothelial tissue or other ocular tissue. An enhancement of delivery can be observed by measuring the rate and/or amount of the compound that passes through one or more layers of such tissue. Delivery enhancement also can involve an increase in the depth into the tissue to which the compound is delivered, and/or the extent of delivery to one or more cell types of the epithelial or other tissue (e.g., increased delivery to cornea, optic nerve, lens or other tissue). Such measurements are readily obtained by, for example, using a diffusion cell apparatus as described in U.S. Pat. No. 5,891,462.

The amount or rate of delivery of an agent across and/or into ocular or other epithelial or endothelial membrane is sometimes quantitated in terms of the amount of compound passing through a predetermined area of eye or other tissue. That area will usually be in the range of about 0.1 $cm^2$ to about 100 $cm^2$, for example in the range of about 0.1 $cm^2$ to about 1 $cm^2$, or in the range of about 0.5 $cm^2$ to about 2 $cm^2$.

The terms "guanidyl," "guanidinyl" and "guanidino" are used interchangeably to refer to a moiety having the formula —HN=C(NH$_2$)NH (unprotonated form). As an example, arginine contains a guanidyl (guanidino) moiety, and is also referred to as 2-amino-5-guanidinovaleric acid or α-amino-6-guanidinovaleric acid. "Guanidium" refers to the positively charged conjugate acid form. The term "guanidino moiety" includes, for example, guanidine, guanidinium, guanidine derivatives such as (RNHC(NH)NHR'), monosubstituted guanidines, monoguanides, biguanides, biguanide derivatives such as (RNHC(NH)NHC(NH)NHR'), and the like. In addition, the term "guanidino moiety" encompasses any one or more of a guanide alone or a combination of different guanides.

"Amidinyl" and "amidino" refer to a moiety having the formula —C(=NH)(NH$_2$). "Amidinium" refers to the positively charged conjugate acid form.

The term "trans-barrier concentration" or "trans-tissue concentration" refers to the concentration of a compound present on the side of one or more layers of an epithelial or endothelial barrier tissue that is opposite or "trans" to the side of the tissue to which a particular composition has been added. For example, when a compound is applied to the eye, the amount of the compound measured subsequently across one or more layers of the eye is the trans-barrier concentration of the compound.

"Biologically active agent" or "biologically active substance" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

The term "macromolecule" as used herein refers to large molecules (MW greater than 1000 daltons) exemplified by, but not limited to, peptides, proteins, oligonucleotides and polynucleotides of biological or synthetic origin.

"Small organic molecule" refers to a carbon-containing agent having a molecular weight (MW) of less than or equal to 1000 daltons.

The terms "non-polypeptide agent" and "non-polypeptide therapeutic agent" refer to the portion of a conjugate that does not include the delivery-enhancing transporter, and that is a biologically active agent other than a polypeptide. An example of a non-polypeptide agent is an anti-sense oligonucleotide, which can be conjugated to a poly-arginine peptide to form a conjugate for enhanced delivery into and across one or more layers of an epithelial or endothelial tissue.

A "subunit," as used herein, is a monomeric unit that are joined to form a larger polymeric compound. The set of amino acids are an example of subunits. Each amino acid shares a common backbone (—C—C—N—), and the different amino acids differ in their sidechains. The backbone is repeated in a polypeptide. A subunit represents the shortest repeating pattern of elements in a polymer backbone. For example, two amino acids of a peptide are not considered a peptide because two amino acids would not have the shortest repeating pattern of elements in the polymer backbone.

The term "polymer" refers to a linear chain of two or more identical or non-identical subunits joined by covalent bonds. A peptide is an example of a polymer; peptides can be composed of identical or non-identical amino acid subunits that are joined by peptide linkages (amide bonds).

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine). Homopolymer peptides are represented by a one-letter amino acid symbol followed by the number of consecutive occurrences of that amino acid in the peptide— (e.g., R7 (SEQ ID NO:3) represents a heptamer that consists of L-arginine residues).

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

DESCRIPTION OF THE PREFERRED EMBODIMENTS

The present invention provides compositions and methods that enhance the transfer of compounds, including drugs and other biologically active compounds, into and across one or more layers of an animal ocular tissue, including epithelial or endothelial tissue, as well as other ocular tissue. The methods involve contacting the tissue with a conjugate that includes the compound of interest linked to a delivery-enhancing transporter. The delivery enhancing transporters provided by the invention are molecules that include sufficient guanidino or amidino moieties to increase delivery of the conjugate into and across one or more intact epithelial and endothelial tissue layers. The methods and compositions are useful for trans-epithelial and trans-endothelial delivery of drugs and other biologically active molecules, and also for delivery of imaging and diagnostic molecules. The methods and compositions of the invention are useful for delivery of compounds that require trans-epithelial or trans-endothelial transport to exhibit their biological effects, and that by themselves (without conjugation to a delivery-enhancing transporters or some other modification), are unable, or only poorly able, to cross such tissues and thus exhibit biological activity.

The delivery-enhancing transporters and methods of the invention provide significant advantages over previously available methods for obtaining trans-epithelial and trans-endothelial tissue delivery of compounds of interest. The transporters make possible the delivery of drugs and other agents across tissues that were previously impenetrable to the drug. For example, while delivery of drugs across the retinal or corneal epithelium was previously nearly impossible for all but a few compounds, the methods of the invention can deliver compounds not only into cells of a first layer of an epithelial tissue but also across one or more layers of this layer.

The delivery-enhancing transporters increase delivery of the conjugate into and across one or more intact epithelial or endothelial tissue layers compared to delivery of the compound in the absence of the delivery-enhancing transporter. The delivery-enhancing transporters can, in some embodiments, increase delivery of the conjugate significantly over that obtained using the tat protein of HIV-1 (Frankel et al. (1991) PCT Pub. No. WO 91109958). Delivery is also increased significantly over the use of shorter fragments of the tat protein containing the tat basic region (residues 49-57 having the sequence RKKRRQRRR; SEQ ID NO:28) (Barsoum et al. (1994) WO 94/04686 and Fawell et al. (1994) Proc. Nat'l. Acad. Sci. USA 91: 664-668). Preferably, delivery obtained using the transporters of the invention is increased more than 2-fold, still more preferably six-fold, still more preferably ten-fold, and still more preferably twenty-fold, over that obtained with tat residues 49-57. In some embodiments, the compositions of the invention do not include tat residues 49-57.

Similarly, the delivery-enhancing transporters of the invention can provide increased delivery compared to a 16 amino acid peptide-cholesterol conjugate derived from the Antennapedia homeodomain that is rapidly internalized by cultured neurons (Brugidou et al. (1995) *Biochem. Biophys. Res. Commun.* 214: 685-93). This region, residues 43-58 at minimum, has the amino acid sequence RQIKIWFQNRRMKWKK (SEQ ID NO:29). The Herpes simplex protein VP22, like tat and the Antennapedia domain, was previously known to enhance transport into cells, but was not known to enhance transport into and across endothelial and epithelial membranes (Elliot and O'Hare (1997) Cell 88: 223-33; Dilber et al. (1999) *Gene Ther.* 6: 12-21; Phelan et al. (1998) *Nature Biotechnol.* 16: 440-3). In some embodiments, the delivery-enhancing transporters provide significantly increased delivery compared to the Antennapedia homeodomain and to the VP22 protein. In some embodiments, the compositions of the invention do not include the Antennapedia homeodomain, the VP22 protein or eight contiguous arginines (SEQ ID NO:4).

Structure of Delivery-Enhancing Transporters

The delivery-enhancing transporters of the invention are molecules that have sufficient guanidino and/or amidino moieties to increase delivery of a compound to which the delivery-enhancing transporter is attached into and across one or more layers of an ocular epithelial tissue or an endothelial tissue. The delivery-enhancing transporters generally include a backbone structure to which is attached the guanidino and/or amidino sidechain moieties. In some embodiments, the backbone is a polymer that consists of subunits (e.g., repeating monomer units), at least some of which subunits contain a guanidino or amidino moiety.

A. Guanidino and/or Amidino Moieties

The delivery-enhancing transporters typically display at least 5 guanidino and/or amidino moieties, and more preferably 7 or more such moieties. Preferably, the delivery-enhancing transporters have 25 or fewer guanidino and/or amidino moieties, and often have 15 or fewer of such moieties. In some embodiments, the delivery-enhancing transporter consists essentially of 50 or fewer subunits, and can consist essentially of 25 or fewer, 20 or fewer, or 15 or fewer subunits. The delivery-enhancing transporter can be as short as 5 subunits, in which case all subunits include a guanidino or amidino sidechain moiety. The delivery-enhancing transporters can have, for example, at least 6 subunits, and in some embodiments have at least 7 or 10 subunits. Generally, at least 50% of the subunits contain a guanidino or amidino sidechain moiety. More preferably, at least 70% of the subunits, and sometimes at least 90% of the subunits in the delivery-enhancing transporter contain a guanidino or amidino sidechain moiety.

Some or all of the guanidino and/or amidino moieties in the delivery-enhancing transporters can be contiguous. For example, the delivery-enhancing transporters can include from 6 to 25 contiguous guanidino and/or amidino-containing subunits. Seven or more contiguous guanidino and/or amidino-containing subunits are present in some embodiments. In some embodiments, each subunit that contains a guanidino moiety is contiguous, as exemplified by a polymer containing at least six contiguous arginine residues.

The delivery-enhancing transporters are exemplified by peptides. Arginine residues or analogs of arginine can constitute the subunits that have a guanidino moiety. Such an arginine-containing peptide can be composed of either all D-, all L- or mixed D- and L-amino acids, and can include additional amino acids, amino acid analogs, or other molecules between the arginine residues. Optionally, the delivery-enhancing transporter can also include a non-arginine residue to which a compound to be delivered is attached, either directly or through a linker. The use of at least one D-arginine in the delivery-enhancing transporters can enhance biological stability of the transporter during transit of the conjugate to its biological target. In some cases the delivery-enhancing transporters are at least about 50% D-arginine residues, and for even greater stability transporters in which all of the subunits are D-arginine residues are used. If the delivery enhancing transporter molecule is a peptide, the transporter is not attached to an amino acid sequence to which the amino acids that make up the delivery enhancing transporter molecule are attached in a naturally occurring protein.

Preferably, the delivery-enhancing transporter is linear. In a preferred embodiment, an agent to be delivered into and across one or more layers of an epithelial tissue is attached to a terminal end of the delivery-enhancing transporter. In some embodiments, the agent is linked to a single transport polymer to form a conjugate. In other embodiments, the conjugate can include more than one delivery-enhancing transporter linked to an agent, or multiple agents linked to a single delivery-enhancing transporter.

More generally, it is preferred that each subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

The guanidino or amidino moieties extend away from the backbone by virtue of being linked to the backbone by a sidechain linker. The sidechain atoms are preferably provided as methylene carbon atoms, although one or more other atoms such as oxygen, sulfur or nitrogen can also be present. For example, a linker that attaches a guanidino moiety to a backbone can be shown as:

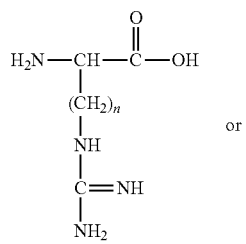

1

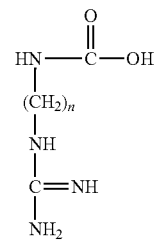

2

In these formulae, n is preferably at least 2, and is preferably between 2 and 7. In some embodiments, n is 3 (arginine for structure 1). In other embodiments, n is between 4 and 6; most preferably n is 5 or 6. Although the sidechain in the exemplified formulae is shown as being attached to a peptide backbone (i.e., a repeating amide to which the sidechain is attached to the carbon atom that is α to the carbonyl group, subunit 1) and a peptoid backbone (i.e., a repeating amide to which the sidechain is attached to the nitrogen atom that is β to the carbonyl group, subunit 2), other non-peptide backbones are also suitable, as discussed in more detail herein. Thus, similar sidechain linkers can be attached to nonpeptide backbones (e.g., peptoid backbones).

In some embodiments, the delivery-enhancing transporters are composed of linked subunits, at least some of which include a guanidino and/or amidino moiety. Examples of suitable subunits having guanidino and/or amidino moieties are described below.

Amino Acids.

In some embodiments, the delivery-enhancing transporters are composed of D or L amino acid residues. The amino acids can be naturally occurring or non-naturally occurring amino acids. Arginine (α-amino-δ-guanidinovaleric acid) and α-amino-ε-amidino-hexanoic acid (isosteric amidino analog) are examples of suitable guanidino- and amidino-containing amino acid subunits. The guanidinium group in arginine has a pKa of about 12.5. In some preferred embodiments the transporters are comprised of at least six contiguous arginine residues.

Other amino acids, such as α-amino-β-guanidino-propionic acid, α-amino-γ-guanidino-butyric acid, or α-amino-ε-guanidino-caproic acid (containing 2, 3 or 5 sidechain linker atoms, respectively, between the backbone chain and the central guanidinium carbon) can also be used.

D-amino acids can also be used in the delivery enhancing transporters. Compositions containing exclusively D-amino acids have the advantage of decreased enzymatic degradation. However, they can also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included within the conjugate to promote release of the agent in cells or organelles.

In addition, the transport moieties are amino acid oligomers of the following formulae: $(ZYZ)_nZ$, $(ZY)_nZ$, $(ZYY)_nZ$ and $(ZYYY)_nZ$. See, U.S. patent application Ser. No. 09/779,693, filed Feb. 7, 2001 and U.S. Patent Application No. 60/182,166, filed Feb. 14, 2000. "Z" in the formulae is D or L-arginine. "Y" is an amino acid that does not contain a guanidyl or amidinyl moiety. The subscript "n" is an integer ranging from 2 to 25.

In the above transport moiety formulae, the letter "Y" represents a natural or non-natural amino acid. The amino acid can be essentially any compound having (prior to incorporation into the transport moiety) an amino group ($NH_2$ or NH-alkyl) and a carboxylic acid group ($CO_2H$) and not containing either a guanidyl or amidinyl moiety. Examples of such compounds include D and L-alanine, D and L-cysteine, D and L-aspartic acid, D and L-glutamic acid, D and L-phenylalanine, glycine, D and L-histidine, D and L-isoleucine, D and L-lysine, D and L-leucine, D and L-methionine, D and L-asparagine, D and L-proline, D and L-glutamine, D and L-serine, D and L-threonine, D and L-valine, D and L-tryptophan, D and L-hydroxyproline, D and L-tyrosine, sarcosine, β-alanine, γ-amino butyric acid and ε-amino caproic acid. In each of the above formulae, each Y will be independent of any other Y present in the transport moiety, though in some embodiments, all Y groups can be the same.

In one group of preferred embodiments, the transport moiety has the formula $(ZYZ)_nZ$ (SEQ ID NOS:33-36), wherein each "Y" is independently selected from glycine, β-alanine, "γ-amino butyric acid and ε-amino caproic acid, "Z" is preferably L-arginine, and n is preferably an integer ranging from 2 to 5. More preferably, each "Y" is glycine or ε-amino caproic acid and n is 3 (SEQ ID NO:37). Within this group of embodiments, the use of glycine is preferred for those compositions in which the transport moiety is fused or covalently attached directly to a polypeptide biological agent such that the entire composition can be prepared by recombinant methods. For those embodiments in which the transport moiety is to be assembled using, for example, solid phase methods, ε-amino caproic acid is preferred.

In another group of preferred embodiments, the transport moiety has the formula $(ZY)_nZ$ (SEQ ID NOS:38-44), wherein each "Y" is preferably selected from glycine, -alanine, γ-amino butyric acid and ε-amino caproic acid, "Z" is preferably L-arginine, and n is preferably an integer ranging from 4 to 10. More preferably, each "Y" is glycine or ε-amino caproic acid and n is 6 (SEQ ID NO:45). As with the above group of specific embodiments, the use of glycine is preferred for those compositions in which the transport moiety is fused or covalently attached directly to a polypeptide biological agent such that the entire composition can be prepared by recombinant methods. For solution or solid phase construction of the transport moiety, ε-amino caproic acid is preferred.

In yet another group of preferred embodiments, the transport moiety has the formula $(ZYY)_nZ$ (SEQ ID NOS:46-52), wherein each "Y" is preferably selected from glycine, β-alanine, "(-amino butyric acid and £-amino caproic acid, "Z" is preferably L-arginine, and n is preferably an integer ranging from 4 to 10. More preferably, each "Y" is glycine or ε-amino caproic acid and n is 6 (SEQ ID NO:53).

In still another group of preferred embodiments, the transport moiety has the formula $(ZYYY)_nZ$ (SEQ ID NOS:54-60), wherein each "Y" is preferably selected from glycine, β-alanine, γ-amino butyric acid and ε-amino caproic acid, "Z" is preferably L-arginine, and n is preferably an integer ranging from 4 to 10. More preferably, "Y" is glycine and n is 6 (SEQ ID NO:61).

In other embodiments, each of the Y groups will be selected to enhance certain desired properties of the transport moeity. For, example, when transport moeities having a more hydrophobic character are desired, each Y can be selected from those naturally occurring amino acids that are typically grouped together as hydrophobic amino acids (e.g., phenylalanine; phenylglycine, valine, leucine, isoleucine). Similarly, transport moieties having a more hydrophilic character can be prepared when some or all of the Y groups are hydrophilic amino acids (e.g., lysine, serine, threonine, glutamic acid, and the like).

One of skill in the art will appreciate that the transport moiety can be a polypeptide fragment within a larger polypeptide. For example, the transport moiety can be of the formula $(ZYY)_nZ$ (SEQ ID NOS:46-52) yet have additional amino acids which flank this moiety (e.g., $X_m(ZYY)_nZ—X_p$ (SEQ ID NOS:62-68) wherein the subscripts m and p represent integers of zero to about 10 and each X is independently a natural or non-natural amino acid).

Other Subunits.

Subunits other than amino acids can also be selected for use in forming transport polymers. Such subunits can include, but are not limited to, hydroxy amino acids, N-methyl-amino acids amino aldehydes, and the like, which result in polymers with reduced peptide bonds. Other subunit types can be used, depending on the nature of the selected backbone, as discussed in the next section.

B. Backbones

The guanidino and/or amidino moieties that are included in the delivery-enhancing transporters are generally attached to a linear backbone. The backbone can comprise a variety of atom types, including carbon, nitrogen, oxygen, sulfur and phosphorus, with the majority of the backbone chain atoms typically consisting of carbon. A plurality of sidechain moieties that include a terminal guanidino or amidino group are attached to the backbone. Although spacing between adjacent sidechain moieties is typically consistent, the delivery-enhancing transporters used in the invention can also include variable spacing between sidechain moieties along the backbone.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), trans-alkene (CR=CH), fluoroalkene (CF=CH), dimethylene ($CH_2CH_2$), thioether ($CH_2S$), hydroxyethylene ($CH(OH)CH_2$), methyleneoxy ($CH_2O$), tetrazole ($CN_4$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted amides), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

As mentioned above, in a peptoid backbone, the sidechain is attached to the backbone nitrogen atoms rather than the carbon atoms. (See e.g., Kessler (1993) Angew. Chem. Int. Ed. Engl. 32:543; Zuckerman et al. (1992) Chemtracts-Macromol. Chem. 4:80; and Simon et al. (1992) Proc. Nat'l. Acad. Sci. USA 89:9367.) An example of a suitable peptoid backbone is poly-(N-substituted)glycine (poly-NSG). Synthesis of peptoids is described in, for example, U.S. Pat. No. 5,877, 278. As the term is used herein, transporters that have a peptoid backbone are considered "non-peptide" transporters, because the transporters are not composed of amino acids having naturally occurring sidechain locations. Non-peptide backbones, including peptoid backbones, provide enhanced biological stability (for example, resistance to enzymatic degradation in vivo).

C. Synthesis of Delivery-Enhancing Transporters

Delivery-enhancing transporters are constructed by any method known in the art. Exemplary peptide polymers can be produced synthetically, preferably using a peptide synthesizer (e.g., an Applied Biosystems Model 433) or can be synthesized recombinantly by methods well known in the art. Recombinant synthesis is generally used when the delivery-enhancing transporter is a peptide which is fused to a polypeptide or protein of interest.

N-methyl and hydroxy-amino acids can be substituted for conventional amino acids in solid phase peptide synthesis. However, production of delivery-enhancing transporters with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al. (1998) *Chem. Rev.* 98:763, Simon et al. (1992) *Proc. Nat'l. Acad. Sci. USA* 89:9367, and references cited therein.

The delivery-enhancing transporters of the invention can be flanked by one or more non-guanidino/non-amidino subunits (such as glycine, alanine, and cysteine, for example), or a linker (such as an aminocaproic acid group), that do not significantly affect the rate of trans-tissue layer transport of the corresponding delivery-enhancing transporter-containing conjugates. Also, any free amino terminal group can be capped with a blocking group, such as an acetyl or benzyl group, to prevent ubiquitination in vivo.

Where the transporter is a peptoid polymer, one synthetic method involves the following steps: 1) a peptoid polyamine is treated with a base and pyrazole-1-carboxamidine to provide a mixture; 2) the mixture is heated and then allowed to cool; 3) the cooled mixture is acidified; and 4) the acidified mixture is purified. Preferably the base used in step 1 is a carbonate, such as sodium carbonate, and heating step 2 involves heating the mixture to approximately 50° C. for between about 24 hours and about 48 hours. The purification step preferably involves chromatography (e.g., reverse-phase HPLC).

D. Attachment of Transport Polymers to Biologically Active Agents

The agent to be transported can be linked to the delivery-enhancing transporter according to a number of embodiments. In one embodiment, the agent is linked to a single delivery-enhancing transporter, either via linkage to a terminal end of the delivery-enhancing transporter or to an internal subunit within the reagent via a suitable linking group.

In a second embodiment, the agent is attached to more than one delivery-enhancing transporter, in the same manner as above. This embodiment is somewhat less preferred, since it can lead to crosslinking of adjacent cells.

In a third embodiment, the conjugate contains two agent moieties attached to each terminal end of the delivery-enhancing transporter. For this embodiment, it is presently preferred that the agent has a molecular weight of less than 10 kDa.

With regard to the first and third embodiments just mentioned, the agent is generally not attached to one any of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogeneous mixtures.

According to an important aspect of the present invention, it has been found by the applicants that attachment of a single delivery-enhancing transporter to any of a variety of types of biologically active agents is sufficient to substantially enhance the rate of uptake of an agent into and across one or more layers of epithelial and endothelial tissues, even without requiring the presence of a large hydrophobic moiety in the conjugate. In fact, attaching a large hydrophobic moiety can significantly impede or prevent cross-layer transport due to adhesion of the hydrophobic moiety to the lipid bilayer of cells that make up the epithelial or endothelial tissue. Accordingly, the present invention includes conjugates that do not contain substantially hydrophobic moieties, such as lipid and fatty acid molecules.

Delivery-enhancing transporters of the invention can be attached covalently to biologically active agents by chemical or recombinant methods.

1. Chemical Linkages

Biologically active agents such as small organic molecules and macromolecules can be linked to delivery-enhancing transporters of the invention via a number of methods known in the art (see, for example, Wong, S. S., Ed., *Chemistry of Protein Conjugation and Cross-Linking*, CRC Press, Inc., Boca Raton, Fla. (1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the biologically active agent to the transport polymer. Groups that are not known to be part of an active site of the biologically active agent are preferred, particularly if the polypeptide or any portion thereof is to remain attached to the substance after delivery.

Polymers, such as peptides produced as described in PCT application US98/10571 (Publication No. WO 9852614), are generally produced with an amino terminal protecting group, such as FMOC. For biologically active agents which can survive the conditions used to cleave the polypeptide from the synthesis resin and deprotect the sidechains, the FMOC may be cleaved from the N-terminus of the completed resin-bound polypeptide so that the agent can be linked to the free N-terminal amine. In such cases, the agent to be attached is typically activated by methods well known in the art to produce an active ester or active carbonate moiety effective to form an amide or carbamate linkage, respectively, with the polymer amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N—$NO_2$, and the like.

Coupling reactions are performed by known coupling methods in any of an array of solvents, such as N,N-dimethyl formamide (DMF), N-methylpyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

2. Fusion Polypeptides

Delivery-enhancing transporters of the invention can be attached to biologically active polypeptide agents by recombinant means by constructing vectors for fusion proteins comprising the polypeptide of interest and the delivery-enhancing transporter, according to methods well known in the art. Generally, the delivery-enhancing transporter component will be attached at the C-terminus or N-terminus of the polypeptide of interest, optionally via a short peptide linker.

3. Releasable Linkers

The biologically active agents are, in presently preferred embodiments, attached to the delivery-enhancing transporter using a linkage that is specifically cleavable or releasable. The use of such linkages is particularly important for biologically active agents that are inactive until the attached delivery-enhancing transporter is released. In some cases, such conjugates that consist of a drug molecule that is attached to a delivery-enhancing transporter can be referred to as prodrugs, in that the release of the delivery-enhancing transporter from the drug results in conversion of the drug from an inactive to an active form. As used herein, "cleaved" or "cleavage" of a conjugate or linker refers to release of a biological agent from a transporter molecule, thereby releasing an active biological agent. "Specifically cleavable" or "specifically releasable" refers to the linkage between the transporter and the agent being cleaved, rather than the transporter being degraded (e.g., by proteolytic degradation).

In some embodiments, the linkage is a readily cleavable linkage, meaning that it is susceptible to cleavage under conditions found in vivo. Thus, upon passing into and through one or more layers of an epithelial and/or endothelial tissue, the agent is released from the delivery-enhancing transporter. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The linkage can be selected so it is cleavable by an enzymatic activity that is known to be present in one or more layers of an epithelial or endothelial tissue.

A specifically cleavable linker can be engineered onto a transporter molecule. For example, amino acids that constitute a protease recognition site, or other such specifically recognized enzymatic cleavage site, can be used to link the transporter to the agent. Alternatively, chemical or other types of linkers that are cleavable by, for example, exposure to light or other stimulus can be used to link the transporter to the agent of interest.

A conjugate in which an agent to be delivered and a delivery-enhancing transporter are linked by a specifically cleavable or specifically releasable linker will have a half-life. The term "half-life" in this context refers to the amount of time required after applying the conjugate to an epithelial or endothelial membrane for one half of the amount of conjugate to become dissociated to release the free agent. The half-life for some embodiments is between about 5 minutes and 24 hours, and, in some embodiments, is between 30 minutes and 2 hours. In some embodiments, the conjugate is stable in a buffered saline solution (e.g., PBS), but has a short half-life (e.g., less than one hour) in a cell. The half-life of a conjugate can be "tuned" or modified, according to the invention, as described below.

In some embodiments, the cleavage rate of the linkers is pH dependent. For example, a linker can form a stable linkage between an agent and a delivery-enhancing transporter at an acidic pH (e.g., pH 6.5 or less, more preferably about 6 or less, and still more preferably about 5.5 or less). However, when the conjugate is placed at physiological pH (e.g., pH 7 or greater, preferably about pH 7.4), the linker will undergo cleavage to release the agent. Such pH sensitivity can be obtained by, for example, including a functional group that, when protonated (i.e., at an acidic pH), does not act as a nucleophile. At a higher (e.g., physiological) pH, the functional group is no longer protonated and thus can act as a nucleophile. Examples of suitable functional groups include, for example, N and S. One can use such functional groups to fine-tune the pH at which self-cleavage occurs.

In another embodiment, the linking moiety is cleaved through self-immolation. Such linking moieties in a transport moiety-biologically active compound conjugate contain a nucleophile (e.g., oxygen, nitrogen and sulfur) distal to the biologically active compound and a cleavable group (e.g., ester, carbonate, carbamate and thiocarbamate) proximal to the biologically active compound. Intramolecular attack of the nucleophile on the cleavable group results in the scission of a covalent bond, thereby releasing the linking moiety from the biologically active compound.

Examples of conjugates containing self-immolating linking moieties (e.g., biologically active agent-L-transport moiety conjugates) are represented by structures 3, 4 and 5:

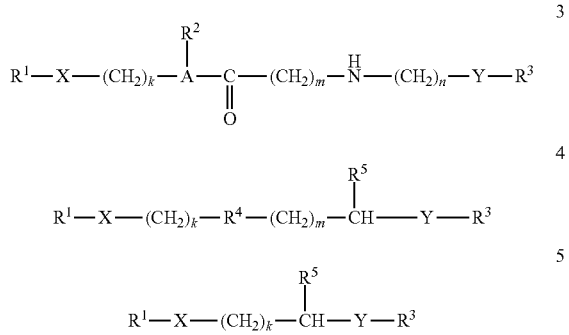

wherein: $R^1$ is the biologically active compound; X is a linkage formed between a functional group on the biologically active compound and a terminal functional group on the linking moiety; Y is a linkage formed from a functional group on the transport moiety and a functional group on the linking moiety; A is N or CH; $R^2$ is hydrogen, alkyl, aryl, arylalkyl, acyl or allyl; $R^3$ is the transport moiety; $R^4$ is S, O, $NR^6$ or $CR^7R^8$; $R^5$ is H, OH, SH or $NHR^6$; $R^6$ is hydrogen, alkyl, aryl, acyl or allyl; $R^7$ and $R^8$ are independently hydrogen or alkyl; k and m are independently either 1 or 2; and n is an integer ranging from 1 to 10. Non-limiting examples of the X and Y linkages are (in either orientation): —C(O)O—, —C(O)NH—, —OC(O)NH—, —S—S—, —C(S)O—, —C(S)NH—, —NHC(O)NH—, —SO$_2$NH—, —SONH—, phosphate, phosphonate and phosphinate. One of skill in the art will appreciate that when the biological agent has a hydroxy functional group, then X will preferably be —OC(O)— or —OC(O)NH—. Similarly, when the linking group is attached to an amino terminus of the transport moiety, Y will preferably be —C(O)NH—, —NHC(O)NH—, —SO$_2$NH—, —SONH— or —OC(O)NH— and the like. In each of the groups provided above, NH is shown for brevity, but each of the linkages (X and Y) can contain substituted (e.g., N-alkyl or N-acyl) linkages as well.

Turning first to linking groups illustrated by structure 3, an example and preferred embodiment is illustrated for formula 3a:

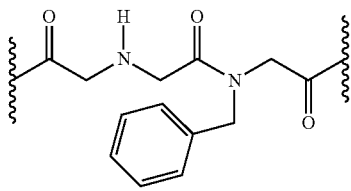

Figure 6:
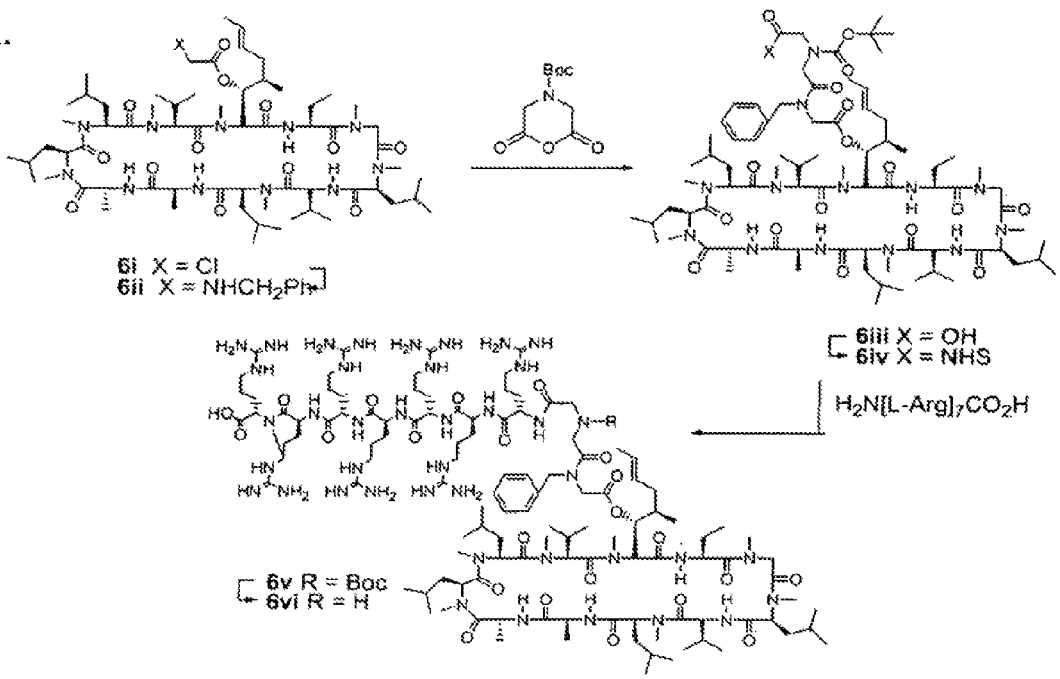
Figure 6:
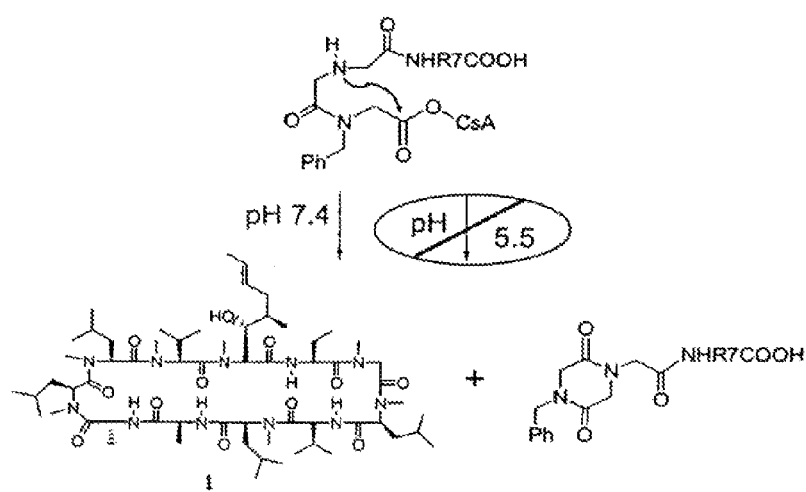

3a wherein the wavy lines indicate points of attachment to the transport moiety and to the biologically active compound. Preparation of a conjugate containing this linking group is illustrated in Example 10 (FIG. 6). In this Example and FIG. 6, cyclosporin A is treated with chloroacetic anhydride to form the chloroacetate ester 6i (numbering in FIG. 6) which is then combined with benzylamine to form the N-benzyl glycine conjugate 6ii. Condensation of the glycine conjugate with Boc-protected diglycine anhydride provides the acid 6iii which is converted to the more reactive N-hydroxy succinimide ester 6iv and then combined with the amino terminus of a transport moiety to form an amide linkage. One of skill in the art will appreciate that the N-benzyl group can be replaced with other groups (e.g., alkyl, aryl, allyl and the like) or that methylene groups can be replaced with, for example, ethylene, propylene and the like. Preferably, the methylene groups are retained as shown in 3a, to provide an appropriate steric or spatial orientation that allows the linkage to be cleaved in vivo (see FIG. 6B).

Accordingly, for structure 3, the following substituents are preferred: A is N; $R^2$ is benzyl; k, m and n are 1; X is —OC(O)— and Y is —C(O)NH—.

Linkages of structure 4, are exemplified by formula 4a:

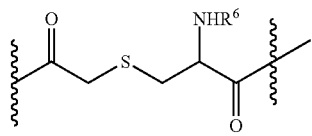

4a wherein, as above, the wavy lines indicate the point of attachment to each of the transport moiety and the biologically active agent. The preparation of conjugates having linking groups of formula 4a are shown in Examples 10-12. In Example 10 (see scheme in FIG. 32), acyclovir is acylated with α-chloroacetic anhydride to form the α-chloroacetate ester 32i. Reaction of 32i with a heptamer of D-arginine having an N-terminal cysteine residue, provides the thioether product 32ii. Alternatively, acyclovir can be attached to the C-terminus of a transport moiety using a similar linkage formed between acyclovir α-chloroacetate ester and a heptamer of D-arginine having a C-terminal cysteine residue. In this instance, the cysteine residue is provided on the $r_7$ transport moiety as a C-terminal amide and the linkage has the form:

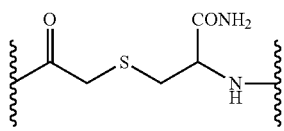 [SMILES: *NC(CSCC(*)=O)C(N)=O]

Accordingly, in one group of preferred embodiments, the conjugate is represented by formula 5, in which X is —OC(O)—; Y is —C(O)NH—; $R^4$ is S; $R^5$ is $NHR^6$; and the subscripts k and m are each 1. In another group of preferred embodiments, the conjugate is represented by formula 2, in which X is —OC(O)—; Y is —NHC(O)—; $R^4$ is S; $R^5$ is $CONH_2$; and the subscripts k and m are each 1. Particularly preferred conjugates are those in which $R^6$ is hydrogen, methyl, allyl, butyl or phenyl.

Linking groups represented by the conjugates shown in formula 6 are generally of the heterobifunctional type (e.g., ε-aminocaproic acid, serine, homoserine, γ-aminobutyric acid, and the like), although suitably protected dicarboxylic acids or diamines are also useful with certain biological agents.

For structure 6, the following substituents are preferred: $R^5$ is $NHR^6$, wherein $R^6$ is hydrogen, methyl, allyl, butyl or phenyl; k is 2; X is —C(O)O—; and Y is —C(O)NH—.

Self-immolating linkers typically undergo intramolecular cleavage with a half-life between about 10 minutes and about 24 hours in water at 37° C. at a pH of approximately 7.4. Preferably, the cleavage half-life is between about 20 minutes and about 4 hours in water at 37° C. at a pH of approximately 7.4. More preferably, the cleavage half-life is between about 30 minutes and about 2 hours in water at 37° C. at a pH of approximately 7.4.

For a conjugate having the structure 3, one can adjust the cleavage half-life by varying the $R^2$ substituent. By using an $R^2$ of increased or decreased size, one can obtain a conjugate having a longer or shorter half-life respectively. $R^2$ in structure 3 is preferably methyl, ethyl, propyl, butyl, allyl, benzyl or phenyl.

Where there is a basic or acidic group in a self-immolating linker, one can oftentimes adjust cleavage half-life according to the pH of the conjugate solution. For instance, the backbone amine group of structure 3 is protonated at acidic pH (e.g., pH 5.5). The amine cannot serve as a nucleophile inducing intramolecular cleavage when it is protonated. Upon introduction of the conjugate into a medium at physiological pH (7.4), however, the amine is unprotonated a significant portion of the time. The cleavage half-life is correspondingly reduced.

In one embodiment, cleavage of a self-immolating linker occurs in two steps: intramolecular reaction of a nucleophilic group resulting in the cleavage of a portion of the linking moiety; and, elimination of the remaining portion of the linking moiety. The first step of the cleavage is rate-limiting and can be fine-tuned for pH sensitivity and half-life.

Structure 6 is an example of a two-step, self-immolating moiety that is incorporated into a transport moiety-biologically active compound conjugate:

6

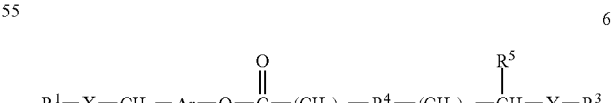

wherein: $R^1$ is the biologically active compound; X represents a linkage between a functional group on the biologically active compound and a functional group on the linking moiety; Ar is a substituted or unsubstituted aryl group, wherein the methylene substituent and phenolic oxygen atom are either ortho or para to one another; $R^3$ is the transport moiety; $R^4$ is S, O, $NR^6$ or $CR^7R^8$; $R^5$ is H, OH, SH or $NHR^6$; $R^6$ is hydrogen, alkyl, aryl, arylalkyl, acyl or allyl; $R^7$ and $R^8$ are independently hydrogen or alkyl; and, k and m are independently either 1 or 2.

An example of a suitable linking group to produce a conjugate of formula 6 is:

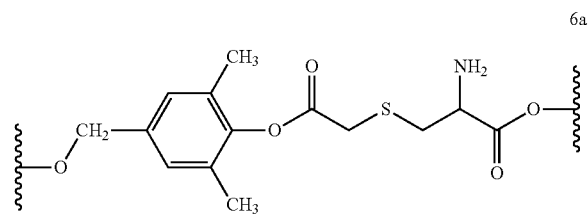 [SMILES: *OCc1cc(C)c(OC(=O)CSCC(N)C(=O)O*)c(C)c1]

6a

The construction of a conjugate containing a linking group of formula 6a is provided in Example 14 (see also FIG. 34). In this example (and Figure), the α-chloroacetate ester of 2,4-dimethyl-4-hydroxymethylphenol (34i) is coupled to retinoic acid (34ii) using dicyclohexylcarbodiimide (DCC) and 4-dimethylaminopyridine (DMAP) to provide the intermediate 34iii. Subsequent coupling of 34iii with a cysteine residue present on the N-terminus of an arginine heptamer transport moiety provides the target conjugate 34iv.

Preferably, the linking groups used in the conjugates of formula 6, are those in which Ar is an substituted or unsubstituted phenylene group; $R^4$ is S; $R^5$ is $NHR^6$, wherein $R^6$ is hydrogen, methyl, allyl, butyl, acetyl or phenyl; k and m are 1; X is —C(O)O—; and Y is —C(O)O— or —C(O)NH—. More preferably, $R^6$ is hydrogen or acetyl.

While linking groups above have been described with reference to conjugates containing arginine heptamers, one of skill in the art will understand that the technology is readily adapted to conjugates with the "spaced" arginine transport moieties of the present invention.

Still other useful linking groups for use in the present invention have been described in copending PCT applications. See, for example PCT applications US98/10571 (Publication No. WO 9852614) and US00/23440 (Publication No. WO01/13957) which describe linking groups for similar compositions, e.g., conjugates of biologically active agents and transport oligomers. The linking technology described therein can be used in the present compositions in a similar manner.

Thus, in one group of embodiments, the linking moiety contains a first cleavable group distal to the biologically active compound and a second cleavable group proximal to the biologically active compound. Cleavage of the first cleavable group yields a nucleophile capable of reacting intramolecularly with the second cleavable group, thereby cleaving the linking moiety from the biologically active compound. Examples of methods by which the first group is cleaved include photo-illumination and enzyme mediated hydrolysis. This methodology has been illustrated for various related small molecule conjugates discussed in PCT application US98/10571 (Publication No. WO 9852614).

Figure 5A:
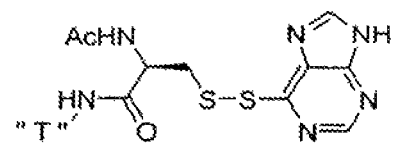

In one approach, the conjugate can include a disulfide linkage, as illustrated in FIG. 5A of PCT application US00/23440 (Publication No. WO01/13957)), (see also, PCT application US98/10571 (Publication No. WO 9852614)), which shows a conjugate (I) containing a transport polymer T which is linked to a cytotoxic agent, 6-mercaptopurine, by an N-acetyl-protected cysteine group which serves as a linker. Thus, the cytotoxic agent is attached by a disulfide bond to the 6-mercapto group, and the transport polymer is bound to the cysteine carbonyl moiety via an amide linkage. Cleavage of the disulfide bond by reduction or disulfide exchange results in release of the free cytotoxic agent. A method for synthesizing a disulfide-containing conjugate is provided in Example 9A of PCT application US98/10571. The product described therein contains a heptamer of Arg residues (SEQ ID NO:3) which is linked to 6-mercaptopurine by an N-acetyl-Cys-Ala-Ala linker, where the Ala residues are included as an additional spacer to render the disulfide more accessible to thiols and reducing agents for cleavage within a cell. The linker in this example also illustrates the use of amide bonds, which can be cleaved enzymatically within a cell.

Figure 5B:
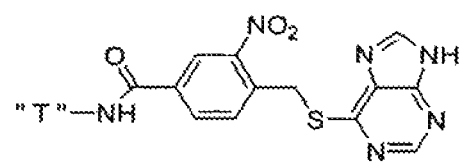

In another approach, the conjugate includes a photocleavable linker that is cleaved upon exposure to electromagnetic radiation. Application of this methodology is provided for a related system in FIG. 5B of PCT application US00/23440 (Publication No. WO01/13957) which shows a conjugate (II) containing a transport polymer T which is linked to 6-mercaptopurine via a meta-nitrobenzoate linking moiety. Polymer T is linked to the nitrobenzoate moiety by an amide linkage to the benzoate carbonyl group, and the cytotoxic agent is bound via its 6-mercapto group to the p-methylene group. The compound can be formed by reacting 6-mercaptopurine with p-bromomethyl-m-nitrobenzoic acid in the presence of $NaOCH_3$/methanol with heating, followed by coupling of the benzoate carboxylic acid to a transport polymer, such as the amino group of a γ-aminobutyric acid linker attached to the polymer (see also, e.g., Example 9B of PCT application US98/10571). Photo-illumination of the conjugate causes release of the 6-mercaptopurine by virtue of the nitro group that is ortho to the mercaptomethyl moiety. This approach finds utility in phototherapy methods as are known in the art, particularly for localizing drug activation to a selected area of the body.

In one group of preferred embodiments, the cleavable linker contains first and second cleavable groups that can cooperate to cleave the oligomer from the biologically active agent, as illustrated by the following approaches. That is, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and oligomer.

Figure 5C:
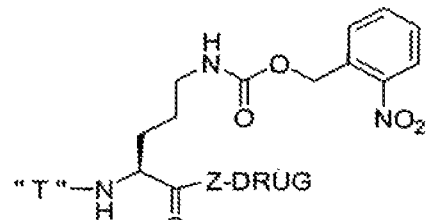

Reference is again made to co-owned and copending PCT application US00/23440 (Publication No. WO01/13957), in which FIG. 5C shows a conjugate (III) containing a transport polymer T linked to the anticancer agent, 5-fluorouracil (5FU). In that figure, the linkage is provided by a modified lysyl residue. The transport polymer is linked to the α-amino group, and the 5-fluorouracil is linked via the α-carbonyl. The lysyl ε-amino group has been modified to a carbamate ester of o-hydroxymethyl nitrobenzene, which comprises a first, photolabile cleavable group in the conjugate. Photo-illumination severs the nitrobenzene moiety from the conjugate, leaving a carbamate that also rapidly decomposes to give the free α-amino group, an effective nucleophile. Intramolecular reaction of the α-amino group with the amide linkage to the 5-fluorouracil group leads to cyclization with release of the 5-fluorouracil group.

Still other linkers useful in the present invention are provided in PCT application US00/23440 (Publication No. WO01/13957). In particular, FIG. 5D of US00/23440 illustrates a conjugate (IV) containing a delivery-enhancing transporter T linked to 2'-oxygen of the anticancer agent, paclitaxel. The linkage is provided by a linking moiety that includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. Enzymatic cleavage of the phosphate group from the conjugate affords a free phenol hydroxyl group. This nucleophilic group then reacts intramolecularly with the carboxylate ester to release free paclitaxel, fully capable of binding to its biological target. Example 9C of PCT application US98/10571 describes a synthetic protocol for preparing this type of conjugate.

Figure 5D:
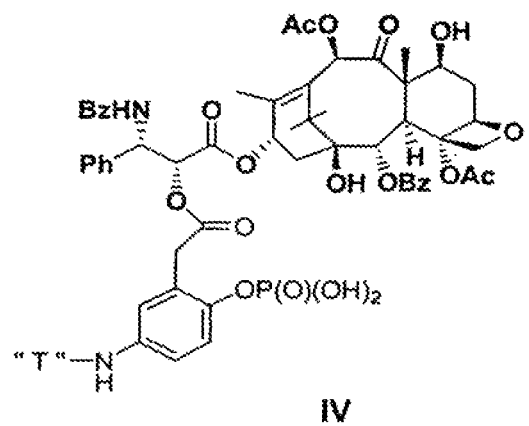
Figure 5E:
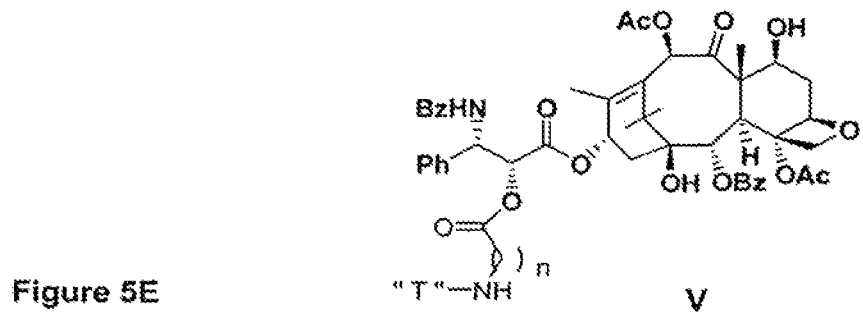

Still other suitable linkers are illustrated in FIG. 5E of PCT application US00/23440 (Publication. No. WO01/13957). In the approach provided therein, a delivery-enhancing transporter is linked to a biologically active agent, e.g., paclitaxel, by an aminoalkyl carboxylic acid. Preferably, the linker amino group is linked to the linker carboxyl carbon by from 3 to 5 chain atoms (n=3 to 5), preferably either 3 or 4 chain atoms, which are preferably provided as methylene carbons. As seen in FIG. 5E, the linker amino group is joined to the delivery-enhancing transporter by an amide linkage, and is joined to the paclitaxel moiety by an ester linkage. Enzymatic cleavage of the amide linkage releases the delivery-enhancing transporter and produces a free nucleophilic amino group. The free amino group can then react intramolecularly with the ester group to release the linker from the paclitaxel.

In another approach, the conjugate includes a linker that is labile at one pH but is stable at another pH. For example, FIG. 6 of PCT application US00/23440 (Publication No. WO01/13957) illustrates a method of synthesizing a conjugate with a linker that is cleaved at physiological pH but is stable at acidic pH. Preferably, the linker is cleaved in water at a pH of from about 6.6 to about 7.6. Preferably the linker is stable in water at a pH from about 4.5 to about 6.5.

Synthesis of other cleavable linkers and conjugates are described in, e.g., U.S. Pat. No. 6,306,993, issued Oct. 23, 2001.

Uses of Delivery-Enhancing Transporters

The delivery-enhancing transporters find use in therapeutic, prophylactic and diagnostic applications. The delivery-enhancing transporters can carry a diagnostic or biologically active reagent into and across one or more layers of epithelial tissue (e.g., ocular and the like). This property makes the reagents useful for treating conditions by delivering agents that must penetrate across one or more tissue layers in order to exert their biological effect.

Moreover, the transporters of the present invention can also be used alone, or in combination with another therapeutic or other compound, as a furin inhibitor. For example, in addition to various poly-arginine transporters, the synthetic transporters described herein, including peptoid and those transporters comprising non-naturally occurring amino acids can be used to inhibit furins. See, e.g., Cameron et al., *J. Biol. Chem.* 275(47): 36741-9. Furins are proteases that convert a variety of pro-proteins to their active components. Inhibition of furins is useful, for instance, for treating infections by viruses that rely on furin activity for virulence or replication. See, e.g., Molloy, et al., *T. Cell Biol.* 9:28-35 (1999).

Similarly, the transporters of the invention are useful inhibitors of capthesin C. For example, certain poly arginine compounds are inhibitors of capthesin C. See, e.g., Horn, et al., *Eur. J. Biochem.* 267(11):3330-3336 (2000). Similarly, the transporters of the invention, including those comprising synthetic amino acids, are useful to inhibit capthesin C.

Compositions and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable pharmaceutical excipient as necessary can be carried out via any of the accepted modes of administration. Thus, administration can be, for example, topical, by intraocular injection, intravenous, subcutaneous, transcutaneous, intramuscular, oral, intra-joint, parenteral, peritoneal, intranasal, or by inhalation. Suitable sites of administration thus include, but are not limited to eye, skin or gastrointestinal tract (e.g., by mouth). The formulations may take the form of solid, semi-solid, lyophilized powder, or liquid dosage forms, such as, for example, tablets, pills, capsules, powders, solutions, suspensions, emulsions, creams, ointments, lotions, aerosols, eye drops, nasal spray or the like, preferably in unit dosage forms suitable for simple administration of precise dosages. See, e.g., Clinical Ophthalmic Pharmacology (Limberts & Potter, eds., 1987); Principles of Internal Medicine (Fauci et al., eds. 1998).

The compositions can include a conventional pharmaceutical carrier or excipient and may additionally include other medicinal agents, carriers, adjuvants, and the like. Preferably, the composition will be about 0.1% to 75% by weight of a compound or compounds of the invention, with the remainder consisting of suitable pharmaceutical excipients. Appropriate excipients can be tailored to the particular composition and route of administration by methods well known in the art, e.g., Remington's Pharmaceutical Sciences, 18th Ed., Mack Publishing Co., Easton, Pa. (1990).

The aqueous suspensions of the present invention may contain, e.g., compounds such as a buffer (e.g. carbonate salt, phosphate salt, acetate salt, glutamic acid, citrate salt, ε-aminocaproic acid), an isotonizing agent (e.g., glycerol, mannitol, sorbitol, propylene glycol, sodium chloride, potassium chloride, boric acid), a stabilizer (e.g., sodium edetate, sodium citrate), a surfactant (e.g., polysorbate 80, polyoxyethylene (60) hydrogenated castor oil, tyloxapol, benzalkonium chloride, polyoxyethylene fatty acid esters, polyoxyethylene alkylphenyl ethers, and polyoxyethylene alkyl ethers, mixtures thereof), a preservative (e.g., p-hydroxybenzoate and its analogs, benzalkonium chloride, benzethonium chloride, chlorobutanol), a pH control agent (e.g., hydrochloric acid, sodium hydroxide, phosphoric acid), a surfactant polyoxyethylene fatty acid esters, and other additives.

Eye drops including, e.g., the conjugates of the invention, can also include an isotonic agent added to sterilized purified water, and if required, a preservative, a buffering agent, a stabilizer, a viscous vehicle and the like are added to the solution and dissolved therein. After dissolution, the pH is adjusted with a pH controller to be within a range suitable for use as an ophthalmic medicine, preferably within the range of 4.5 to 8.

Sodium chloride, glycerin, mannitol or the like may be used as the isotonic agent; p-hydroxybenzoic acid ester, benzalkonium chloride or the like as the preservative; sodium hydrogenphosphate, sodium dihydrogenphosphate, boric acid or the like as the buffering agent; sodium edetate or the like as the stabilizer; polyvinyl alcohol, polyvinyl pyrrolidone, polyacrylic acid or the like as the viscous vehicle; and sodium hydroxide, hydrochloric acid or the like as the pH controller For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences, supra.*, and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by the composition and stereochemistry of the backbone and sidechains of the delivery-enhancing transporters. For polypeptide delivery-enhancing transporters, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

A. Ocular Administration

The delivery-enhancing transporters of the invention can be used to enhance administration of drugs through the tissues of the eye and other related tissues such as the eye lid, as well as across the blood-brain, e.g., via the optic nerve. The ocular tissues include the cornea, iris, lens, vitreus, vitreus humor, the optic nerve and the eyelid.

Exemplary conjugates for administration to the eye include, e.g., anti-bacterial compounds, anti-viral compounds, anti-fungal compounds, anti-protozoan compounds, anti-histamines, immunomodulatory compounds, compounds that dilate the pupil, anesthetic compounds, vitreous adduct agents, steroidal antiinflammatory agents, antiinflammatory analgesics, chemotherapeutic agents, hormones, anticataract agents, neovascularization inhibitors, immunosuppressants, protease inhibitors, and aldose reductase inhibitors, corticoid steroids, immunosuppressives, cholinergic agents, anticholinesterase agents, muscaric antagonists, sympathomimetic agents, $\alpha$ and $\beta$ adrenergic antagonists, and anti-angiogenic factors, among others.

Corticosteroids are useful for treating, e.g., inflammatory glaucoma, anterior, intermediate, and posterior uveitis, optic neuritis, Leber's neuroretinitis, retinitis, pseudotumor/myositis, orbital myositis, hemangioma/lymphangioma, toxocariasisl Behcet's panuveitis, inflammatory chorisretinopathies, and vasculitis. Exemplary corticosteroids include, e.g., hydrocortisone, fludrocortisone, triamcinolone, dexamethasone, prednisolone, cortisone, aldosterone, and betamethasone.

Immunosuppressives are useful for treating, e.g., inflammatory glaucoma, anterior, intermediate, and posterior uveitis, optic neuritis, Leber's neuroretinitis, retinitis, pseudotumor/myositis, orbital myositis, hemangioma/lymphangioma, toxocariasis, Behcet's panuveitis, inflammatory chorisretinopathies, vasculitis, and dry eye syndrome (Sjogren's syndrome). Dry eye, or "Sjögren's syndrome," is an immune system disorder characterized by inflammation and dryness of the mouth, eyes, and other mucous membranes, damages the lacrimal glands, and this damage affects tear production.

Exemplary immunosuppressives include, e.g., cyclosporins such as cyclosporin A, ascomycins such as FK-506, and nonsteroidal anti-inflammatory agents such as Cox-2 inhibitors, ketorolac, suprofen, and antazoline. Other exemplary immunosuppressives include, e.g., rapamycin and tacrolimus.

Antibacterial agents are useful for treating, e.g., conjunctivitis, styes, blepharitis, and keratitis. Conjunctivitis, sometimes called pink eye, is an inflammation of the blood vessels in the conjunctiva, the membrane that covers the sclera and inside of the eyelids. Conjunctivitis may be caused by bacteria or viruses.

Styes are noncontagious, bacterial infections of one of the sebaceous glands of the eyelid. A stye looks like a small, red bump either on the eyelid or on the edge of the eyelid.

Exemplary antibacterials include, e.g., beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides enoxacin, ofloxacin, cinoxacin, sparfloxacin, thiamphenicol, nalidixic acid, tosufloxacin tosilate, norfloxacin, pipemidic acid trihydrate, piromidic acid, fleroxacin, chlortetracycline, ciprofloxacin, erythromycin, gentamycin, norfloxacin, sulfacetamide, sulfixoxazole, tobramycin, and levofloxacin.

Antiviral agents are useful for treating, e.g., Herpes simplex keratitis, Herpes simplex conjunctivitis, Herpes zoster ophthalmicus and Cytomegalovirus retinitis. Antiviral agents include, e.g., acyclovir, ganciclovir, didanosine, didovudine, idoxuridine, trifluridine, foscarnet, and vidarabine.

Antifungal agents are useful for treating, e.g., fungal keratitis and fungal endophthalmitis. Antifungal agents include, among others, polyenes such as amphotericin B and natamycin; imidazoles such as clotrimazole, miconazole, ketoconazole, fluconazole and econazole; and pyrimidines such as flucytosine. Other exemplary antifungal agents included, e.g., itraconazole, flucytosine and pimaricin.

Antiparasitic compounds and/or anti-protozoal compounds include, e.g., ivermectin, pyrimethamine, trisulfapidimidine, clindamycin and corticosteroid preparations.

Cholinergic agents are useful for treating, e.g., glaucoma and corneal edema. Exemplary cholinergic agents include, e.g., acetylcholine, carbachol, and pilocarpine.

Anticholinesterase agents are useful for treating, e.g., glaucoma and accommodative esotropia. Exemplary anticholinesterase agents include, e.g., physostigmine, demecarium, echothiophate, and isofluorophate.

Muscaric antagonists are useful for treating, e.g., cycloplegic retinoscopy and cycloplegia. They are also useful in dilated fundoscopic exams. Exemplary muscaric antagonists include, e.g., atropine, scopolamine, homatropine, cyclopentolate, and tropicamide.

Sympathomimetic agents are useful for treating, e.g., glaucoma and mydriasis. Exemplary sympathomimetic agents include, e.g., dipivefrin, epinephrine, phenylephrine, apraclonidine, cocaine, hydroxyamphetamine, naphazoline, and tetrahydrozoline.

α and β adrenergic antagonists are useful for treating, e.g., glaucoma and reverse mydriasis. Exemplary α and β adrenergic antagonists include, e.g., dapiprazole, betaxolol, carteolol, levobunolol, metipranolol, and timolol.

Antiangiogenic factors are useful for treating, e.g., macular degeneracy. Exemplary antiangiogenic factors include, e.g., corticosteroids, thalidomide, and estradiols.

Antihistamines and decongestants include, e.g., pyrilamine, chlorpheniramine, tetrahydrazoline, antazoline and analogs thereof; mast-cell inhibitors of histamine release, such as cromolyn.

Antiinflammatory analgesics include, among others, alclofenac, aluminopropfen, ibuprofen, indomethacin, epirizole, oxaprozin, ketoprofen, diclofenac sodium, diflunisal, naproxen, piroxicam, fenbufen, flufenamic acid, flurbiprofen, floctafenine, pentazocine, metiazinic acid, mefenamic acid and mofezolac.

Other anesthetic agents include, e.g., cocaine, etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine.

Chemotherapeutic agents include, among others, sulfa drugs such as salazusulfapyridine, sulfadimethoxine, sulfamethizole, sulfamethoxazole, sulfamethopyrazine and sulfamonomethoxine.

Hormones include, among others, insulin zinc, testosterone propionate and estradiol benzoate.

Anticataract agents include, among others, pirenoxine and the like.

Neovascularization inhibitors include, among others, fumagillin and derivatives thereof.

Protease inhibitors include, among others, [L-3-transethoxycarbonyloxiran-2-carbonyl]-L-leucine (3-methylbutyl)amide (E-64-d) and the like.

Aldose reductase inhibitors include, among others, 5-(3-ethoxy-4-pentyloxyphenyl)thiazolidine-2,4-dione and the like.

Several classes of agents discussed above can be used to treat glaucoma. Glaucoma is a condition in which the normal fluid pressure inside the eyes (intraocular pressure, or IOP) slowly rises as a result of the fluid aqueous humor, which normally flows in and out of the eye, not being able to drain properly. Instead, the fluid collects and causes pressure damage to the optic nerve and loss of vision. Useful compounds to treat glaucoma, blindness, and other eye disorders include, e.g., timolol, levobunolol and phenylepherine. Growth factors such as nerve growth factor (NGF) (see, e.g., Bennett, et al. *Mol Ther* 1(6):501-5 (2000)) are also useful for treating glaucoma and other ocular disorders. Antiglaucoma drugs, in addition to those discussed above, include, e.g., timalol, and its maleic salt and R-timolol and a combination of timolol or R-timolol with pilocarpine, as well as many other adrenergic agonists and/or antagonists: epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thiothiophenesulfonamide, 6-hydroxy-2-benzothiazolesulfonamide, and 6-pivaloyloxy-2-benzothiazolesulfonamide.

Therapeutic compounds for treatment of ocular diseases, such as those discussed above, are well known to those of skill in the art. Typically, administration of the composition of the invention to the ocular tissues is in the form of an eye drop. Alternatively, for example, the compositions can be injected into the eye or applied as an ointment.

B. Diagnostic Imaging and Contrast Agents

The delivery-enhancing transporters of the invention are also useful for delivery of diagnostic imaging and contrast agents into and across one or more layers of ocular epithelial or endothelial tissue and within the eye and eye lid in general. Examples of diagnostic agents include substances that are labeled with radioactivity, such as $^{99}$mTc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell (including, but not limited to, (β-galactosidase, green fluorescent protein, luciferase, and the like, as well as those compounds used to examine the retina, such as sodium fluorescein; those used to examine the conjunctiva, cornea and lacrimal apparatus, such as fluorescein and rose bengal; and those used to examine abnormal pupillary responses such as methacholine, cocaine, adrenaline, atropine, hydroxyamphetamine and pilocarpine. A wide variety of labels may be employed, such as radionuclides, fluors, enzymes, enzyme substrates, enzyme cofactors, enzyme inhibitors, ligands (particularly haptens), etc.

Biologically Active and Diagnostic Molecules Useful with Delivery-Enhancing Transporters The delivery-enhancing transporters can be conjugated to a wide variety of biologically active agents and molecules that have diagnostic use.

A. Small Organic Molecules

Small organic molecule therapeutic agents can be advantageously attached to linear polymeric compositions as described herein, to facilitate or enhance transport across one or more layers of an epithelial or endothelial tissue. For example, delivery of highly charged agents, such as levodopa (L-3,4-dihydroxy-phenylalanine; L-DOPA) may benefit by linkage to delivery-enhancing transporters as described herein. Peptoid and peptidomimetic agents are also contemplated (e.g., Langston (1997) DDT 2:255; Giannis et al. (1997) *Advances Drug Res.* 29:1). Also, the invention is advantageous for delivering small organic molecules that have poor solubilities in aqueous liquids, such as serum and aqueous saline. Thus, compounds whose therapeutic efficacies are limited by their low solubilities can be administered in greater dosages according to the present invention, and can be more efficacious on a molar basis in conjugate form, relative to the non-conjugate form, due to higher uptake levels by cells.

Since a significant portion of the topological surface of a small molecule is often involved, and therefore required, for biological activity, the small molecule portion of the conjugate in particular cases may need to be severed from the attached delivery-enhancing transporter and linker moiety (if any) for the small molecule agent to exert biological activity after crossing the target epithelial tissue. For such situations, the conjugate preferably includes a cleavable linker for releasing free drug after passing through an epithelial tissue.

FIG. 5D and FIG. 5E are illustrative of another aspect of the invention, comprising taxane- and taxoid anticancer conjugates which have enhanced trans-epithelial tissue transport rates relative to corresponding non-conjugated forms. The conjugates are particularly useful for inhibiting growth of cancer cells. Taxanes and taxoids are believed to manifest their anticancer effects by promoting polymerization of microtubules (and inhibiting depolymerization) to an extent that is deleterious to cell function, inhibiting cell replication and ultimately leading to cell death.

Figure 5F:
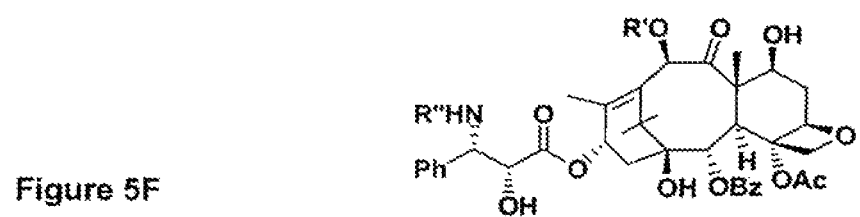
Figure 5G:
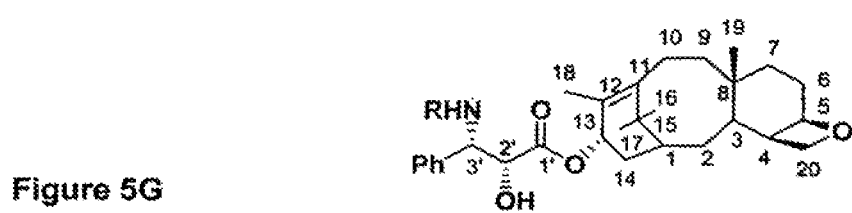
Figure 5H:

The term "taxane" refers to paclitaxel (FIG. 5F, R'=acetyl, R"=benzyl) also known under the trademark "TAXOL") and naturally occurring, synthetic, or bioengineered analogs having a backbone core that contains the A, B, C and D rings of paclitaxel, as illustrated in FIG. 5G. FIG. 5F also indicates the structure of "TAXOTERE™" (R'=H, R"=BOC), which is a somewhat more soluble synthetic analog of paclitaxel sold by Rhone-Poulenc. "Taxoid" refers to naturally occurring, synthetic or bioengineered analogs of paclitaxel that contain the basic A, B and C rings of paclitaxel, as shown in FIG. 5H. Substantial synthetic and biological information is available on syntheses and activities of a variety of taxane and taxoid compounds, as reviewed in Suffness (1995) *Taxol: Science and Applications*, CRC Press, New York, N.Y., pp. 237-239, particularly in Chapters 12 to 14, as well as in the subsequent paclitaxel literature. Furthermore, a host of cell lines are available for predicting anticancer activities of these compounds against certain cancer types, as described, for example, in Suffness at Chapters 8 and 13.

The delivery-enhancing transporter is conjugated to the taxane or taxoid moiety via any suitable site of attachment in the taxane or taxoid. Conveniently, the transport polymer is linked via a C2'-oxygen atom, C7-oxygen atom, using linking strategies as above. Conjugation of a transport polymer via a C7-oxygen leads to taxane conjugates that have anticancer and antitumor activity despite conjugation at that position. Accordingly, the linker can be cleavable or non-cleavable. Conjugation via the C2'-oxygen significantly reduces anti-cancer activity, so that a cleavable linker is preferred for conjugation to this site. Other sites of attachment can also be used, such as C10.

It will be appreciated that the taxane and taxoid conjugates of the invention have improved water solubility relative to taxol (0.25 μg/mL) and taxotere (6-7 μg/mL). Therefore, large amounts of solubilizing agents such as "CREMOPHOR EL" (polyoxyethylated castor oil), polysorbate 80 (polyoxyethylene sorbitan monooleate, also known as "TWEEN 80"), and ethanol are not required, so that side-effects typically associated with these solubilizing agents, such as anaphylaxis, dyspnea, hypotension, and flushing, can be reduced.

B. Metals

Metals can be transported into and across one or more layers of ocular epithelia and endothelia using chelating agents such as texaphyrin or diethylene triamine pentacetic acid (DTPA), conjugated to a delivery-enhancing transporter of the invention, as illustrated in the examples. These conjugates are useful for delivering metal ions for imaging or therapy. Exemplary metal ions include Eu, Lu, Pr, Gd, Tc99m, Ga67, In111, Y90, Cu67, and Co57. Preliminary membrane-transport studies with conjugate candidates can be performed using cell-based assays such as described in the Example section below. For example, using europium ions, cellular uptake can be monitored by time-resolved fluorescence measurements. For metal ions that are cytotoxic, uptake can be monitored by cytotoxicity.

C. Macromolecules

The enhanced transport methods of the invention are particularly suited for enhancing transport into and across one or more layers of an epithelial or endothelial tissue for a number of macromolecules, including, but not limited to proteins, nucleic acids, polysaccharides, and analogs thereof. Exemplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Analogs include charged and preferably uncharged backbone analogs, such as phosphonates (preferably methyl phosphonates), phosphoramidates (N3' or N5'), thiophosphates, uncharged morpholino-based polymers, and protein nucleic acids (PNAs). Such molecules can be used in a variety of therapeutic regimens, including enzyme replacement therapy, gene therapy, and anti-sense therapy, for example.

By way of example, protein nucleic acids (PNA) are analogs of DNA in which the backbone is structurally homomorphous with a deoxyribose backbone. The backbone consists of N-(2-aminoethyl)glycine units to which the nucleobases are attached. PNAs containing all four natural nucleobases hybridize to complementary oligonucleotides obeying Watson-Crick base-pairing rules, and is a true DNA mimic in terms of base pair recognition (Egholm et al. (1993) *Nature* 365:566-568). The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport polymer of the invention.

Figure 7:
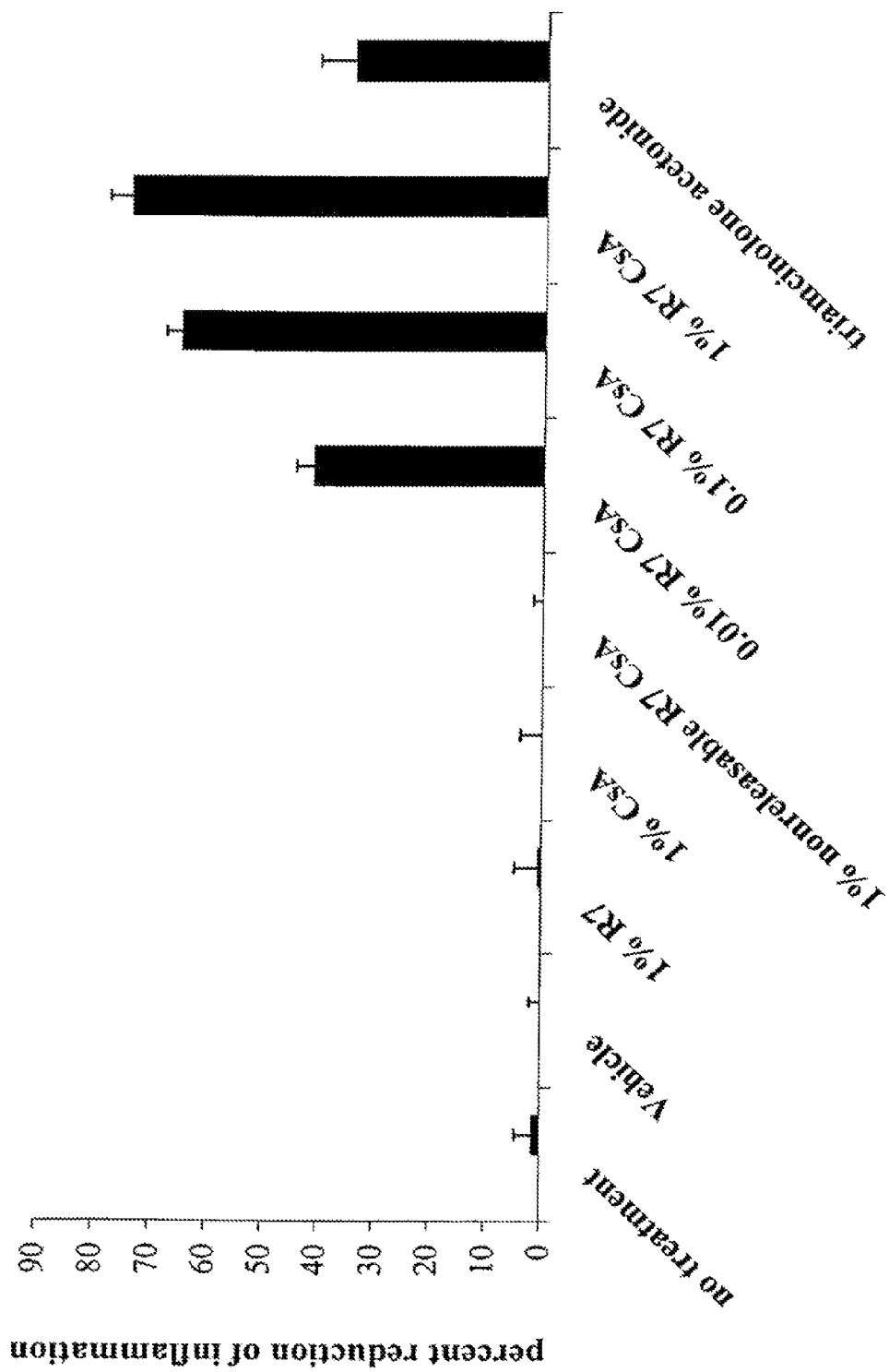

Examples of anti-sense oligonucleotides whose transport into and across epithelial and endothelial tissues can be enhanced using the methods of the invention are described, for example, in U.S. Pat. No. 5,594,122. Such oligonucleotides are targeted to treat human immunodeficiency virus (HIV). Conjugation of a transport polymer to an anti-sense oligonucleotide can be effected, for example, by forming an amide linkage between the peptide and the 5'-terminus of the oligonucleotide through a succinate linker, according to well-established methods. The use of PNA conjugates is further illustrated in Example 11 of PCT Application PCT/US98/10571. FIG. 7 of that application shows results obtained with a conjugate of the invention containing a PNA sequence for inhibiting secretion of gamma-interferon (γ-IFN) by T cells, as detailed in Example 11. As can be seen, the anti-sense PNA conjugate was effective to block γ-IFN secretion when the conjugate was present at levels above about 10 µM. In contrast, no inhibition was seen with the sense-PNA conjugate or the non-conjugated antisense PNA alone.

Another class of macromolecules that can be transported across one or more layers of an epithelial or endothelial tissue is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetylglucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuromuscular dysfunction associated with triose phosphate isomerase deficiency.

In addition, and according to an important aspect of the invention, protein antigens may be delivered to the cytosolic compartment of antigen-presenting cells (APCs), where they are degraded into peptides. The peptides are then transported into the endoplasmic reticulum, where they associate with nascent HLA class 1 molecules and are displayed on the cell surface. Such "activated" APCs can serve as inducers of class I restricted antigen-specific cytotoxic T-lymphocytes (CTLs), which then proceed to recognize and destroy cells displaying the particular antigen. APCs that are able to carry out this process include, but are not limited to, certain macrophages, B cells and dendritic cells. In one embodiment, the protein antigen is a tumor antigen for eliciting or promoting an immune response against tumor cells. The transport of isolated or soluble proteins into the cytosol of APC with subsequent activation of CTL is exceptional, since, with few exceptions, injection of isolated or soluble proteins does not result either in activation of APC or induction of CTLs. Thus, antigens that are conjugated to the transport enhancing compositions of the present invention may serve to stimulate a cellular immune response in vitro or in vivo.

In another embodiment, the invention is useful for delivering immunospecific antibodies or antibody fragments to the cytosol to interfere with deleterious biological processes such as microbial infection. Recent experiments have shown that intracellular antibodies can be effective antiviral agents in plant and mammalian cells (e.g., Tavladoraki et al. (1993) Nature 366:469; and Shaheen et al. (1996) J. Virol. 70:3392. These methods have typically used single-chain variable region fragments (scFv), in which the antibody heavy and light chains are synthesized as a single polypeptide. The variable heavy and light chains are usually separated by a flexible linker peptide (e.g., of 15 amino acids) to yield a 28 kDa molecule that retains the high affinity ligand binding site. The principal obstacle to wide application of this technology has been efficiency of uptake into infected cells. But by attaching transport polymers to scFv fragments, the degree of cellular uptake can be increased, allowing the immunospecific fragments to bind and disable important microbial components, such as HIV Rev, HIV reverse transcriptase, and integrase proteins.

D. Peptides

Peptides to be delivered by the enhanced transport methods described herein include, but should not be limited to, effector polypeptides, receptor fragments, and the like. Examples include peptides having phosphorylation sites used by proteins mediating intracellular signals. Examples of such proteins include, but are not limited to, protein kinase C, RAF-1, p21Ras, NF-κB, C-JUN, and cytoplasmic tails of membrane receptors such as IL-4 receptor, CD28, CTLA-4, V7, and MHC Class I and Class II antigens.

When the delivery-enhancing transporter is also a peptide, synthesis can be achieved either using an automated peptide synthesizer or by recombinant methods in which a polynucleotide encoding a fusion peptide is produced, as mentioned above.

EXAMPLES

The following examples are offered to illustrate, but not to limit the present invention.

Example 1

Ocular Delivery of Transporter Conjugates

The ability of the transporters of the invention to penetrate the tissues of the eye was examined. Biotinylated r8 was both injected into the eyes of rabbits and also applied as eyedrops to the outside of the eye.

Briefly, 5 drops of a 1 mM solution of biotinylated r8 in PBS was applied to both eyes of a rabbit and allowed to incubate 15 minutes. The animal was sacrificed and one eye was dissected intact with adjacent tissue, whereas the other was separated into each of its component parts, frozen and separately sectioned, stained with streptavidin-fluorescein and counterstained with propidium iodide. Results demonstrated staining in the cornea and eyelid, but not the lens.

Fifty microliters of a 10 mM solution of biotinylated r8 in PBS was injected into the vitreus humor of another animal and the animal was sacrificed 30 minutes later and the injected eye was dissected. Again one orbital was frozen intact while the other was dissected and the components separately frozen. Results from the injection experiments demonstrated that all interior surfaces of the orb were stained.

Example 2

Figure 10:
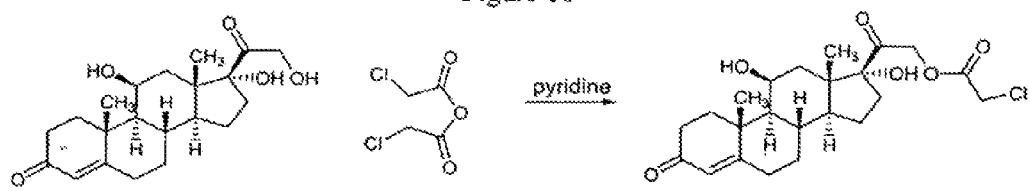
FIG. 10 shows a reaction for the acylation of hydrocortisone with chloroacetic anhydride.

Synthesis, In Vitro and In Vivo Activity of a Releasable Conjugate of a Short Oligomer of Arginine and CsA Modification of the 2° alcohol of Cyclosporin A results in significant loss of its biological activity. See, e.g., R. E. Handschumacher, et al., Science 226, 544-7 (1984). Consequently, to ensure release of free Cyclosporin A from its conjugate after transport into cells, Cyclosporin A was conjugated to an oligo-arginine transporter through a pH sensitive linker as shown in FIG. 10. The resultant conjugate is stable at acidic pH but at pH>7 it undergoes an intramolecular cyclization involving addition of the free amine to the carbonyl adjacent to Cyclosporin A (FIG. 6), which results in the release of unmodified Cyclosporin A.

Another modification in the design of the releasable conjugate was the use of L-arginine (R), and not D-arginine (r) in the transporter. While the oligo-D-arginine transporters were used for the histological experiments to ensure maximal stability of the conjugate and therefore accuracy in determining its location through fluorescence, oligomers of L-arginine were incorporated into the design of the releasable conjugate to minimize its biological half-life. Consistent with its design, the resultant releasable conjugate was shown to be stable at acidic pH, but labile at physiological pH in the absence of serum. This releasable Cyclosporin A conjugate's half-life in pH 7.4 PBS was 90 minutes.

Results

The releasable guanidino-heptamer conjugate of Cyclosporin A was shown to be biologically active by inhibiting IL-2 secretion by the human T cell line, Jurkat, stimulated with PMA and ionomycin in vitro. See R. Wiskocil, et al., *J Immunol* 134, 1599-603 (1985). The conjugate was added 12 hours prior to the addition of PMA/ionomycin and dose dependent inhibition was observed by the releasable R7 CsA conjugate. This inhibition was not observed with a non-releasable analog (FIG. 6) that differed from the releasable conjugate by retention of the t-Boc protecting group, which prevented cyclization and resultant release of the active drug. The $EC_{50}$ of the releasable R7 cyclosporin conjugate was approximately two fold higher than CsA dissolved in alcohol and added at the same time as the releasable conjugate.

The releasable R7 CsA conjugate was assayed in vivo for functional activity using a murine model of contact dermatitis. Treatment with the 1% releasable R7 CSA conjugate resulted in 73.9%±4.0 reduction in ear inflammation (FIG. 7). No reduction in inflammation was seen in the untreated ear, indicating that the effect seen in the treated ear was local and not systemic. Less inhibition was observed in the ears of mice treated with 0.1 and 0.01% R7-CsA (64.8%±4.0 and 40.9%±3.3 respectively), demonstrating that the effect was titratable. Treatment with the fluorinated corticosteroid positive control resulted in reduction in ear swelling (34.1%±6.3), but significantly less than that observed for 0.1% releasable R7 CsA (FIG. 7). No reduction of inflammation was observed in any of the mice treated with unmodified Cyclosporin A, vehicle alone, R7 (SEQ ID NO:3), or nonreleasable R7 CsA.

Example 3

The Preparation of Copper and Gadolinium-DTPA-r7 Complexes

Methods

1. Preparation of Metal Complexes

Step 1—Preparation of Copper-Diethylenetriaminepentaacetic Acid Complex (Cu-DTPA)

Figure 8:
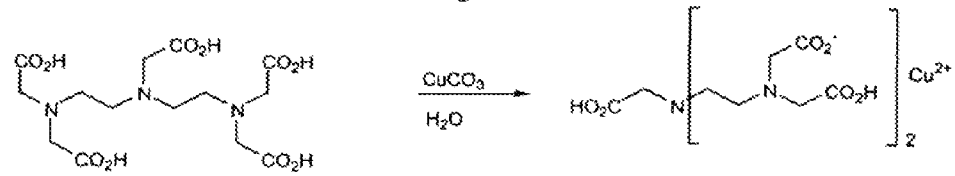
FIG. 8 shows a procedure for the preparation of a copper-diethylenetriaminepentaacetic acid complex (Cu-DTPA).

Copper carbonate (10 mmol) and diethylenetriaminpentacetic acid (10 mmol) were dissolved in water (150 mL) (FIG. 8). After 18 h, the solution was centrifuged to removed any solids. The blue solution was decanted and lyophilized to provide a blue powder (yields>90%).

Step 2—Preparation of DTPA Transporter

Figure 9:
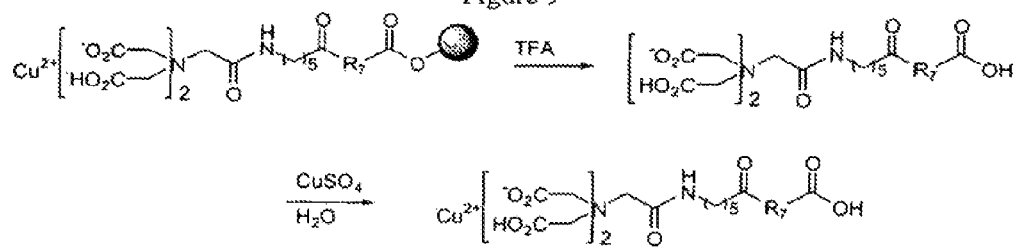
FIG. 9 shows a procedure for linking the Cu-DTPA to a transporter (SEQ ID NOS:70-72) through an aminocaproic acid.

The Cu-DTPA was linked to a transporter through an aminocaproic acid spacer using a PE Applied Biosystems Peptide Synthesizer (ABI 433A) (FIG. 9). The material was cleaved from the resin by treatment with trifluoroacetic acid (TFA) (40 mL), triisopropyl silane (100 µL) and phenol (100 µL) for 18 h. The resin was filtered off and the peptide was precipitated by addition of diethyl ether (80 mL). The solution was centrifuged and the solvent decanted off. The crude solid was purified by reverse-phase HPLC using a water/acetonitrile gradient. Treatment with TFA resulted in loss of $Cu^{2+}$ ion which needed to be reinserted.

DTPA-aca-R7-CO2H (SEQ ID NO:31) (10 mg, 0.0063 mmol) and copper sulfate (1.6 mg, 0.0063 mmol) were dissolved in water (1 mL). Let gently stir for 18 h and lyophilized to provide product as a white powder (10 mg).

2. Analysis of Transport Across Skin

Metal diethylenetriaminepentaacetic acid (DTPA) complexes were formed by mixing equimolar amounts of metal salts with DTPA in water for 18 hours. At the end of this time, the solutions were centrifuged, frozen and lyophilized. The dried powder was characterized by mass spectrometry and used in solid phase peptide synthesis. The metal-DTPA complexes were attached to polymers of D- or L-arginine that were still attached to solid-phase resin used in peptide synthesis. The metal-DTPA complexes were attached using an aminocaproic acid spacer.

Peptides were synthesized using solid phase techniques and commercially available Fmoc amino acids, resins, and reagents (PE Biosystems, Foster City Calif., and Bachem Torrence, Calif.) on a Applied Biosystems 433 peptide synthesizer. Fastmoc cycles were used with O-(7-azabenzotriazol-1-yl)-1,1,3,3-tetramethyluronium hexyluorophosphate (HATU) substituted for HBTU/HOBt as the coupling reagent. Prior to the addition of biotin to the amino terminus of the peptide, amino caproic acid (aca) was conjugated and acted as a spacer. The peptides were cleaved from the resin using 96% trifluoroacetic acid, 2% triisopropyl silane, and 2% phenol for between 1 and 12 hours, also releasing the metal. The longer reaction times were necessary to completely remove the Pbf protecting groups from the polymers of arginine. The peptides subsequently were filtered from the resin, precipitated using diethyl ether, purified using HPLC reverse phase columns (Alltech Altima, Chicago, Ill.) and characterized using either electrospray or matrix assisted laser desorption mass spectrometry (Perceptive Biosystems, Boston, Mass.).

The metal is replaced after HPLC purification and lyophilization of the peptide-DTPA complex. Replacement of the metal involved incubation of equimolar amounts of the metal salt with the peptide-aminocaproic acid-DTPA complex and subsequent lyophilization.

Example 4

Conjugate of Taxol and Delivery-Enhancing Transporter with pH-Releasable Linker

This Example demonstrates the use of a general strategy for synthesizing prodrugs that have a delivery-enhancing transporter linked to a drug by a linker that releases the drug from the delivery-enhancing transporter upon exposure to physiological pH. In general, a suitable site on the drug is derivatized to carry an α-chloroacetyl residue. Next, the chlorine is displaced with the thiol of a cysteine residue that carries an unprotected amine. This scheme is shown in FIG. 16.

Methods

Synthesis of Taxol-2'-chloroacetyl

Taxol (89.5 mg, 104.9 µmol) was dissolved in $CH_2Cl_2$ (3.5 mL). The solution was cooled to 0° C. under an $N_2$-atmosphere. α-Chloroacetic anhydride (19.7 mg, 115.4 µmol) was added, followed by DIEA (14.8 mg, 115.4 µmol). The solution was allowed to warm to room temperature. After thin layer chromatography (tlc) analysis indicated complete consumption of starting material, the solvent was removed in vacuo and the crude material was purified by flash chromatography on silica gel (eluent: EtOAC/Hex 20%-50%) yielding the desired material (99.8 mg, quantitative) (FIG. 18).

$^1$H-NMR ($CDCl_3$): δ=8.13 (d, J=7.57 Hz, 2H), 7.72 (d, J=7.57 Hz, 2H), 7.62-7.40 (m, 11H), 6.93 (d, J=9.14 Hz, 1H), 6.29-6.23 (m, 2H), 6.01 (d, J=7.14 Hz, 1H), 5.66 (d, J=6.80 Hz, 1H), 5.55 (d, J=2.24 Hz, 1H), 4.96 (d, J=8.79 Hz, 1H), 4.43 (m, 1H), 4.30 (d, J=8.29 Hz, 1H), 4.20-4.15 (m, 2H), 3.81 (d, J=6.71 Hz, 1H), 2.56-2.34 (m, 3H), 2.45 (s, 3H), 2.21 (s, 3H), 2.19 (m, 1H), 1.95-1.82 (m, 3H), 1.92 s, (3H), 1.67 (s, 3H), 1.22 (s, 3H), 1.13 (s, 3H) ppm.

$^{13}$C-NMR ($CDCl_3$): δ=203.6, 171.1, 169.7, 167.3, 167.0, 166.9, 166.3, 142.3, 136.4, 133.6, 133.5, 132.9, 132.0, 130.1, 129.2, 121.1, 128.7, 128.6, 127.0, 126.5, 84.3, 81.0, 79.0, 76.3, 75.4, 75.2, 75.0, 72.2, 72.0, 58.4, 52.7, 45.5, 43.1, 40.1, 35.5, 26.7, 22.6, 22.0, 20.7, 14.7, 9.5 ppm.

Linkage of Taxol to Delivery-Enhancing Transporter

The peptide (47.6 mg, 22.4 µmol) was dissolved in DMF (1.0 mL) under an $N_2$-atmosphere. DIEA (2.8 mg, 22.4 µmol) was added. A solution of taxol-2'-chloroacetate (20.8 mg, 22.4 µmol) in DMF (1.0 mL) was added. Stirring at room temperature was continued for 6 hours. Water containing 0.1% TFA (1.0 mL) was added, the sample was frozen and the solvents were lyophilized. The crude material was purified by RP-HPLC (eluent: water/MeCN*0.1% TFA: 85%-15%). A schematic of this reaction is shown in FIG. 18.

Synthesis of Related Conjugates

Using the conjugation conditions outlined above, the three additional conjugates shown in were synthesized.

Cytotoxicity Assay

The taxol conjugates were tested for cytotoxicity in a 3-(4,5-dimethylthiazol-2-yl)-2,5-diphenyl-tetrazolium-bromide (MTT) dye reduction. Results, which are shown in FIG. 20, demonstrate that the taxol conjugated to r7 with a readily pH-releasable linker (CG 1062; R=Ac in the structure shown in FIG. 19) is significantly more cytotoxic than either taxol alone or taxol conjugated to r7 with a less-readily pH-releasable linker (CG 1040; R=H in the structure shown in FIG. 19).

Example 5

Structure-Function Relationships of Fluorescently-Labeled Peptides Derived from $Tat_{49-57}$ Methods General.

Rink amide resin and $Boc_2O$ were purchased from Novabiochem. Diisopropylcarbodiimide, bromoacetic acid, fluorescein isothiocyanate (FITC-NCS), ethylenediamine, 1,3-diaminopropane, 1,4-diaminobutane, 1,6-diaminohexane, trans-1,6-diaminocyclohexane, and pyrazole-1-carboxamidine were all purchased from Aldrich®. All solvents and other reagents were purchased from commercial sources and used without further purification. The mono-Boc amines were synthesized from the commercially available diamines using a literature procedure (10 equiv. of diamine and 1 equiv. of $Boc_2O$ in chloroform followed by an aqueous work up to remove unreacted diamine) (34).

N-tert-butoxycarbonyl-1,6-trans-diaminocyclohexane

Mp 159-161° C.; $^1H$ NMR ($CDCl_3$) δ 4.35 (br s, 1H), 3.37 (br s, 1H), 2.61 (br s, 1H), 1.92-2.02 (m, 2H), 1.81-1.89 (m, 2H), 1.43 (s, 9H), 1.07-1.24 (m, 4H) ppm; $^{13}C$ NMR ($D_6$-DMSO) δ 154.9, 77.3, 49.7, 48.9, 35.1, 31.4, 28.3 ppm; ES-MS (M+1) calcd 215.17. Found 215.22.

General Procedure for Peptide Synthesis.

$Tat_{49-57}$ (RKKRRQRRR; SEQ ID NO:28), truncated and alanine-substituted peptides derived from $Tat_{49-57}$, Antennapedia$_{43-58}$ (RQIKIWFQNRRMKWKK; SEQ ID NO:29), and homopolymers of arginine (R5-R9; SEQ ID NOS:1-5) and d-arginine (r5-r9) were prepared with an automated peptide synthesizer (ABI433) using standard solid-phase Fmoc chemistry (35) with HATU as the peptide coupling reagent. The fluorescein moiety was attached via a aminohexanoic acid spacer by treating a resin-bound peptide (1.0 mmol) with fluorescein isothiocyanate (1.0 mmol) and DIEA (5 mmol) in DMF (10 mL) for 12 h. Cleavage from the resin was achieved using 95:5 TFA/triisopropylsilane. Removal of the solvent in vacuo gave a crude oil which was triturated with cold ether. The crude mixture thus obtained was centrifuged, the ether was removed by decantation, and the resulting orange solid was purified by reverse-phase HPLC ($H_2O/CH_3CN$ in 0.1% TFA). The products were isolated by lyophilization and characterized by electrospray mass spectrometry. Purity of the peptides was >95% as determined by analytical reverse-phase HPLC ($H_2O/CH_3CN$ in 0.1% TFA).

All peptides and peptoids synthesized contain an aminohexanoic (ahx) acid moiety attached to the N-terminal amino group with a fluorescein moiety (Fl) covalently linked to the amino group of the aminohexanoic acid spacer. The carboxyl terminus of every peptide and peptoid is a carboxamide.

Cellular Uptake Assay.

The arginine homopolymers and guanidine-substituted peptoids were each dissolved in PBS buffer (pH 7.2) and their concentration was determined by absorption of fluorescein at 490 nm (ε=67,000). The accuracy of this method for determining concentration was established by weighing selected samples and dissolving them in a known amount of PBS buffer. The concentrations determined by UV spectroscopy correlated with the amounts weighed out manually. Jurkat cells (human T cell line), murine B cells (CH27), or human PBL cells were grown in 10% fetal calf serum and DMEM and each of these were used for cellular uptake experiments. Varying amounts of arginine and oligomers of guanidine-substituted peptoids were added to approximately $3\times10^6$ cells in 2% FCS/PBS (combined total of 200 µL) and placed into microtiter plates (96 well) and incubated for varying amounts of time at 23° C. or 4° C. The microtiter plates were centrifuged and the cells were isolated, washed with cold PBS (3×250 µL), incubated with 0.05% trypsin/0.53 mM EDTA at 37° C. for 5 min, washed with cold PBS, and resuspended in PBS containing 0.1% propidium iodide. The cells were analyzed using fluorescent flow cytometry (FACScan, Becton Dickinson) and cells staining with propidium iodide were excluded from the analysis. The data presented is the mean fluorescent signal for the 5000 cells collected.

Inhibition of Cellular Uptake with Sodium Azide.

The assays were performed as previously described with the exception that the cells used were preincubated for 30 min with 0.5% sodium azide in 2% FCS/PBS buffer prior to the addition of fluorescent peptides and the cells were washed with 0.5% sodium azide in PBS buffer. All of the cellular uptake assays were run in parallel in the presence and absence of sodium azide.

Cellular Uptake Kinetics Assay.

The assays were performed as previously described except the cells were incubated for 0.5, 1, 2, and 4 min at 4° C. in triplicate in 2% FCS/PBS (50 µl) in microtiter plates (96 well). The reactions were quenched by diluting the samples into 2% FCS/PBS (5 mL). The assays were then worked up and analyzed by fluorescent flow cytometry as previously described.

Results

To determine the structural requirements for the cellular uptake of short arginine-rich peptides, a series of fluorescently-labeled truncated analogues of $Tat_{49-57}$ were synthesized using standard solid-phase chemistry. See, e.g., Atherton, E. et al. SOLID-PHASE PEPTIDE SYNTHESIS (IRL: Oxford, Engl. 1989). A fluorescein moiety was attached via an aminohexanoic acid spacer on the amino termini. The ability of these fluorescently labeled peptides to enter Jurkat cells was then analyzed using fluorescent activated cell sorting (FACS). The peptide constructs tested were $Tat_{49-57}$ (Fl-ahx-RKKRRQRRR; SEQ ID NO:8): $Tat_{49-56}$ (Fl-ahx-RKKRRQRR; SEQ ID NO:9), $Tat_{49-55}$ (Fl-ahx-RKKRRQR; SEQ ID NO:10), $Tat_{50-57}$ (Fl-ahx-KKRRQRRR; SEQ ID NO:11), and $Tat_{51-57}$ (Fl-ahx-KRRQRRR; SEQ ID NO:12). Differentiation between cell surface binding and internalization was accomplished throughout by running a parallel set of assays in the presence and absence of sodium azide. Because sodium azide inhibits energy-dependent cellular uptake but not cell surface binding, the difference in fluorescence between the two assays provided the amount of fluorescence resulting from internalization.

Deletion of one arginine residue from either the amine terminus ($Tat_{50-57}$) or the carboxyl terminus ($Tat_{49-56}$)

resulted in an 80% loss of intracellular fluorescence compared to the parent sequence (Tat$_{49-57}$). From the one amino acid truncated analogs, further deletion of R-56 from the carboxyl terminus (Tat$_{49-55}$) resulted in an additional 60% loss of intracellular fluorescence, while deletion of K-50 from the amine terminus (Tat$_{51-57}$) did not further diminish the amount of internalization. These results indicate that truncated analogs of Tat$_{49-57}$ are significantly less effective at the transcellular delivery of fluorescein into Jurkat cells, and that the arginine residues appear to contribute more to cellular uptake than the lysine residues.

To determine the contribution of individual amino acid residues to cellular uptake, analogs containing alanine substitutions at each site of Tat$_{49-57}$ were synthesized and assayed by FACS analysis (FIG. 22). The following constructs were tested: A-49 (Fl-ahx-AKKRRQRRR; SEQ ID NO:13), A-50 (Fl-ahx-RAKRRQRRR; SEQ ID NO:14), A-51 (Fl-ahx-RKARRQRRR; SEQ ID NO:15), A-52 (Fl-ahx-RKKARQRRR; SEQ ID NO:16), A-53 (Fl-ahx-RKKRAQRRR; SEQ ID NO:17), A-54 (Fl-ahx-RKKRRARRR; SEQ ID NO:18), A-55 (Fl-ahx-RKKRRQARR; SEQ ID NO:19), A-56 (Fl-ahx-RKKRRQRAR; SEQ ID NO:20), and A-57 (Fl-ahx-RKKRRQRRA; SEQ ID NO:21). Substitution of the non-charged glutamine residue of Tat49_57 with alanine (A-54) resulted in a modest decrease in cellular internalization. On the other hand, alanine substitution of each of the cationic residues individually produced a 70-90% loss of cellular uptake. In these cases, the replacement of lysine (A-50, A-51) or arginine (A-49, A-52, A-55, A-56, A-57) with alanine had similar effects in reducing uptake.

To determine whether the chirality of the transporter peptide was important, the corresponding d-(d-Tat$_{49-57}$), retro-l-(Tat$_{57-49}$), and retro-inverso isomers (d-Tat$_{57-49}$) were synthesized and assayed by FACS analysis (FIG. 23). Importantly, all three analogs were more effective at entering Jurkat cells then Tat$_{49-57}$. These results indicated that the chirality of the peptide backbone is not crucial for cellular uptake. Interestingly, the retro-l isomer (Tat$_{57-49}$) which has three arginine residues located at the amine terminus instead of one arginine and two lysines found in Tat$_{49-57}$ demonstrated enhanced cellular uptake. Thus, residues at the amine terminus appear to be important and that arginines are more effective than lysines for internalization. The improved cellular uptake of the unnatural d-peptides is most likely due to their increased stability to proteolysis in 2% FCS (fetal calf serum) used in the assays. When serum was excluded, the d- and l-peptides were equivalent as expected.

These initial results indicated that arginine content is primarily responsible for the cellular uptake of Tat$_{49-57}$. Furthermore, these results were consistent with our previous results where we demonstrated that short oligomers of arginine were more effective at entering cells then the corresponding short oligomers of lysine, ornithine, and histidine. What had not been established was whether arginine homo-oligomers are more effective than Tat$_{49-57}$. To address this point, Tat$_{49-57}$ was compared to the l-arginine (R5-R9; SEQ ID NOS:1-5) and d-arginine (r5-r9) oligomers. Although Tat$_{49-57}$ contains eight cationic residues, its cellular internalization was between that of R6 (SEQ ID NO:2) and R7 (SEQ ID NO:3) (FIG. 24) demonstrating that the presence of six arginine residues is the most important factor for cellular uptake. Significantly, conjugates containing 7-9 arginine residues exhibited better uptake than Tat$_{49-57}$.

To quantitatively compare the ability of these arginine oligomers and Tat$_{49-57}$ to enter cells, Michaelis-Menton kinetic analyses were performed. The rates of cellular uptake were determined after incubation (3° C.) of the peptides in Jurkat cells for 30, 60, 120, and 240 seconds (Table 1). The resultant K$_m$ values revealed that r9 and R9 (SEQ ID NO:5) entered cells at rates approximately 100-fold and 20-fold faster than Tat$_{47-59}$ respectively. For comparison, Antennaped$_{43-58}$ was also analyzed and was shown to enter cells approximately 2-fold faster than Tat$_{47-59}$, but significantly slower than r9 or R9 (SEQ ID NO:5).

TABLE 1

| Michaelis-Menton kinetics: Antennaped$_{43-58}$ (Fl-ahx-RQIKIWFQNRRMKWKK; SEQ ID NO: 30), | | |
|---|---|---|
| R9 = SEQ ID NO: 5. | | |
| peptide | K$_m$(μM) | V$_{max}$ |
| Tat$_{49-57}$ | 770 | 0.38 |
| Antennapedia$_{43-58}$ | 427 | 0.41 |
| R9 | 44 | 0.37 |
| r9 | 7.6 | 0.38 |

Example 6

Design and Synthesis of Peptidomimetic Analogs of Tat$_{49-57}$

Methods

General Procedure for Peptoid Polyamine Synthesis.

Peptoids were synthesized manually using a fritted glass apparatus and positive nitrogen pressure for mixing the resin following the literature procedure developed by Zuckermann. See, e.g., Murphy, J. E. et al., *Proc. Natl. Acad. Sci. USA* 95, 1517-1522 (1998); Simon, R. J. et al., *Proc. Natl. Acad. Sci. USA* 89, 9367-9371 (1992); Zuckermann, R. N. et al., *J. Am. Chem. Soc.* 114, 10646-10647 (1992). Treatment of Fmoc-substituted Rink amide resin (0.2 mmol) with 20% piperidine/DMF (5 mL) for 30 min (2×) gave the free resin-bound amine which was washed with DMF (3×5 mL). The resin was treated with a solution of bromoacetic acid (2.0 mmol) in DMF (5 mL) for 30 min. This procedure was repeated. The resin was then washed (3×5 mL DMF) and treated with a solution of mono-Boc diamine (8.0 mmol) in DMF (5 mL) for 12 hrs. These two steps were repeated until an oligomer of the required length was obtained (Note: the solution of mono-Boc diamine in DMF could be recycled without appreciable loss of yield). The resin was then treated with N-Fmoc-aminohexanoic acid (2.0 mmol) and DIC (2.0 mmol) in DMF for 1 h and this was repeated. The Fmoc was then removed by treatment with 20% piperidine/DMF (5 mL) for 30 min. This step was repeated and the resin was washed with DMF (3×5 mL). The free amine resin was then treated with fluorescein isothiocyanate (0.2 mmol) and DIEA (2.0 mmol) in DMF (5 mL) for 12 hrs. The resin was then washed with DMF (3×5 mL) and dichloromethane (5×5 mL). Cleavage from the resin was achieved using 95:5 TFA/triisopropylsilane (8 mL). Removal of the solvent in vacuo gave a crude oil which was triturated with cold ether (20 mL). The crude mixture thus obtained was centrifuged, the ether was removed by decantation, and the resulting orange solid was purified by reverse-phase HPLC (H$_2$O/CH$_3$CN in 0.1% TFA). The products were isolated by lyophilization and characterized by electrospray mass spectrometry and in selected cases by $^1$H NMR spectroscopy.

General Procedure for Perguanidinylation of Peptoid Polyamines.

A solution of peptoid amine (0.1 mmol) dissolved in deionized water (5 mL) was treated with sodium carbonate (5 equivalents per amine residue) and pyrazole-1-carboxamidine (5 equivalents per amine residue) and heated to 50° C. for 24-48 hr. The crude mixture was then acidified with TFA (0.5 mL) and directly purified by reverse-phase HPLC (H$_2$O/CH$_3$CN in 0.1% TFA). The products were characterized by electrospray mass spectrometry and isolated by lyophilization and further purified by reverse-phase HPLC. The purity of the guanidine-substituted peptoids was >95% as determined by analytical reverse-phase HPLC($H_2O$/$CH_3CN$ in 0.1% TFA).

Results

Utilizing the structure-function relationships that had been determined for the cellular uptake of $Tat_{47-59}$, we designed a set of polyguanidine peptoid derivatives that preserve the 1,4 backbone spacing of side chains of arginine oligomers, but have an oligo-glycine backbone devoid of stereogenic centers. These peptides incorporating arginine-like side chains on the amide nitrogen were selected because of their expected resistance to proteolysis, and potential ease and significantly lower cost of synthesis (Simon et al., *Proc. Natl. Acad. Sci. USA* 89:9367-9371 (1992); Zuckermann, et al., *J. Am. Chem. Soc.* 114:10646-10647 (1992). Furthermore, racemization, frequently encountered in peptide synthesis, is not a problem in peptoid synthesis; and the "sub-monomer" peptoid approach allows for facile modification of side-chain spacers. Although the preparation of an oligurea and peptoid-peptide hybrid (Hamy, et al, *Proc. Natl. Acad. Sci. USA* 94:3548-3553 (1997)) derivatives of $Tat_{49-57}$ have been previously reported, their cellular uptake was not explicitly studied.

The desired peptoids were prepared using the "sub-monomer" approach (Simon et al.; Zuckermann et al.) to peptoids followed by attachment of a fluorescein moiety via an aminohexanoic acid spacer onto the amine termini. After cleavage from the solid-phase resin, the fluorescently labeled polyamine peptoids thus obtained were converted in good yields (60-70%) into polyguanidine peptoids by treatment with excess pyrazole-1-carboxamidine (Bernatowicz, et al., *J. Org. Chem.* 57:2497-2502 (1992) and sodium carbonate (as shown in FIG. 25). Previously reported syntheses of peptoids containing isolated N-Arg units have relied on the synthesis of N-Arg monomers (5-7 steps) prior to peptoid synthesis and the use of specialized and expensive guanidine protecting groups (Pmc, Pbf) (Kruijtzer, et al., *Chem. Eur. J.* 4:1570-1580 (1998); Heizmann, et al. *Peptide Res.* 7:328-332 (1994). The compounds reported here represent the first examples of polyguanidinylated peptoids prepared using a perguanidinylation step. This method provides easy access to polyguanidinylated compounds from the corresponding polyamines and is especially useful for the synthesis of perguanidinylated homooligomers. Furthermore, it eliminates the use of expensive protecting groups (Pbf, Pmc). An additional example of a perguanidinylation of a peptide substrate using a novel triflyl-substituted guanylating agent has recently been reported (Feichtinger, et al., *J. Org. Chem.* 63:8432-8439 (1998)).

The cellular uptake of fluorescently labeled polyguanidine N-arg5,7,9 (SEQ ID NOS:76, 78 and 80) peptoids was compared to the corresponding d-arginine peptides r5,7,9 (similar proteolytic properties) using Jurkat cells and FACS analysis. The amount of fluorescence measured inside the cells with N-arg5,7,9 (SEQ ID NOS:76, 78 and 80) was proportional to the number of guanidine residues: N-arg9>N-arg7>N-arg5 (SEQ ID NOS:76, 78 and 80) (FIG. 26), analogous to that found for r5,7,9. Furthermore, the N-arg5,7,9 (SEQ ID NOS: 76, 78 and 80) peptoids showed only a slightly lower amount of cellular entry compared to the corresponding peptides, r5,7,9. The results demonstrate that the hydrogen bonding along the peptide backbone of $Tat_{49-57}$ or arginine oligomers is not a required structural element for cellular uptake and oligomeric guanidine-substituted peptoids can be utilized in place of arginine-rich peptides as molecular transporters. The addition of sodium azide inhibited internalization demonstrating that the cellular uptake of peptoids was also energy dependent.

Example 7

The Effect of Side Chain Length on Cellular Uptake

After establishing that the N-arg peptoids efficiently crossed cellular membranes, the effect of side chain length (number of methylenes) on cellular uptake was investigated. For a given number of guanidine residues (5,7,9), cellular uptake was proportional to side chain length. Peptoids with longer side chains exhibited more efficient cellular uptake. A nine-mer peptoid analog with a six-methylene spacer between the guanidine head groups and the backbone (N-hxg9) exhibited remarkably higher cellular uptake than the corresponding d-arginine oligomer (r9). The relative order of uptake was N-hxg9 (6 methylene)>N-btg9 (4 methylene)>r9 (3 methylene)>N-arg9 (SEQ ID NO:80) (3 methylene)>N-etg9 (2 methylene) (FIG. 27). Of note, the N-hxg peptoids showed remarkably high cellular uptake, even greater than the corresponding d-arginine oligomers. The cellular uptake of the corresponding heptamers and pentamers also showed the same relative trend. The longer side chains embodied in the N-hxg peptoids improved the cellular uptake to such an extent that the amount of internalization was comparable to the corresponding d-arginine oligomer containing one more guanidine residue (FIG. 28). For example, the N-hxg7 peptoid showed comparable cellular uptake to r8.

To address whether the increase in cellular uptake was due to the increased length of the side chains or due to their hydrophobic nature, a set of peptoids was synthesized containing cyclohexyl side chains. These are referred to as the N-chg-5,7,9 peptoids. These contain the same number of side chain carbons as the N-hxg peptoids but possess different degrees of freedom. Interestingly, the N-chg peptoid showed much lower cellular uptake activity than all of the previously assayed peptoids, including the N-etg peptoids (FIG. 29). Therefore, the conformational flexibility and sterically unencumbered nature of the straight chain alkyl spacing groups is important for efficient cellular uptake.

Discussion

The nona-peptide, $Tat_{49-57}$, has been previously shown to efficiently translocate through plasma membranes. The goal of this research was to determine the structural basis for this effect and use this information to develop simpler and more effective molecular transporters. Toward this end, truncated and alanine substituted derivatives of $Tat_{49-57}$ conjugated to a fluoroscein label was prepared. These derivatives exhibited greatly diminished cellular uptake compared to $Tat_{49-57}$, indicating that all of the cationic residues of $Tat_{49-57}$ are required for efficient cellular uptake. When compared with our previous studies on short oligomers of cationic oligomers, these findings suggested that an oligomer of arginine might be superior to $Tat_{49-57}$ and certainly more easily and cost effectively prepared. Comparison of short arginine oligomers with $Tat_{49-57}$ showed that members of the former were indeed more efficiently taken into cells. This was further quantified for the first time by Michaelis-Menton kinetics analysis which showed that the R9 SEQ ID NO:5) and r9 oligomers had Km values 30-fold and 100-fold greater than that found for $Tat_{49-57}$.

Given the importance of the guanidino head group and the apparent insensitivity of the oligomer chirality revealed in our peptide studies, we designed and synthesized a novel series of polyguanidine peptoids. The peptoids N-arg5,7,9 (SEQ ID NOS: 76, 78 and 80), incorporating the arginine side chain, exhibited comparable cellular uptake to the corresponding d-arginine peptides r5,7,9, indicating that the hydrogen bonding along the peptide backbone and backbone chirality are not essential for cellular uptake. This observation is consistent with molecular models of these peptoids, arginine oligomers, and $Tat_{49-57}$, all of which have a deeply embedded backbone and a guanidinium dominated surface. Molecular models further reveal that these structural characteristics are retained in varying degree in oligomers with different alkyl spacers between the peptoid backbone and guanidino head groups. Accordingly, a series of peptoids incorporating 2-(N-etg), 4-(N-btg), and 6-atom (N-hxg) spacers between the backbone and side chain were prepared and compared for cellular uptake with the N-arg peptoids (3-atom spacers) and d-arginine oligomers. The length of the side chains had a dramatic effect on cellular entry. The amount of cellular uptake was proportional to the length of the side chain with N-hxg>N-btg>N-arg>N-etg. Cellular uptake was improved when the number of alkyl spacer units between the guanidine head group and the backbone was increased. Significantly, N-hxg9 was superior to r9, the latter being 100-fold better than Tat$_{49-57}$. This result led us to prepare peptoid derivatives containing longer octyl spacers (N-ocg) between the guanidino groups and the backbone. Issues related to solubility prevented us from testing these compounds.

Because both perguanidinylated peptides and perguanidinylated peptoids efficiently enter cells, the guanidine head group (independent of backbone) is apparently the critical structural determinant of cellular uptake. However, the presence of several (over six) guanidine moieties on a molecular scaffold is not sufficient for active transport into cells as the N-chg peptoids did not efficiently translocate into cells. Thus, in addition to the importance of the guanidine head group, there are structure/conformational requirements that are significant for cellular uptake.

In summary, this investigation identified a series of structural characteristics including sequence length, amino acid composition, and chirality that influence the ability of Tat$_{49-57}$ to enter cells. These characteristics provided the blueprint for the design of a series of novel peptoids, of which 17 members were synthesized and assayed for cellular uptake. Significantly, the N-hxg9 transporter was found to be superior in cell uptake to r9 which was comparable to N-btg9. Hence, these peptoid transporters proved to be substantially better than Tat$_{49-57}$. This research established that the peptide backbone and hydrogen bonding along that backbone are not required for cellular uptake, that the guanidino head group is superior to other cationic subunits, and most significantly, that an extension of the alkyl chain between the backbone and the head group provides superior transporters. In addition to better uptake performance, these novel peptoids offer several advantages over Tat$_{49-57}$ including cost-effectiveness, ease of synthesis of analogs, and protease stability. These features along with their significant water solubility (>100 mg/mL) indicate that these novel peptoids could serve as effective transporters for the molecular delivery of drugs, drug candidates, and other agents into cells.

Example 8

Synthesis of Itraconazole-Transporter Conjugate

This Example provides one application of a general strategy for attaching a delivery-enhancing transporter to a compound that includes a triazole structure. The scheme, using attachment of itraconazole to an arginine (r7) delivery-enhancing transporter as an example, is shown in FIG. 30. In the scheme, R is H or alkyl, n is 1 or 2, and X is a halogen.

The reaction involves making use of quaternization of a nitrogen in the triazole ring to attach an acyl group that has a halogen (e.g., Br, Fl, I) or a methyl ester. Compound 3 was isolated by HPLC. Proton NMR in D$_2$O revealed itraconazole and transporter peaks.

The methyl ester provided yields of 70% and greater, while yields obtained using the Br-propionic acid/ester pair were 40-50%. The acyl derivative is then reacted with the amine of the delivery-enhancing transporter to form the conjugate. Alternatively, the halogenated acyl group can first be attached to the transporter molecule through an amide linkage, after which the reaction with the drug compound is conducted.

Example 9

Preparation of FK506 Conjugates

This Example describes the preparation of conjugates in which FK506 is attached to a delivery-enhancing transporter. Two different linkers were used, each of which released FK506 at physiological pH (pH 5.5 to 7.5), but had longer half-lives at more acidic pH. These schemes are diagrammed in FIGS. 31A and B.

Linker 1: 6-Maleimidocaproic Hydrazide Trifluoroacetate (Scheme I and II)

A solution of FK506 (1) (0.1 g, 124.4 µmol), 6-maleimidocaproic hydrazide trifluoroacetate (2) (0.126 g, 373.2 µmol) and trifluoroacetic acid (catalytic, 1 µL) in anhydrous methanol (5 mL) was stirred at room temperature for 36 h. The reaction was monitored by thin layer chromatography that showed almost complete disappearance of the starting material. [TLC solvent system—dichloromethane (95): methanol (5), R$_f$=0.3]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (96): methanol (4) as eluent to give the hydrazone 3 (0.116 g, 92%).

A solution of the above hydrazone (3) (0.025 g, 24.7 µmol), transporter (1×, Bacar$_9$CCONH$_2$.9TFA, Bacar$_7$CCONH$_2$.7TFA, BacaCCONH$_2$, NH$_2$r$_7$CCONH$_2$.8TFA, NH$_2$R$_7$CCONH$_2$.8TFA (SEQ ID NO:32)) and diisopropylethylamine (1×) in anhydrous dimethylformamide (1 mL) were stirred under nitrogen at room temperature for 36 h when TLC indicated the complete disappearance of the starting hydrazone. Solvent was evaporated from the reaction mixture and the residue purified by reverse phase HPLC using trifluoroacetic acid buffered water and acetonitrile.

Yields of conjugates with various transporters:
Conjugate with Bacar$_9$CCONH$_2$.9TFA (4)—73%
Bacar$_7$CCONH$_2$.7TFA (5)—50%
BacaCCONH$_2$ (6)—52.9% NH$_2$r1CCONH$_2$.8TFA (7)—43.8%
NH$_2$R$_7$CCONH$_2$.8TFA (SEQ ID NO:32) (8)—62.8%
Structures of all the products were confirmed by $^1$H-NMR spectra and TOF MS analysis.

Linker 2: 2-(2-pyridinyldithio) ethyl hydrazine carboxylate (Scheme III and IV)

A solution of FK506 (1) (0.1 g, 124.4 µl), 2-(2-pyridinyldithio) ethyl hydrazine carboxylate (9) (0.091 g, 373.2 µmol) and trifluoroacetic acid (catalytic, 1 µL) in anhydrous methanol (5 mL) was stirred at room temperature for 16 h. The reaction was monitored by thin layer chromatography that showed almost complete disappearance of the starting material. [TLC solvent system–ethyl acetate R$_f$=0.5]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (97): methanol (3) as eluent to give the hydrazone 10 (0.091 g, 71%)

Example 10

This example illustrates the conjugation of cyclosporin to a transport moiety using a pH sensitive linking group (see FIGS. 6A and 9B).

In this example, cyclosporin is converted to its α-chloroacetate ester using chloroacetic anhydride to provide 6i (see FIG. 6). The ester 6i is then treated with benzylamine to provide 6ii. Reaction of the amine with Boc-protected iminodiacetic acid anhydride provides the acid 6iii which is then converted to an activated ester (6iv) with N-hydroxy succinimide. Coupling of 6iv with L-Arginine heptamer (SEQ ID NO:3) provides the BOC-protected conjugate 6v, which can be converted to conjugate 6vi by removal of the BOC protecting group according to established methods.

Transport moieties having arginine groups separated by, for example, glycine, ε-aminocaproic acid, or γ-aminobutyric acid can be used in place of the arginine heptamer (SEQ ID NO:3) in this and in the following examples that show oligoarginine transport groups.

Example 11

This example illustrates the conjugation of acyclovir to a transport moiety.

a. Conjugation of Acyclovir to r₇CONH₂

This example illustrates the conjugation of acyclovir to r₇CONH₂ via the linking group:

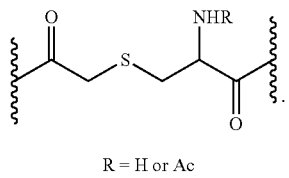

R = H or Ac

A solution of acyclovir (100 mg, 0.44 mmol), dimethylaminopyridine (5.4 mg, 0.044 mmol) and chloroacetic anhydride (226 mg, 1.32 mmol) in dimethylformamide (9 mL) was stirred at room temperature for 18 h. The dimethylformamide was removed by evaporation. The crude product was purified by reverse-phase HPLC (22 mm×250 mm C-18 column, a 5-25% $CH_3CN/H_2O$ gradient with 0.1% trifluoroacetic acid, 214 and 254 nm UV detection) and lyophilized. The product was obtained as a white powder (62 mg, 47%). $^1$H NMR (300 MHz, DMSO-$d_6$) δ 10.67 (s, 1H), 7.88 (s, 1H), 6.53 (s, 1H), 5.27 (s, 2H), 4.35 (s, 2H), 4.21 (t, J=3 Hz, 2H), 3.70 (t, J=3 Hz, 2H); $^{13}$C NMR (75 MHz, DMSO-$d_6$) δ 168.1, 157.6, 154.8, 152.3, 138.6, 117.1, 72.7, 67.1, 65.2, 41.8; TOF-MS (m/z): 302.0 [M+H].

ii) Conjugation of Acyclovir α-Chloro Ester to H₂N—C-r7-CONH₂

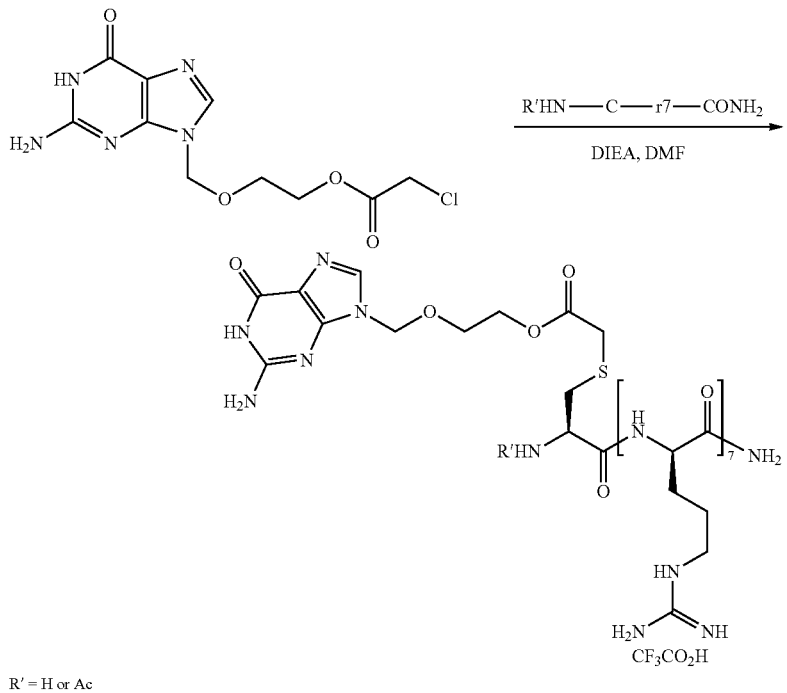

R' = H or Ac i) Preparation of Acyclovir α-Chloroester:

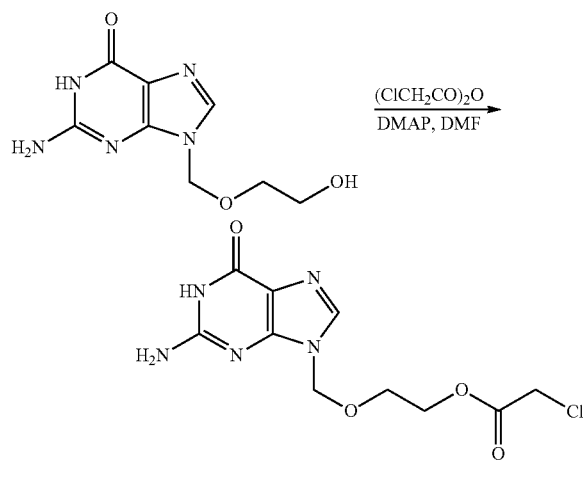

A solution of acyclovir α-chloroester (7 mg, 0.024 mmol), H₂N—C-r7-CONH₂ (50 mg, 0.024 mmol) and diisopropylethylamine (6.4 µL, 0.036 mmol) in dimethylformamide (1 mL) was stirred for 18 h. The dimethylformamide was removed by evaporation. The crude product was purified by reverse-phase HPLC (22 mm×250 mm C-18 column, a 5-25% $CH_3CN/H_2O$ gradient with 0.1% trifluoroacetic acid, 214 and 254 nm UV detection) and lyophilized. The desired product was obtained as a white powder (24 mg, 69%). TOF-MS (m/z): 494.6 [(M+H)/3], 371.0 [(M+H)/4].

The yield could be increased by using 10 molar equivalents of diisopropylethylamine rather than 1.5 molar equivalents. Product was again obtained as a white powder (79%). TOF-MS (m/z): 508.7 [(M+H)/3], 381.5 [(M+H)/4], 305.5 [(M+H)/5].

b. Conjugation of Acyclovir to a Biotin-Containing Derivative of $r_5$-Cys-CONH$_2$

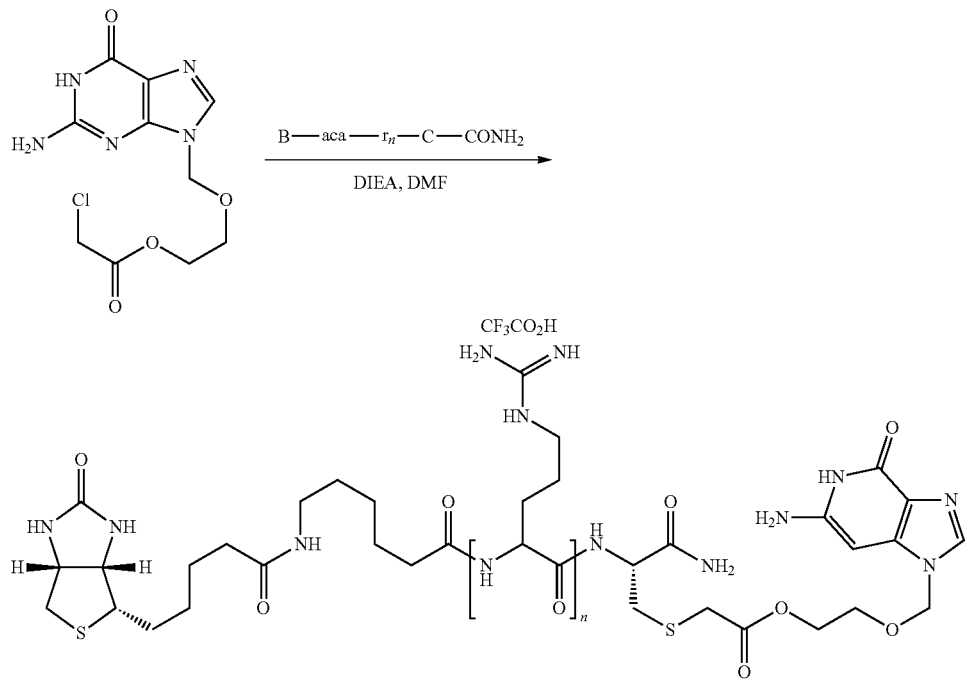

Reactions were carried out as illustrated above, using the synthetic techniques provided in the examples above.

i) Biotin-aminocaproic acid-r5-Cys(acyclovir)-CONH$_2$ was obtained as a white powder (36%). TOF-MS (m/z): 868.2 {(M+2 TFA)/2], 811.2 [(M+1 TFA)/2], 754.1 [(M+1 TFA)/3], 503.0 [(M+H)/3], 377.4 [(M+H)/4].

Similarly, ii) Biotin-aminocaproic acid-r7-C(acyclovir)-CONH$_2$— was obtained as a white powder (33%). TOF-MS (m/z):722.1 [(M+3 TFA)/3], 684.6 [(M+2 TFA)/3], 607.1 [(M+H)/3], 455.5 [(M+H)/4], 364.8 [(M+H)/5], 304.3 [(M+H)/6].

Example 12

This example illustrates the conjugation of hydrocortisone to a transport moiety.

a. Conjugation of Hydrocortisone to $r_7$CONH$_2$ i) Preparation of Hydrocortisone α-Chloroester:

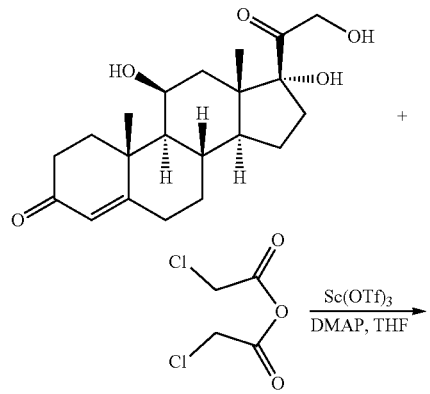

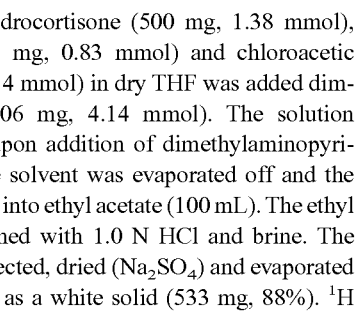

To a solution of hydrocortisone (500 mg, 1.38 mmol), scandium triflate (408 mg, 0.83 mmol) and chloroacetic anhydride (708 mg, 4.14 mmol) in dry THF was added dimethylaminopyridine (506 mg, 4.14 mmol). The solution turned bright yellow upon addition of dimethylaminopyridine. After 30 min the solvent was evaporated off and the crude material taken up into ethyl acetate (100 mL). The ethyl acetate layer was washed with 1.0 N HCl and brine. The organic phase was collected, dried (Na$_2$SO$_4$) and evaporated to provide the product as a white solid (533 mg, 88%). $^1$H NMR (300 MHz, DMSO-d$_6$) δ 5.56 (s, 1H), 5.46 (s, 1H), 5.20 (d, J=18 Hz, 1H), 4.85 (d, J=18 Hz, 1H), 4.51 (s, 2H), 4.37 (br s, 1H), 4.27 (br s, 1H), 2.54-2.33 (m, 2H), 2.22-2.03 (m, 3H), 1.99-1.61 (m, 8H), 1.52-1.24 (m, 5H), 1.02-0.98 (d, J=12 Hz, 1H), 0.88-0.85 (d, J=9 Hz, 1H), 0.77 (s, 3H); $^{13}$C NMR (75 MHz, DMSO-d$_6$) δ 205.4, 198.8, 173.0, 167.6, 122.3, 89.5, 69.7, 67.3, 56.4, 52.4, 47.8, 41.6, 39.7, 35.0, 34.3, 34.0, 33.6, 32.3, 32.0, 24.2, 21.3, 17.4; TOF-MS (m/z): 439.1 (M+H).

(Reference for acetylation—Zhao, H.; Pendri, A.; Greenwald, R. B. *J. Org. Chem.* 1998, 63, 7559-7562.)

ii) Coupling to R'NH-Cys-$r_7$-CONH$_2$

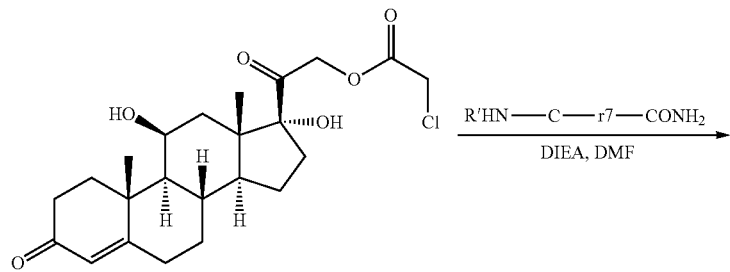

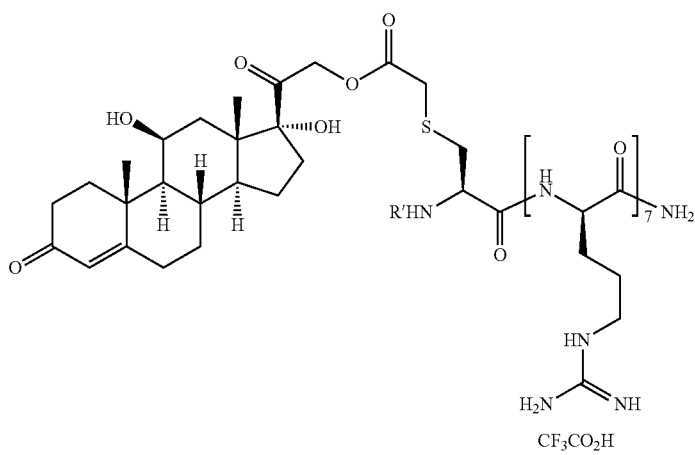

R' = H or Ac

A solution of hydrocortisone α-chloroester (31 mg, 0.071 mmol), H$_2$N—C-r7-CONH$_2$ (150 mg, 0.071 mmol) and diisopropylethylamine (15 μL, 0.085 mmol) in dimethylformamide (1 mL) was stirred for 18 h. The dimethylformamide was evaporated off. The crude product purified by reverse-phase HPLC (22 mm×250 mm C-18 column, a 5-30% CH$_3$CN/H$_2$O gradient with 0.1% trifluoroacetic acid, 214 and 254 nm UV detection) and lyophilized. The desired product was obtained as a white powder (25 mg, 14%). TOF-MS (m/z): 1037.4 [(M+4 TFA)/2], 616.1 [(M+2 TFA)/3], 578.3 [(M+1 TFA)/3], 540.5 [(M+H)/3], 405.7 [(M+H)/4], 324.5 [(M+H)/5].

The use of 10 molar equivalents of diisopropylethylamine rather than 1.2 molar equivalents provided the desired product as a yellow powder (52% yield). TOF-MS (m/z): 887.0 [(M+1TFA)/2], 830.6 [(M+H)/2], 553.7 [(M+H)/3], 415.5 [(M+H)/4].

b. Conjugation of Hydrocortisone to a Biotin-Containing Derivative of $r_5$-Cys-CONH$_2$

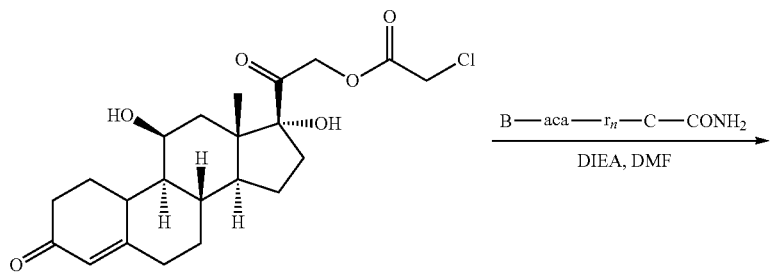

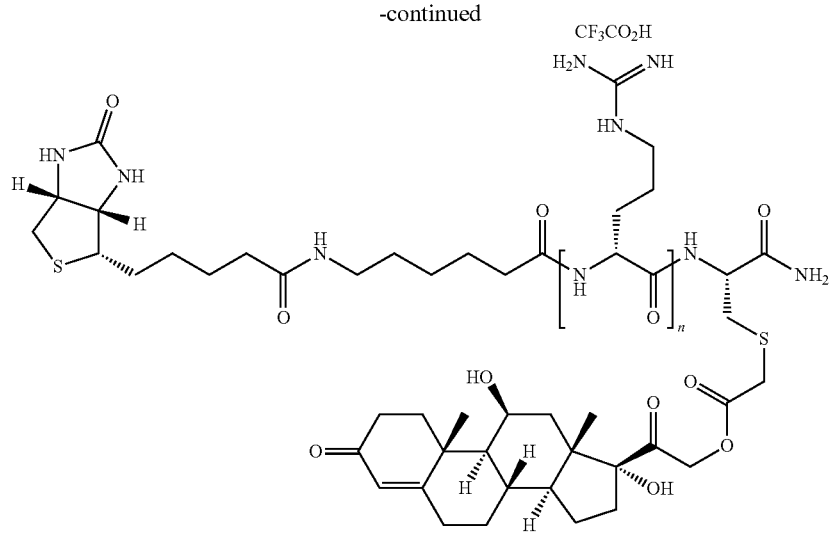

n = 5 or 7

Reactions were carried out as illustrated above, using the synthetic techniques provided in the examples above.

i) Biotin-Aminocaproic Acid-r5-C(hydrocortisone)-CONH$_2$— Used 10 molar equivalents of diisopropylethylamine rather than 1.2 molar equivalents. Product a white powder (65%). TOF-MS (m/z): 880.7 [(M+1 TFA)/2], 548.7 [(M+H)/3].

ii) Biotin-Aminocaproic Acid-r7-C(hydrocortisone)-CONH$_2$— Used 10 molar equivalents of diisopropylethylamine rather than 1.2 molar equivalents. Product a white powder (36%). TOF-MS (m/z): 692.3 [(M+1 TFA)/3], 652.8 [(M+H)/3], 520.0 [(M+1 TFA)/4], 490.0 [(M+H)/4], 392.5 [(M+H)/5].

Example 13

This example illustrates the conjugation of taxol to a transport moiety.

a. Conjugation of Taxol to r$_7$-CONH$_2$

Figure 12:
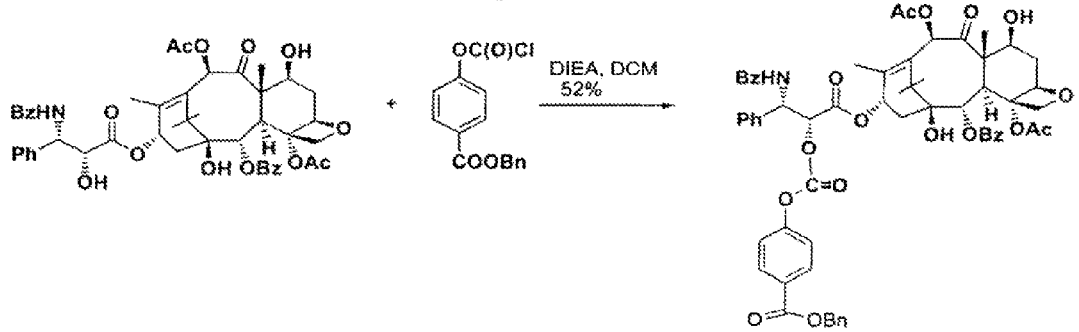
FIG. 12 shows a reaction for preparation of C-2' derivatives of taxol.

This example illustrates the application of methodology outlined above to the preparation of a taxol conjugate (see FIG. 12).

i) Preparation of a Taxol α-Chloroacetate Ester

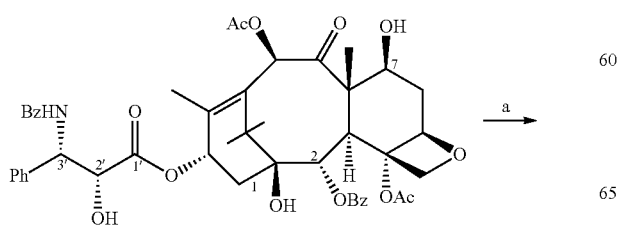

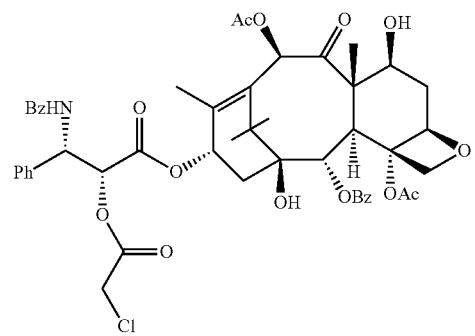

a) Cl—Ac$_2$O, DIEA, CH$_2$Cl$_2$, rt, 3h

Taxol was treated with α-chloro acetic anhydride providing the C-2' chloro acetyl derivative 12i in essentially quantitative yield.

ii) Formation of Taxol Conjugate

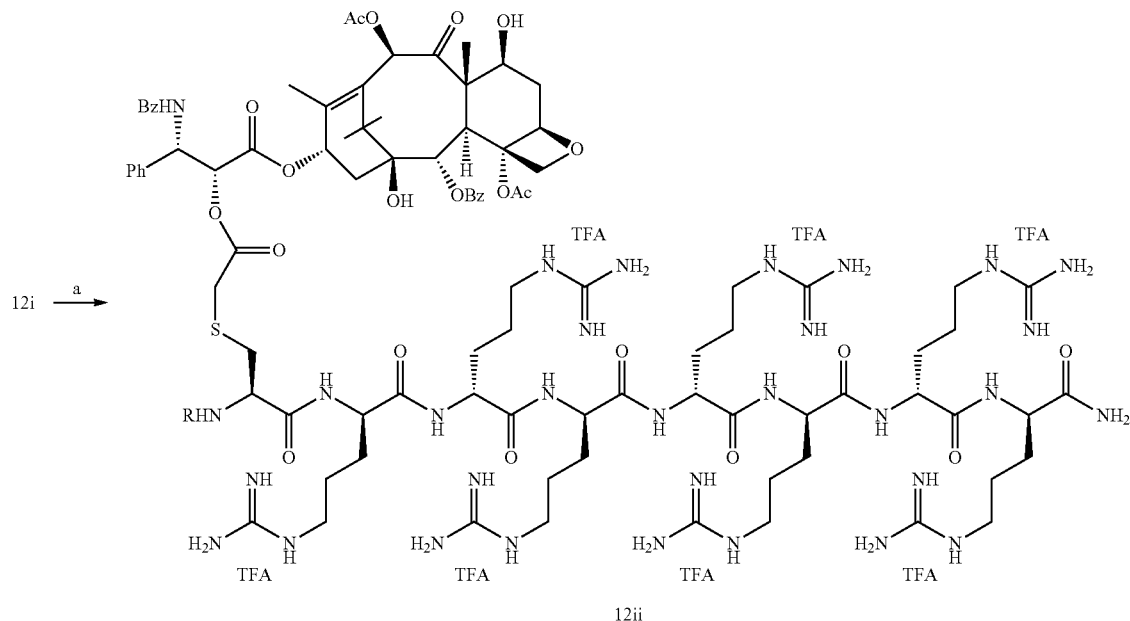

a) peptide, DIEA, DMF, rt
R = H 48%
R = Ac 87%

The halogen atom of the chloroacetate ester was displaced by the thiol of an N-terminal (L) cysteine containing heptamer of arginine. To avoid degradation of the transporter entity by proteases in-vivo, D-arginine was used as the building unit. Conjugation reactions were performed at room temperature in DMF in the presence of diisopropylethylamine. The final products were isolated by RP-HPLC and lyophilized to white powders. It is important to note that the native conjugate (R=H) is isolated as its TFA salt at the cysteine primary amine. The conjugates are generally quite hygroscopic and readily dissolve in water.

The conjugate wherein R=H was designed to release the parent drug via a nucleophilic attack of the N-terminal nitrogen onto the C2' ester carbonyl. The protonation state of this nitrogen is crucial for this mechanism, since only the free amine will be capable of this release. Additionally, both conjugates share a common α-hetero atom substituted acetate moiety making them susceptible to simple ester hydrolysis. This offers an additional release pathway.

Example 14

This example illustrates two methods of linking active agents to transport moieties. Illustration is provided for retinoic acid derivatives linked to poly-D-Arg derivatives but can be applied to linkages between other biological agents and the transport moieties of the present invention.

A. Linkage Between a Biological Agent Having an Aldehyde Functional Group

This example illustrates the preparation of a conjugate between a nonamer of D-arginine ($H_2N$-$r_9$-$CO_2H$.10TFA) and either all trans-retinal or 13-cis-retinal. FIG. 33 provides a schematic presentation of the reactions. As seen in FIG. 33, condensation of either retinal with $H_2N$-$r_9$-$CO_2H$.10TFA in MeOH in the presence of 4 Å molecular sieves at room temperature for four hours results in the formation of a Schiff base-type linkage between the retinal aldehyde and the amino terminal group. Purification of the conjugate can be accomplished by filtering the molecular sieves and removing methanol under reduced pressure.

b. Conjugation of Retinoic Acid to $r_7$-$CONH_2$

This example illustrates the preparation of a conjugate between retinoic acid and $r_7$-$CONH_2$ using the linking group

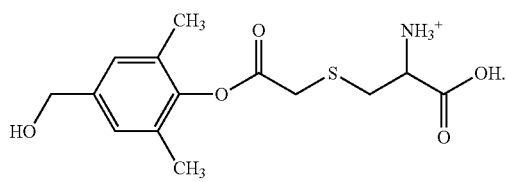 [SMILES: Cc1cc(CO)cc(C)c1OC(=O)CSCC([NH3+])C(=O)O]

Here, preparation of the conjugate follows the scheme outlined in FIG. 34. In this scheme, retinoic acid (34ii) is first combined with the chloroacetate ester of 4-hydroxymethyl-2,6-dimethylphenol (34i) to provide the conjugate shown as 34iii. Combination of 34i with retinoic acid in methylene chloride in the presence of dicyclohexylcarbodiimide and a catalytic amount of 4-dimethylaminopyridine provided the retinoid derivative 34iii in 52-57% yield. Condensation of 34iii with $H_2NCys$-$r_7CONH_2$.8TFA in the presence of diisopropylethylamine (DMF, room temperature, 2 h) provides the desired conjugated product 34iv.

Example 15

Synthesis of Cyclosporin Conjugated to a Biotinylated Pentamer, Heptamer, and Nonamer of D-Arginine Methods A. Linking Cyclosporin to Delivery-Enhancing Transporters 1. Preparation of the α-Chloroacetyl Cyclosporin A Derivative.

Figure 1:
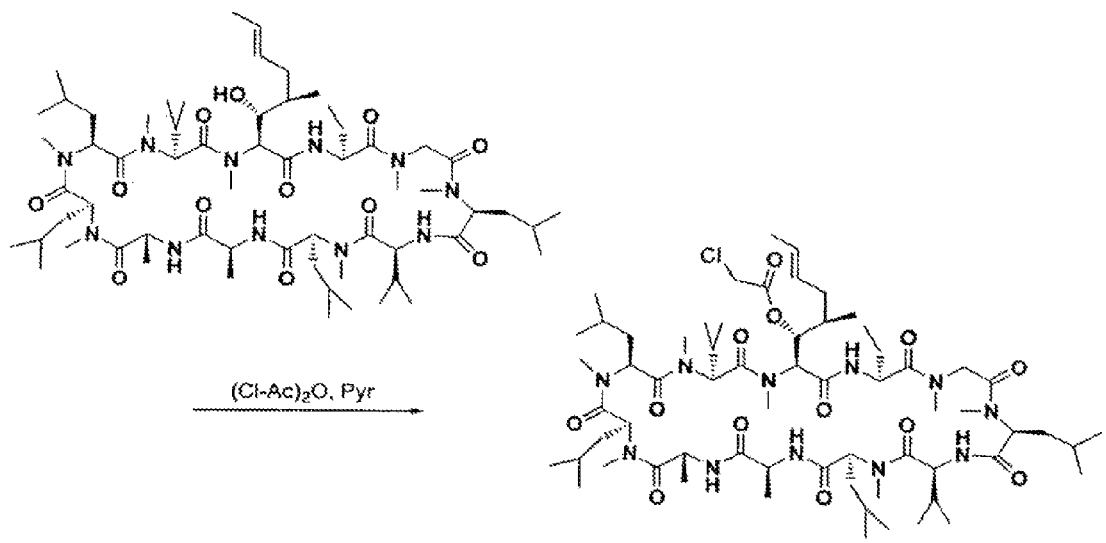

The α-chloroacetyl cyclosporin A derivative was prepared as shown in FIG. 1. Cyclosporin A (152.7 mg, 127 μmol) and chloroacetic acid anhydride (221.7 mg; 1300 µmol) were placed into a dry flask under $N_2$-atmosphere. Pyridine (1.0 mL) was added and the solution was heated to 50° C. (oil bath). After 16 hours the reaction was cooled to room temperature and quenched with water (4.0 mL). The resulting suspension was extracted with diethylether (Σ15 mL). The combined organic layers were dried over $MgSO_4$. Filtration and evaporation of solvents in vacuo delivered a yellow oil, which was purified by flash chromatography on silica gel (eluent: EtOAc/hexanes: 40%-80%) yielding 136 mg (106.4 mmol, 83%) of the desired product.

2. Coupling to Transporter Molecules

Figure 2:
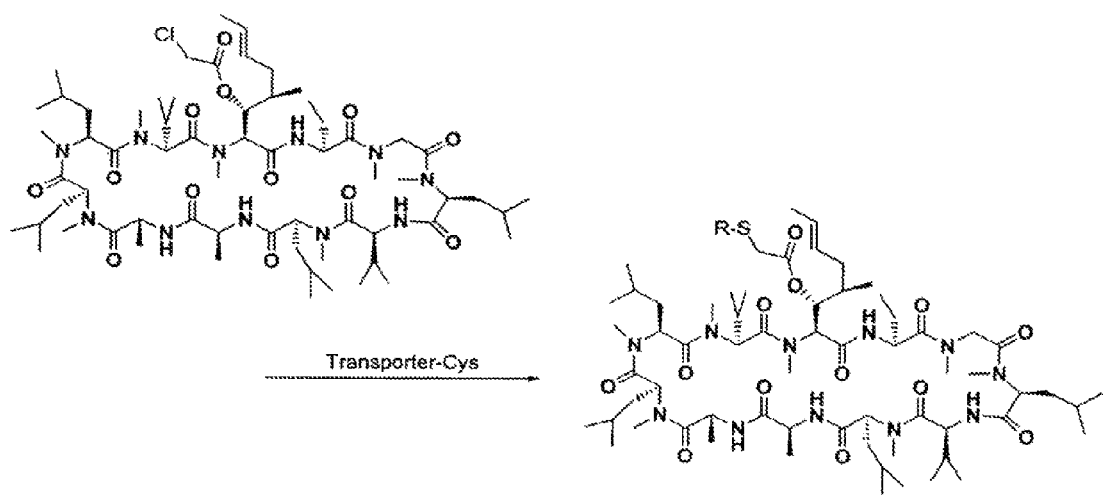

A general procedure for the coupling of cysteine containing peptides to the α-chloro acetyl Cyclosporin A derivative is shown in FIG. 2.

a. Labeled Peptides

Figure 3:
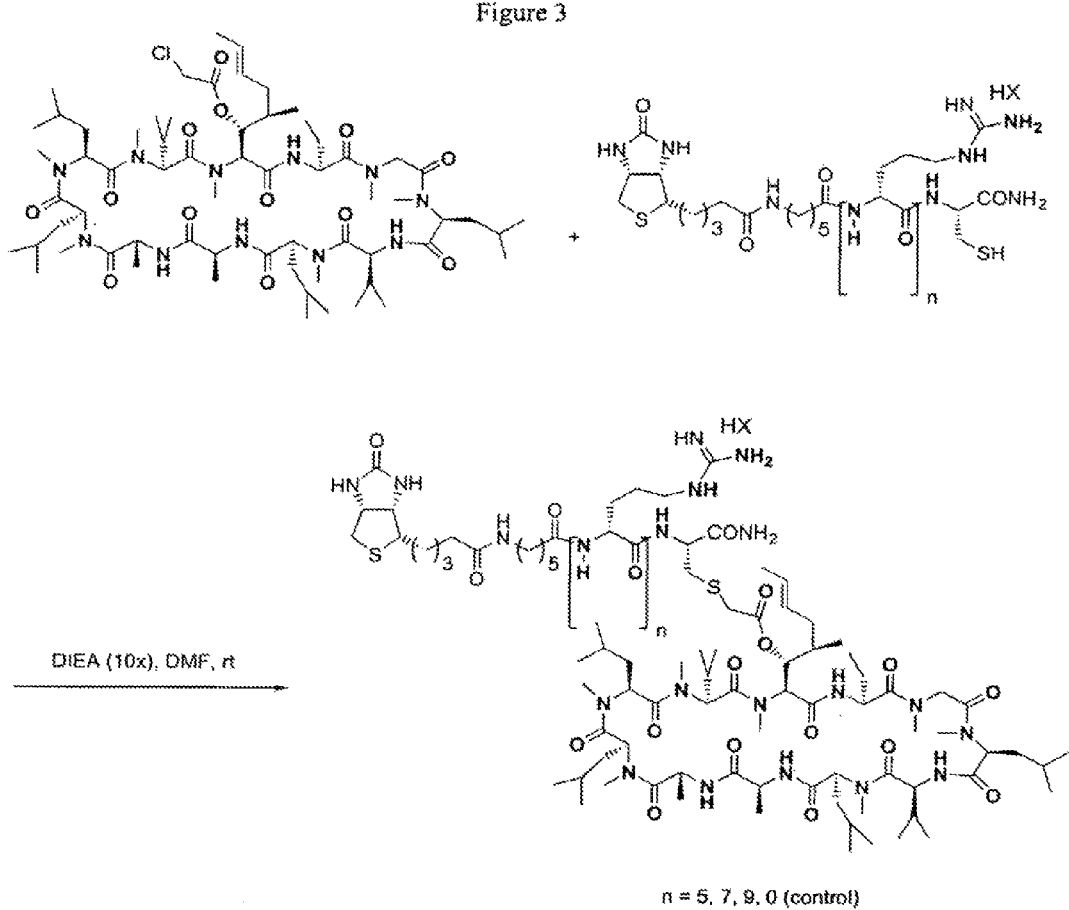

The cyclosporin A derivative and the labeled peptide (1 equivalent) were dissolved in DMF (~10 mmol of Cyclosporin A derivative/mL DMF) under an $N_2$-atmosphere. Diisopropylethylamine (10 equivalents) was added and stirring at room temperature was continued until all starting material was consumed (usually after 16 hours) (FIG. 3). The solvents were removed in vacuo and the crude reaction product was dissolved in water and purified by reversed phase high pressure liquid chromatography (RP-HPLC) (eluent: water/MeCN*TFA). The products were obtained in the following yields:

B-aca-r5-Ala-Ala-Cys-O-acyl-Cyclosporin A: 47%
B-aca-r7-Cys-O-acyl-Cyclosporin A: 43%
B-aca-r9-Cys-O-acyl-Cyclosporin A: 34%
B-aca-Cys-O-acyl-Cyclosporin A: 55% b. Unlabeled Peptides

Figure 4:
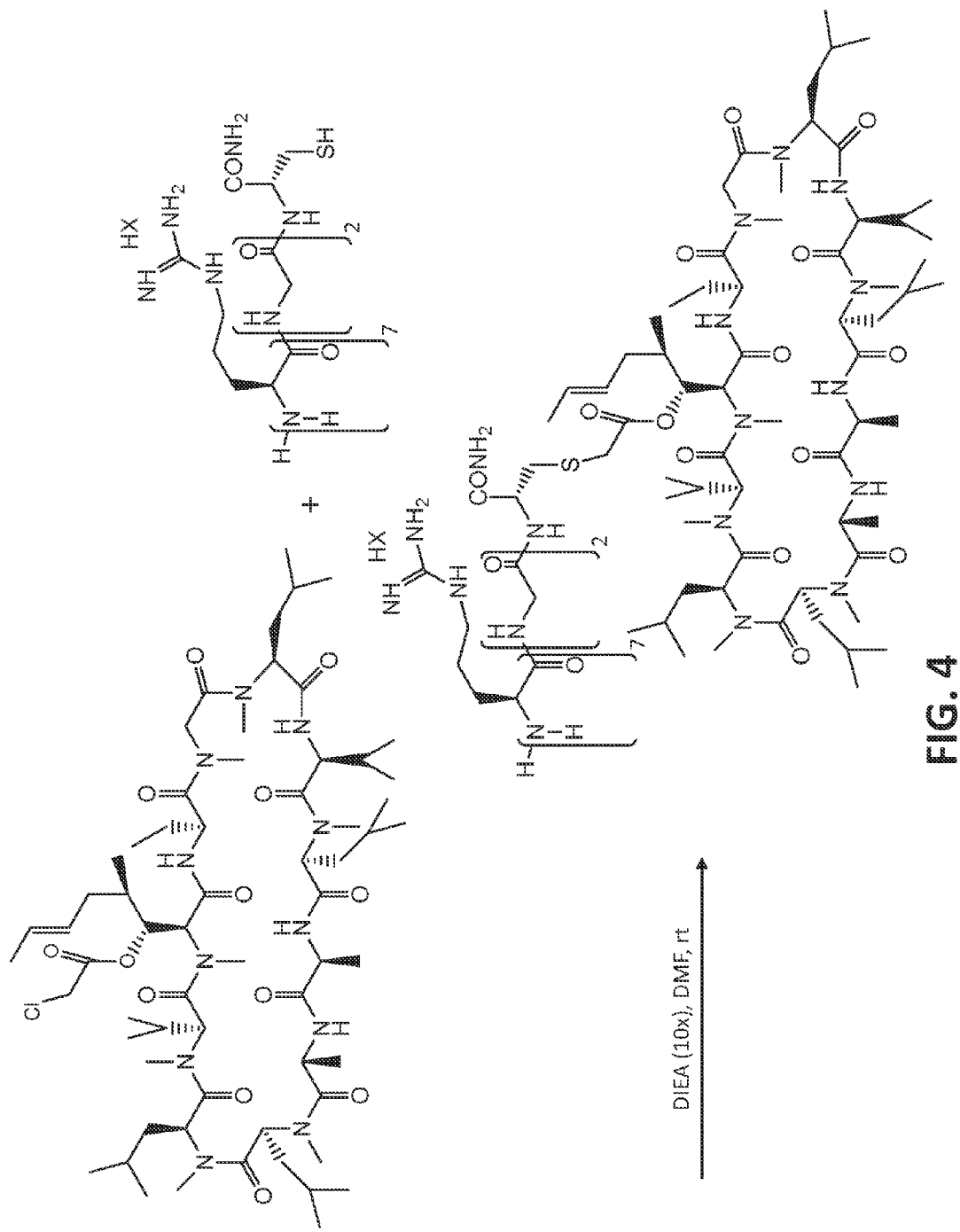

The peptide (34.7 mg, 15.3 µl) and the Cyclosporin A derivative (19.6 mg, 15.3 µmol) were dissolved in DMF (1.0 mL) under an $N_2$-atmosphere (FIG. 4). Diisopropylethylamine (19.7 mg, 153 µmol) was added and stirring at room temperature was continued. After 12 hours the solvent was removed in vacuo. The crude material was dissolved in water and purified by RP-HPLC (eluent: water/MeCN*TFA) yielding the pure product (24.1 mg, 6.8 mmol, 44%).

Example 16

Preparation of Hydrocortisone Conjugated to a Biotinylated Pentamer, Heptamer, and Nonamer of D-Arginine Methods A. Linking of Hydrocortisone to Delivery-Enhancing Transporters Step 1—Acylation of Hydrocortisone with Chloroacetic Anhydride.

A solution of hydrocortisone (200 mg, 0.55 mmol) and chloroacetic anhydride (113 mg, 0.66 mmol) in pyridine (5 mL) was stirred at room temperature for 2 h (FIG. 10). The solvent was evaporated off and the crude product was chromatographed on silica using 50% hexanes/ethyl acetate as the eluent. Product isolated a whites solid (139 mg, 58%).

Step 2—Linking to Transporter.

Figure 11:
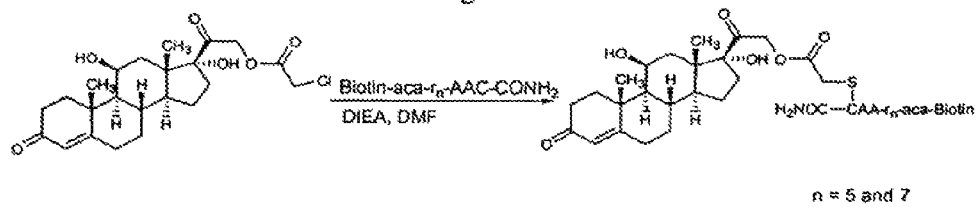
FIG. 11 shows a reaction for linking the acylated hydrocortisone to a transporter.

A solution of the chloroacetic ester of hydrocortisone (0.0137 mmol), a transporter containing a cysteine residue (0.0137) and diisopropylethylamine (DIEA) (0.0274 mmol) in dimethylformamide (DMF) (1 mL) was stirred at room temperature for 18 h (FIG. 11). The material was purified via reverse-phase HPLC using a water/acetonitrile gradient and lyophilized to provide a white powder.

r5 conjugate—12 mg obtained (29% isolated yield)
r7 conjugate—22 mg obtained (55% isolated yield)
R7 conjugate (SEQ ID NO:73)—13 mg obtained (33% isolated yield).

Example 17

Penetration of Taxol Conjugated to a Biotinylated Pentamer, Heptamer, and Nonamer of D-Arginine into the Skin of Nude Mice Methods 1. Conjugation of C-2' Activated Taxol Derivatives to Biotin-Labeled Peptides Synthesis of C-2' Derivatives Taxol (48.7 mg, 57.1 µmol) was dissolved in $CH_2Cl_2$ (3.0 mL) under an $N_2$-atmosphere. The solution was cooled to 0° C. A stock solution of the chloroformate of benzyl-(p-hydroxy benzoate) (200 mmol, in 2.0 mL $CH_2Cl_2$— freshly prepared from benzyl-(p-hydroxy benzoate) and diphosgene) was added at 0° C. and stirring at that temperature was continued for 5 hours, after which the solution was warmed to room temperature (FIG. 12). Stirring was continued for additional 10 hours. The solvents were removed in vacuo and the crude material was purified by flash chromatography on silica gel (eluent: EtOAc/hexanes 30%-70%) yielding the desired taxol C-2' carbonate (36.3 mg, 32.8 µmol, 57.4%).

Coupling to Biotin-Labeled Peptides.

Figure 13:
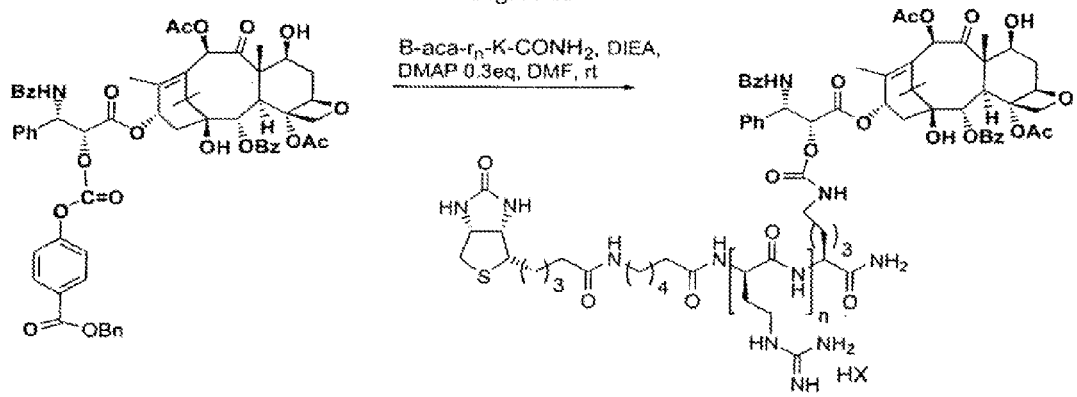
FIG. 13 shows a schematic of a reaction for coupling of a taxol derivative to a biotin-labeled peptide.

A procedure for coupling to biotin-labeled peptides is shown in FIG. 13. The taxol derivative and the biotin labeled peptide (1.2 equivalents) were dissolved in DMF (~10 µmol/mL DMF) under an $N_2$-atmosphere. Stock solutions of diisopropylethylamine (1.2 equivalents in DMF) and DMAP (0.3 equivalents in DMF) were added and stirring at room temperature was continued until all starting material was consumed. After 16 hours the solvent was removed in vacuo. The crude reaction mixture was dissolved in water and purified by RP-HPLC (eluent: water/MeCN*TFA) yielding the conjugates in the indicated yields:

B-aca-r5-K-taxol: 3.6 mg, 1.32 mmol, 20%.
B-aca-r7-K-taxol: 9.8 mg, 3.01 mmol, 44%.
B-aca-r9-K-taxol: 19.4 mg, 5.1 mmol, 67%.

Figure 14:
FIG. 14 shows a reaction for coupling of an unlabeled peptide to a C-2' derivative of taxol.

Unlabeled C-2' Carbamates:

The taxol derivative (12.4 mg, 11.2 µmol) and the unlabeled peptide (27.1 mg, 13.4 µmol) were dissolved in DMF (1.5 mL) under an $N_2$-atmosphere (FIG. 14). Diisopropylethylamine (1.7 mg, 13.4 µmol) was added as a stock solution in DMF, followed by DMAP (0.68 mg, 5.6 µmol) as a stock solution in DMF. Stirring at room temperature was continued until all starting material was consumed. After 16 hours the solvent was removed in vacuo. The crude material was dissolved in water and purified by RP-HPLC (eluent: water/MeCN*TFA) yielding the desired product (16.5 mg, 5.9 µmol, 53%).

Other C-2' Conjugates

The taxol derivative (8.7 mg, 7.85 µmol) was dissolved in EtOAc (2.0 mL). Pd/C (10%, 4.0 mg) was added and the reaction flask was purged with $H_2$ five times (FIG. 15A). Stirring under an atmosphere of hydrogen was continued for 7 hours. The Pd/C was filtered and the solvent was removed in vacuo. The crude material (6.7 mg, 6.58 µmol, 84%) obtained in this way was pure and was used in the next step without further purification.

The free acid taxol derivative (18.0 mg, 17.7 µmol) was dissolved in $CH_2Cl_2$ (2.0 mL). Dicyclohexylcarbodiimide (4.3 mg, 21.3 µmol) was added as a stock solution in $CH_2Cl_2$ (0.1 mL). N-Hydroxysuccinimide (2.0 mg, 17.7 µmol) was added as a stock solution in DMF (0.1 mL) (FIG. 15B). Stirring at room temperature was continued for 14 hours. The solvent was removed in vacuo and the resultant crude material was purified by flash chromatography on silica gel (eluent: EtOAc/hexanes 40%-80%) yielding the desired product (13.6 mg, 12.2 µmol, 69%).

The activated taxol derivative (14.0 mg, 12.6 µmol) and the peptide (30.6 mg, 15.1 µmol) were dissolved in DMF (3.0 mL) under an $N_2$-atmosphere (FIG. 15C). Diisopropylethylamine (1.94 mg, 15.1 µmol) was added as a stock solution in DMF (0.1 mL), followed by DMAP (0.76 mg, 6.3 μmol) as a stock solution in DMF 0.1 mL). Stirring at room temperature was continued until all the starting material was consumed. After 20 hours the solvent was removed in vacuo. The crude material was dissolved in water and purified by RP-HPLC (eluent: water/MeCN*TFA) yielding the two depicted taxol conjugates in a ration of 1:6 (carbonate vs carbamate, respectively).

Example 18

This example illustrates a method of linking active agents such as acyclovir to transport moieties. See, FIG. 35.

Acyclovir (1 eq) was dissolved in dry N,N-dimethylformamide under a nitrogen atmosphere. Chloroacetic anhydride (1 eq), pyridine (1 eq), and DMAP (0.25 eq) were added subsequently to the reaction with stirring. The reaction was permitted to stir at room temperature for an additional 4 hours. The reaction was halted by removal of the solvent under reduced pressure. The residue was dissolved in methylene chloride and washed with saturated aqueous ammonium chloride followed by saturated aqueous ammonium bicarbonate and brine. The organic layer was concentrated in vacuo and the residue purified by silica gel chromatography to provide the acyclovir chloroacetyl ester.

The resultant chloroacetyl ester was dissolved in dry N,N-dimethylformamide under a nitrogen atmosphere. To the solution was added Hunig's base (1 eq) and AcHN—C-aca-R8-CONH2*8HCl (SEQ ID NO:69) with rapid stirring. The reaction was allowed to proceed until TLC analysis indicated that all of the starting material had been consumed (ca 2 hours). The reaction was halted by removal of the solvent under reduced pressure. The residue was purified by RP-HPLC to provide the desired acyclovir conjugate.

Example 19

This example illustrates a method of linking active agents such as acyclovir to transport moieties. See, FIG. 36.

Disphosgene (0.5 eq) was dissolve in dry methylene chloride and cooled to −10° C. To the solution was added triethylamine (1 eq) as a solution in methylene chloride. The mixture was stirred for 15 minutes at which time acyclovir was added to the reaction as a solution in methylene chloride. The reaction was permitted to stir at room temperature for an additional 4 hours. The reaction was quenched with saturated aqueous ammonium chloride followed by washes of saturated aqueous ammonium bicarbonate and brine. The organic layer was concentrated in vacuo and the residue purified by rapid filtration over silica gel to provide the acyclovir chloroformate.

The chloroformate was dissolved in dry methylene chloride under a nitrogen atmosphere. Mercaptoethanol (1 eq) was added to the reaction as a solution in dry methylene chloride. The reaction was allowed to stir for 10 hours under a nitrogen atmosphere. The solution was concentrated under reduced and placed under high vacuum for 24 hours to remove residual mercaptoethanol. The resultant mercaptoethyl carbonate was used without further purification.

The carbonate (1 eq) was dissolved DMF/water. To the solution was added the activated peptide NPYs-CR*—CONH2*8HCl (1 eq) with rapid stirring. A bright yellow color developed immediately and the reaction was allowed to stir at room temperature for an additional 5 hours. The reaction was purified directly by RP-HPLC to provide the desired acyclovir conjugate.

Example 20

This example illustrates a method of linking active agents such as corticoid steroids to transport moieties. See, FIG. 37.

Prednisolone α-chloroester—

To a solution of prednisolone (1.38 mmol), scandium triflate (0.83 mmol) and chloroacetic anhydride (4.14 mmol) in dry THF was added dimethylaminopyridine (4.14 mmol). The solution turned bright yellow upon addition of dimethylaminopyridine. After 30 minutes the solvent was evaporated off and the crude material taken up into ethyl acetate (100 mL). The ethyl acetate layer was washed with 1.0 N HCl and brine. The organic phase was collected, dried ($Na_2SO_4$) and evaporated to provide the product as a white solid.

$H_2N$—C(prednisolone)-r8-$CONH_2$:

A solution of prednisolone α-chloroester (1 equivalent), $H_2N$—C-r8-$CONH_2$ (1 equivalent) and diisopropylethylamine (1.2 equivalent) in dimethylformamide (1 mL) was stirred for 18 hours. The dimethylformamide was evaporated off. The crude product purified by reverse-phase HPLC (22 mm×250 mm C-18 column, a 5-10% $CH_3CN/H_2O$ gradient with 0.1% trifluoroacetic acid, 214 and 254 nm UV detection) and lyophilized to provide the 9 TFA salt. The material was then subjected to ion exchange chromatography to provide prednisolone conjugate (9 HCl salt) as a tan solid.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

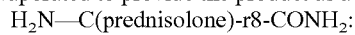

What is claimed is:

1. A method for enhancing delivery of a compound into and across an animal ocular tissue, the method comprising:
   administering to the ocular tissue a conjugate comprising the compound and a delivery-enhancing transporter, wherein:
   i. the compound is attached to the delivery-enhancing transporter through a disulfide linker, and
   ii. the delivery-enhancing transporter comprises fewer than 50 subunits and comprises at least 5 guanidine or amidino moieties, thereby increasing delivery of the conjugate into the ocular tissue compared to delivery of the compound in the absence of the delivery-enhancing transporter.

2. The method of claim 1, wherein delivery of the conjugate into the ocular tissue is increased at least two-fold compared to delivery of the compound in the absence of the delivery-enhancing transporter.

3. The method of claim 1, wherein delivery of the conjugate into the ocular tissue is increased at least ten-fold compared to delivery of the compound in the absence of the deliver-enhancing transporter.

4. The method of claim 1, wherein the ocular tissue is one or more layers of epithelial or endothelial tissue.

5. The method of claim 1, wherein the ocular tissue is the retina.

6. The method of claim 1, wherein the ocular tissue is the optic nerve.

7. The method of claim 1, wherein the subunits are amino acids.

8. The method of claim 1, wherein the conjugate comprises at least two delivery-enhancing transporters.

9. The method of claim 1, wherein the conjugate is administered as an eye drop.

10. The method of claim 1, wherein the delivery-enhancing transporter consists essentially of 5 to 50 amino acids, at least 50 percent of which amino acids are arginines or analogs thereof.

11. A method for enhancing delivery of a compound into and across an animal ocular tissue, the method comprising:
    administering to the ocular tissue a conjugate comprising the compound and a delivery-enhancing transporter, wherein:
    i. the compound is attached to the delivery-enhancing transporter through a photocleavable linker, and
    ii. the delivery-enhancing transporter comprises fewer than 50 subunits and comprises at least 5 guanidine or amidino moieties, thereby increasing delivery of the conjugate into the ocular tissue compared to delivery of the compound in the absence of the delivery-enhancing transporter.

12. The method of claim 11, wherein delivery of the conjugate into the ocular tissue is increased at least two-fold compared to delivery of the compound in the absence of the delivery-enhancing transporter.

13. The method of claim 11, wherein delivery of the conjugate into the ocular tissue is increased at least ten-fold compared to delivery of the compound in the absence of the delivery-enhancing transporter.

14. The method of claim 11, wherein the ocular tissue is one or more layers of epithelial or endothelial tissue.

15. The method of claim 11, wherein the ocular tissue is the retina.

16. The method of claim 11, wherein the ocular tissue is the optic nerve.

17. The method of claim 11, wherein the subunits are amino acids.

18. The method of claim 11, wherein the conjugate comprises at least two delivery-enhancing transporters.

19. The method of claim 11, wherein the conjugate is administered as an eye drop.

20. The method of claim 11, wherein the delivery-enhancing transporter consists essentially of 5 to 50 amino acids, at least 50 percent of which amino acids are arginines or analogs thereof.

* * * * *

UNITED STATES PATENT AND TRADEMARK OFFICE
CERTIFICATE OF CORRECTION

PATENT NO. : 8,729,010 B2  
APPLICATION NO. : 13/608975  
DATED : May 20, 2014  
INVENTOR(S) : Rothbard et al.

Page 1 of 1

It is certified that error appears in the above-identified patent and that said Letters Patent is hereby corrected as shown below:

Title page under (75) Inventors: change "Leo P. McGrane" to --P. Leo McGrane--

Signed and Sealed this  
Second Day of September, 2014

Michelle K. Lee  
*Deputy Director of the United States Patent and Trademark Office*